United States Patent
Da Costa et al.

(10) Patent No.: US 10,449,208 B2
(45) Date of Patent: Oct. 22, 2019

(54) ANTIVIRAL PRODRUGS OF TENOFOVIR

(71) Applicants: Merck Sharp & Dohme Corp., Rahay, NJ (US); IDENIX PHARMACEUTICALS LLC, Cambridge, MA (US)

(72) Inventors: Daniel Da Costa, Montarnaud (FR); Cyril B. Dousson, Herault (FR); David Dukhan, Montpellier (FR); Jean-Laurent Paparin, Vendemian (FR); Houcine Rahali, Saint Laurent des Arbres (FR); Izzat Raheem, Doylestown, PA (US)

(73) Assignees: Merck Sharp & Dohme Corp., Rahway, NJ (US); Idenix Pharmaceuticals LLC., Cambridge, MA (US)

( * ) Notice: Subject to any disclaimer, the term of this patent is extended or adjusted under 35 U.S.C. 154(b) by 0 days.

(21) Appl. No.: 16/327,631

(22) PCT Filed: Aug. 22, 2017

(86) PCT No.: PCT/US2017/047892
§ 371 (c)(1),
(2) Date: Feb. 22, 2019

(87) PCT Pub. No.: WO2018/039157
PCT Pub. Date: Mar. 1, 2018

(65) Prior Publication Data
US 2019/0183912 A1 Jun. 20, 2019

Related U.S. Application Data

(60) Provisional application No. 62/379,455, filed on Aug. 25, 2016.

(51) Int. Cl.
*A61K 31/675* (2006.01)
*A61P 31/12* (2006.01)
*A61K 45/00* (2006.01)

(52) U.S. Cl.
CPC ............ *A61K 31/675* (2013.01); *A61P 31/12* (2018.01); *A61K 45/05* (2013.01)

(58) Field of Classification Search
None
See application file for complete search history.

(56) References Cited

U.S. PATENT DOCUMENTS

| | | | | |
|---|---|---|---|---|
| 5,627,165 A * | 5/1997 | Glazier | ................. | C07C 69/732 514/143 |
| 5,792,756 A * | 8/1998 | Starrett, Jr. | ......... | C07F 9/65616 514/86 |
| 5,935,946 A | 8/1999 | Munger, Jr. et al. | | |
| 5,977,089 A | 11/1999 | Arimilli et al. | | |
| 7,390,791 B2 | 6/2008 | Becker et al. | | |
| 8,754,065 B2 | 6/2014 | Liu et al. | | |
| 9,822,138 B2 | 11/2017 | Vachal et al. | | |
| 2015/0105350 A1* | 4/2015 | Ramanathan | .......... | A61K 31/35 514/81 |
| 2015/0111856 A1 | 4/2015 | Dahl et al. | | |
| 2016/0083407 A1* | 3/2016 | Hostetler | ............ | C07F 9/65616 514/81 |
| 2018/0179208 A1* | 6/2018 | Paparin | ................. | A61K 31/675 |
| 2018/0362562 A1 | 12/2018 | Raheem et al. | | |
| 2018/0362563 A1 | 12/2018 | Fu et al. | | |

FOREIGN PATENT DOCUMENTS

| | | | |
|---|---|---|---|
| EP | 2891658 A1 * | 7/2015 | ........... A61K 31/675 |
| EP | 2891658 A1 | 7/2015 | |
| WO | WO-9119721 A1 * | 12/1991 | ........... C07C 69/732 |
| WO | WO-2013167743 A1 * | 11/2013 | ............ A61K 45/06 |
| WO | 2017007701 A1 | 1/2017 | |
| WO | 2018080903 A1 | 5/2018 | |
| WO | 2018118826 A1 | 6/2018 | |

OTHER PUBLICATIONS

B. Kearney et al., 43 Clinical Pharmacokinetics, 595-612 (2004) (Year: 2004).*
Aitipamula, S., et al, "Polymorphs, Salts, and Cocrystals: What's in a Name", Crystal Growth and Design, 2012, pp. 2147-2152, vol. 12.
Higuchi, T., et al., "Pro-drugs as NovelDelivery Systems", A.C.S. Symposium Series, 1987, 14, pp. 1-6.
Kesisoglou, F., et al, "Nanosizing—Oral Formulation Developement and Biopharmaceutical Evaluation", Adv. Drug Delivery, 2007, pp. 631-644, vol. 59, No. 7.
Martin, A., et al, Simplification of Antiretroviral Therapy, Clinical Infectious Diseases, 2009, pp. 1591-1601, vol. 49.
Serajuddin, A., et al.,, "Solid Dispersion of Poorly Water-Soluble Drugs: Early Promises, Subsequent Problems, and Recent Breakthroughs", J. Pharm Sci., 1999, pp. 1058-1066, vol. 88, No. 10.
International Search Report and Written Opinion—PCT/US2017/47892—dated Oct. 19, 2017.
Rautio, J., et al., "Prodrugs: Design and Clinical Applications", Nat. Rev. Drug Discov., 2008, pp. 255-270, vol. 7.

* cited by examiner

*Primary Examiner* — Alexander R Pagano
(74) *Attorney, Agent, or Firm* — Eric A. Meade; John C. Todaro

(57) ABSTRACT

Compounds of Formula I: and pharmaceutically acceptable salts and co-crystals thereof are useful for the inhibition of HIV reverse transcriptase. The compounds may also be useful for the prophylaxis or treatment of infection by HIV and in the prophylaxis, delay in the onset or progression, and treatment of AIDS. The compounds and their salts can be employed as ingredients in pharmaceutical compositions, optionally in combination with other antiviral agents, immunomodulators, antibiotics or vaccines.

18 Claims, No Drawings

ANTIVIRAL PRODRUGS OF TENOFOVIR

CROSS-REFERENCE TO RELATED APPLICATIONS

This application is a 35 U.S.C. § 371 filing from International Application No. PCT/US2017/047892 filed August 22, 2017, which claims priority to U.S. Provisional Application No. 62/379,455, filed Aug. 25, 2016.

The aforementioned application to which this application claims priority is herein incorporated by reference in its entirety.

BACKGROUND OF THE INVENTION

The retrovirus designated human immunodeficiency virus (HIV), particularly the strains known as HIV type-1 (HIV-1) and type-2 (HIV-2), have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HW is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA As a ribonuclease, RT destroys the original viral RNA and frees the DNA just produced from the original RNA. During the viral RNA-dependent polymerization process, RT's ribonuclease activity is required for removing RNA and leaving the polypurine tract preserved for initiation of DNA-dependent polymerization. As a DNA-dependent DNA polymerase, RT makes a second, complementary DNA strand using the first DNA strand as a template. The two strands form double-stranded DNA, which is integrated into the host cell's genome by HIV integrase.

It is known that compounds that inhibit enzymatic functions of HIV RT will inhibit HIV replication in infected cells. These compounds are useful in the treatment of HIV infection in humans. There are two classes of RT inhibitors: one is non-nucleoside active site competitive RT inhibitors (NNRTIs), such as efavirenz (EFV), nevirapine (NVP), etravirine (ETR), and rilpivirine (RPV), and the other is active site RT inhibitors which include nucleoside reverse transcriptase inhibitors (NsRTIs) and nucleotide reverse transcriptase inhibitors (NtRTIs), collectively referred to as NRTIs. Examples of NsRTI's include 3'-azido-3'-deoxythymidine (AZT), 2',3'-dideoxyinosine (ddI), 2',3'-dideoxycytidine (ddC), 2',3'-didehydro-2',3'-dideoxythymidine (d4T), 2',3'-dideoxy-3'-thiacytidine (3TC), abacavir, and emtricitabine. Examples of NtRTIs include tenofovir (TFV, also known as PMPA, 9-(2-phosphonyl-methoxypropyl)adenine), tenofovir disoproxil fumarate (VIREAD®, U.S. Pat. Nos. 5,977,089, 5,935,946) and tenofovir alafenamide fumarate (U.S. Pat. Nos. 7,390,791, 8,754,065).

TFV belongs to a class of HIV anti-retroviral (ARV) agents known as nucleotide analog reverse transcriptase inhibitors (NRTIs). Tenofovir is a monophosphonate:

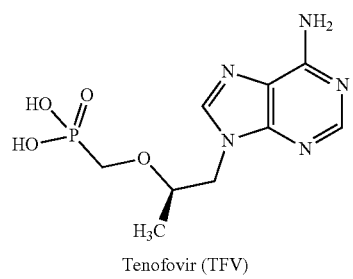 [SMILES: C[C@H](Cn1cnc2c(N)ncnc21)OCP(=O)(O)O]

Tenofovir (TFV)

After being taken up by cells, TFV is first converted to tenofovir-monophosphate (TFV-MP) by adenosine monophosphate kinase and then to the active antiviral tenofovir-diphosphate (TFV-DP) by 5'-nucleoside diphosphate kinase.

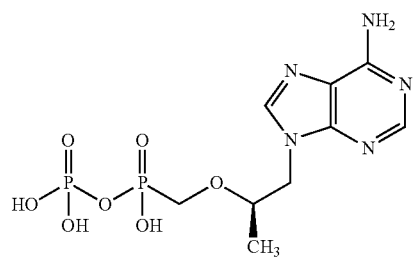

Tenofovir-monophosphate (TFV-MP)

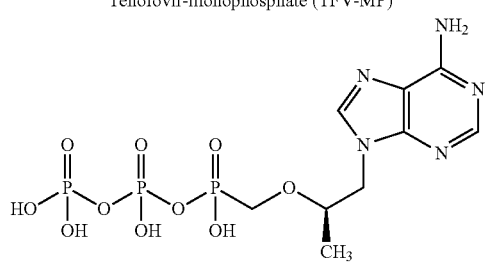

Tenofovir-diphosphate (TFV-DP)

TFV-DP inhibits HIV DNA synthesis by competing with the natural substrate, deoxyadenosine triphosphate, for incorporation into the complementary DNA strand by HIV reverse transcriptase; following incorporation, TFV acts as a chain terminator due to lack of a 3'-hydroxyl group that is required for addition of the next nucleotide. TFV has poor cellular permeability and thus has limited bioavailability. Tenofovir disoproxil fumarate (TDF) is approved for treating HIV infection and is marketed by Gilead under the trade name VIREAD™. The disoproxil prodrug improves cell permeability and absorption after oral dosing, with the pro-moiety being cleaved rapidly after absorption to yield the parent TFV. As a result, the circulating level of TFV is much higher than that of TDF. Tenofovir alafenamide fumarate (TAF) is currently approved by the USFDA as an active ingredient in combination with additional ARVs for treating HIV infection in the pharmaceutical products GENVOYA®, ODEFSEY® and DESCOVY®.

While each of the foregoing drugs is effective in treating HIV infection and AIDS, there remains a need to develop additional HIV antiviral drugs including additional RT inhibitors. A particular problem is the development of mutant HIV strains that are resistant to the known inhibitors. The use of RT inhibitors to treat AIDS often leads to viruses that are less sensitive to the inhibitors. This resistance is typically the result of mutations that occur in the reverse transcriptase segment of the pol gene. The continued use of antiviral compounds to prevent HIV infection will inevitably result in the emergence of new resistant strains of HIV. Accordingly, there is a particular need for new RT inhibitors that are effective against mutant HIV strains.

SUMMARY OF THE INVENTION

The present invention is directed lactate and glycolate prodrugs of tenofovir and their use in the inhibition of nucleotide reverse transcriptase. In addition to the use of said compounds in the inhibition of HIV reverse transcriptase, the invention is also directed to the use of said compounds for prophylaxis of infection by HIV, the treatment of infection by HIV, and the prophylaxis, treatment, and/or delay in the onset or progression of AIDS and/or ARC.

DETAILED DESCRIPTION OF THE INVENTION

The present invention is directed to a compound of structural Formula I:

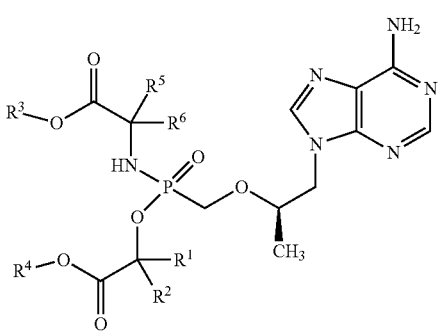

I or a pharmaceutically acceptable salt thereof, wherein:
$R^1$ and $R^2$ are each independently selected from (a) H, (b) —$C_{1-4}$alkyl, (c) —$C_{1-4}$alkyl substituted with —OH, —SH, —$SCH_3$, —$NH_2$, —NH—C(=NH)—$NH_2$, (d) —$CH_2$-phenyl, (e) —$CH_2$-phenol, (f) —$(CH_2)_{1-2}$—COOH, (g) —$(CH_2)_{1-2}$—$CONH_2$, (h) —$CH_2$-1H-indole, (i) —$CH_2$-imidazole, (j) aryl (for example but not limited to phenyl or naphthyl) or (k) heteroaryl (for example but not limited to pyridine);
$R^3$ is selected from:
(a) —$C_{1-10}$alkyl unsubstituted or substituted with one to three substituents independently selected from fluoro, chloro, bromo, —$OR^{7a}$, —SH, —$NR^{9a}R^{10a}$, —$C_{3-6}$cycloalkyl or spiro—$C_{3-6}$cycloalkyl,
(b) —$CH_2$-phenyl unsubstituted or substituted with one to three substituents independently selected from fluoro, chloro, bromo, —$OR^{8a}$, —SH, —$NR^{9a}R^{10a}$ or —$C_{1-3}$alkyl,
(c) —$C_{3-8}$cycloalkyl unsubstituted or substituted with one to three substituents independently selected from fluoro, chloro, bromo, —$OR^{8a}$, —SH, —$NR^{9a}R^{10a}$ or —$C_{1-3}$alkyl,
(d) aryl unsubstituted or substituted with one to three substituents independently selected from fluoro, chloro, bromo, —$OR^{8a}$, —SH, —$NR^{9a}R^{10a}$ or —$C_{1-3}$alkyl,
(e) —$C_{1-5}$alkyl—X—$C_{1-5}$alkyl wherein X is O, S or NH,
(f) heteroaryl unsubstituted or substituted with one to three substituents independently selected from fluoro chloro, bromo, —$OR^{8a}$, —SH, —$NR^{9a}R^{10a}$ or —$C_{1-3}$alkyl, or
(g) a heterocyclic ring unsubstituted or substituted with one to three substituents independently selected from fluoro, chloro, bromo, —$OR^{8a}$, —SH, —$NR^{9a}R^{10a}$ or —$C_{1-3}$alkyl;
$R^4$ is selected from:
(a) —$C_{1-10}$alkyl unsubstituted or substituted with one to three substituents independently selected from fluoro, chloro, bromo, —$OR^{7b}$, —SH, —$NR^{9b}R^{10b}$, —$C_{3-6}$cycloalkyl or spiro—$C_{3-6}$cycloalkyl,
(b) —$CH_2$-phenyl unsubstituted or substituted with one to three substituents independently selected from fluoro, chloro, bromo, —$OR^{8b}$, —SH, —$NR^{9b}R^{10b}$ or —$C_{1-3}$alkyl,
(c) —$C_{3-8}$cycloalkyl unsubstituted or substituted with one to three substituents independently selected from fluoro, chloro, bromo, —$OR^{8b}$, —SH, —$NR^{9b}R^{10b}$ or —$C_{1-3}$alkyl,
(d) aryl unsubstituted or substituted with one to three substituents independently selected from fluoro, chloro, bromo, —$OR^{8b}$, —SH, —$NR^{9b}R^{10b}$ or —$C_{1-3}$alkyl,
(e) —$C_{1-5}$alkyl—X—$C_{1-5}$alkyl wherein X is O, S or NH,
(f) heteroaryl unsubstituted or substituted with one to three substituents independently selected from fluoro chloro, bromo, —$OR^{8b}$, —SH, —$NR^{9b}R^{10b}$ or —$C_{1-3}$alkyl, or
(g) a heterocyclic ring unsubstituted or substituted with one to three substituents independently selected from fluoro, chloro, bromo, —$OR^{8b}$, —SH, —$NR^{9b}R^{10b}$ or —$C_{1-3}$alkyl;
$R^5$ and $R^6$ are each independently selected from (a) —$C_{1-4}$alkyl, (b) —$C_{1-4}$alkyl substituted with —OH, —SH, —$SCH_3$, —$NH_2$, —NH—C(=NH)—$NH_2$, (c) —$CH_2$-phenyl, (d) —$CH_2$-phenol, (e) —$(CH_2)_{1-2}$—COOH, (f) —$(CH_2)_{1-2}$—$CONH_2$, (g) —$CH_2$-1H-indole, (h) —$CH_2$-imidazole, (i) aryl (for example but not limited to phenyl or naphthyl) or (j) heteroaryl (for example but not limited to pyridine);
or $R^5$ and $R^6$ are joined together with the carbon to which they are both attached to form —$C_{3-6}$cycloalkyl or a 4 to 6-membered heterocyclic ring;
$R^{7a}$ and $R^{7b}$ are each independently selected from —H or —$C_{3-6}$cycloalkyl;
$R^{8a}$ and $R^{8b}$ are each independently selected from —H, —$C_{1-3}$alkyl or —$C_{3-6}$cycloalkyl;
$R^{9a}$ and $R^{10a}$ are each independently selected from —H, —$C_{1-3}$alkyl or —$C_{3-6}$cycloalkyl; and
$R^{9b}$ and $R^{10b}$ are each independently selected from —H, —$C_{1-3}$alkyl or —$C_{3-6}$cycloalkyl.

In Embodiment 1 of this invention are compounds of Formula I having structural Formula Ia:

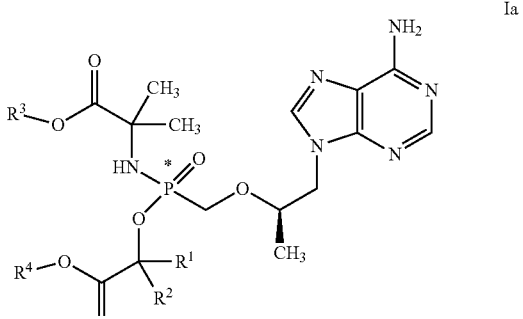

Ia or a pharmaceutically acceptable salt thereof, wherein the variables are as defined in Formula I.

In Embodiment 2 of this invention are compounds of Formula I, Formula Ia or pharmaceutically acceptable salts thereof, wherein $R^1$ is —H or —$C_{1-4}$alkyl. In a class thereof, $R^1$ is —H or —$CH_3$.

In Embodiment 3 of this invention are compounds of Formula I, Formula Ia or Embodiment 2, or any class thereof, or pharmaceutically acceptable salts of the foregoing, wherein $R^2$ is —H, —$C_{1-4}$alkyl or —$CH_2$-phenyl. In a class thereof $R^2$ is —H, —$CH_3$ or —$CH_2$-phenyl. phenyl.

In Embodiment 4 of this invention are compounds of Formula I, Embodiment 2 or Embodiment 3, or any class thereof, or pharmaceutically acceptable salts of the foregoing, wherein $R^5$ and $R^6$ are each independently selected from —$C_{1-4}$alkyl (for example both $R^5$ and $R^6$ are —$CH_3$), or $R^5$ and $R^6$ are joined together with the carbon to which they are both attached to form cyclopropyl, cyclobutyl, cyclopentyl or cyclohexyl. In a class thereof, $R^5$ and $R^6$ are both —$CH_3$. In another class thereof, $R^5$ and $R^6$ are joined together with the carbon to which they are both attached to form cyclopropyl, cyclobutyl, cyclopentyl or cyclohexyl.

In Embodiment 5 of this invention are compounds of Formula I, Formula Ia, or any one of Embodiments 2, 3 or 4, or any class thereof, or pharmaceutically acceptable salts of the foregoing, wherein $R^3$ is
(a) —$C_{1-8}$alkyl, —$CH_2CH_2OH$, —$CH_2CH_2CH_2OH$, —$CH_2CH_2SH$, —$CH_2CH_2CH_2SH$, —$CH_2CH_2NH_2$, —$CH_2CH_2CH_2NH_2$,
(b) —$CH_2$-phenyl, unsubstituted or substituted with one to three substituents independently selected from fluoro, chloro, bromo, —$OR^{8a}$, —SH, —$NR^{9a}R^{10a}$ or —$C_{1-3}$alkyl,
(c) —$C_{3-6}$cycloalkyl, unsubstituted or substituted with one to three substituents independently selected from fluoro, chloro, bromo, —$OR^{8a}$, —SH, —$NR^{9a}R^{10a}$ or —$C_{1-3}$alkyl,
(d) phenyl or naphthyl, each unsubstituted or substituted with one to three substituents independently selected from fluoro, chloro, bromo, —$OR^{8a}$, —SH, —$NR^{9a}R^{10a}$ or —$C_{1-3}$alkyl,
(e) —$CH_2CH_2OCH_3$, —$CH_2CH_2CH_2OCH_3$, —$CH_2CH_2SCH_3$, —$CH_2CH_2CH_2SCH_3$, —$CH_2CH_2NHCH_3$, —$CH_2CH_2CH_2NHCH_3$,
(f) pyridyl, unsubstituted or substituted with one to three substituents independently selected from fluoro chloro, bromo, —$OR^{8a}$, —SH, —$NR^{9a}R^{10a}$ or —$C_{1-3}$alkyl, or
(g) piperidinyl, pyrrolidinyl, tetrahydrofuranyl, or tetrahydropyranyl, each unsubstituted or substituted with one to three substituents independently selected from fluoro, chloro, bromo, —$OR^{8a}$, —SH, —$NR^{9a}R^{10a}$ or —$C_{1-3}$alkyl;

In a class of Embodiment 5, $R^3$ is:
(a) —$C_{1-8}$alkyl, —$CH_2CH_2OH$, —$CH_2CH_2CH_2OH$, —$CH_2CH_2SH$, —$CH_2CH_2CH_2SH$, —$CH_2CH_2NH_2$, —$CH_2CH_2CH_2NH_2$,
(b) —$CH_2$-phenyl, unsubstituted or substituted with one to three substituents independently selected from fluoro, chloro, bromo, —$OR^{8a}$, —SH, —$NR^{9a}R^{10a}$ or —$C_{1-3}$alkyl, or
(c) —$C_{3-6}$cycloalkyl, unsubstituted or substituted with one to three substituents independently selected from fluoro, chloro, bromo, —$OR^{8a}$, —SH, —$NR^{9a}R^{10a}$ or —$C_{1-3}$alkyl.

In Embodiment 6 of this invention are compounds of Formula I, Formula Ia, or any one of Embodiments 2, 3, 4 or 5, or any class thereof, or pharmaceutically acceptable salts of the foregoing, wherein $R^4$ is
(a) —$C_{1-8}$alkyl, —$CH_2CH_2OH$, —$CH_2CH_2CH_2OH$, —$CH_2CH_2SH$, —$CH_2CH_2CH_2SH$, —$CH_2CH_2NH_2$, —$CH_2CH_2CH_2NH_2$,
(b) —$CH_2$-phenyl, unsubstituted or substituted with one to three substituents independently selected from fluoro, chloro, bromo, —$OR^{8b}$, —SH, —$NR^{9b}R^{10b}$ or —$C_{1-3}$alkyl,
(c) —$C_{3-6}$cycloalkyl, unsubstituted or substituted with one to three substituents independently selected from fluoro, chloro, bromo, —$OR^{8b}$, —SH, —$NR^{9b}R^{10b}$ or —$C_{1-3}$alkyl,
(d) phenyl or naphthyl, each unsubstituted or substituted with one to three substituents independently selected from fluoro, chloro, bromo, —$OR^{8b}$, —SH, —$NR^{9b}R^{10b}$ or —$C_{1-3}$alkyl,
(e) —$CH_2CH_2OCH_3$, —$CH_2CH_2CH_2OCH_3$, —$CH_2CH_2SCH_3$, —$CH_2CH_2CH_2SCH_3$, —$CH_2CH_2NHCH_3$, —$CH_2CH_2CH_2NHCH_3$,
(f) pyridyl, unsubstituted or substituted with one to three substituents independently selected from fluoro chloro, bromo, —$OR^{8b}$, —SH, —$NR^{9b}R^{10b}$ or —$C_{1-3}$alkyl, or
(g) piperidinyl, pyrrolidinyl, tetrahydrofuranyl, or tetrahydropyranyl, each unsubstituted or substituted with one to three substituents independently selected from fluoro, chloro, bromo, —$OR^{8b}$, —SH, —$NR^{9b}R^{10b}$ or —$C_{1-3}$alkyl;

In a class of Embodiment 6, $R^4$ is
(a) —$C_{1-8}$alkyl, —$CH_2CH_2OH$, —$CH_2CH_2CH_2OH$, —$CH_2CH_2SH$, —$CH_2CH_2CH_2SH$, —$CH_2CH_2NH_2$, —$CH_2CH_2CH_2NH_2$,
(b) —$CH_2$-phenyl, unsubstituted or substituted with one to three substituents independently selected from fluoro, chloro, bromo, —$OR^{8b}$, —SH, —$NR^{9b}R^{10b}$ or —$C_{1-3}$alkyl, or
(c) —$C_{3-6}$cycloalkyl, unsubstituted or substituted with one to three substituents independently selected from fluoro, chloro, bromo, —$OR^{8b}$, —SH, —$NR^{9b}R^{10b}$ or —$C_{1-3}$alkyl.

In Embodiment 7 of this invention are compounds of Formula Formula Ia, or any one of Embodiments 2, 3, 4, 5 or 6, or any class thereof, or pharmaceutically acceptable salts of the foregoing, wherein $R^3$ and $R^4$ are each independently selected from —$C_{1-8}$alkyl, —$C_{3-6}$cycloalkyl or —$CH2$-phenyl, and wherein each of $R^3$ and $R^4$ is unsubstituted or substituted as defined in Formula I. In class (A) thereof, $R^3$ is selected from —$C_{1-8}$alkyl, —$C_{3-6}$cycloalkyl or —$CH_2$-phenyl. In class (B) thereof, $R^4$ is selected from —$C_{1-8}$alkyl or —$C_{3-6}$cycloalkyl. In class (C) thereof, $R^3$ is selected from —$C_{1-8}$alkyl, —$C_{3-6}$cycloalkyl or —$CH_2$-phenyl and $R^4$ is selected from —$C_{1-8}$alkyl or —$C_{3-6}$cycloalkyl. In class (D) thereof, $R^3$ and $R^4$ are each unsubstituted. In class (E) thereof, $R^3$ and $R^4$ are each unsubstituted and independently selected from —$C_{2-6}$alkyl, cyclopropyl, cyclobutyl, cyclopentyl, cyclohexyl, or —$CH_2$-phenyl.

In Embodiment 8 are compounds of Formula I or a pharmaceutically acceptable salt thereof, wherein:
$R^1$ is —H or —$CH_3$;
$R^2$ is —H, —$CH_3$ or —$CH_2$-phenyl;
$R^3$ is selected from —$C_{1-8}$alkyl, —$C_{3-6}$cycloalkyl or —$CH_2$-phenyl;
$R^4$ is selected from —$C_{1-8}$alkyl or —$C_{3-6}$cycloalkyl; and
$R^5$ and $R^6$ are both —$CH_3$;
or $R^5$ and $R^6$ are joined together with the carbon to which they are both attached to form —$C_{3-6}$cycloalkyl.

In a class of Embodiment 8, $R^3$ is selected from —$C_{2-6}$alkyl, —$C_{3-6}$cycloalkyl or —$CH2$-phenyl, and $R^4$ is selected from —$C_{2-6}$alkyl or —$C_{3-6}$cycloalkyl.

Reference to the compounds of Formula I herein encompasses the compounds of Formula I and Ia, and all embodiments, classes and sub-classes thereof. The compounds of the invention encompass compounds of Formula I and salts thereof when such salts are possible, including pharmaceutically acceptable salts.

As used herein, "alkyl" refers to both branched- and straight-chain saturated aliphatic hydrocarbon groups having the specified number of carbon atoms in a specified range. For example the term "$C_{1-10}$ alkyl" means linear or branched chain alkyl groups, including all possible isomers, having 1, 2, 3, 4, 5, 7, 8, 9 or 10 carbon atoms, and includes each of the decyl, nonyl, octyl, heptyl and pentyl isomers as well as n-, iso-, sec- and tent-butyl (butyl, s-butyl, i-butyl, t-butyl, Bu=butyl, collectively "—C$_4$alkyl"), n- and iso -propyl (propyl, i-propyl, Pr=propyl, collectively "—C$_3$alkyl"), ethyl (Et) and methyl (Me). "C$_{1-4}$alkyl" has 1, 2, 3 or 4 carbon atoms, and includes each of n-, iso-, sec- and tert-butyl, n- and i-propyl, ethyl and methyl.

"Cycloalkyl" refers to a cyclized alkyl ring having the indicated number of carbon atoms in a specified range. Thus, for example, "C$_{3-8}$ cycloalkyl" encompasses each of cyclopropyl, cyclobutyl, cyclopentyl, cyclohexyl, cyloheptyl and cyclooctyl. "C$_{3-6}$cycloalkyl" encompasses each of cyclopropyl, cyclobutyl, cyclopentyl and cyclohexyl. When cycloalkyl is a substituent on an alkyl group in a compound of Formula I, the cycloalkyl substituent can be bonded to any available carbon in the alkyl group. The following are illustrations of —C$_{3-6}$cycloalkyl substituents wherein the substituent is cyclopropyl in bold:

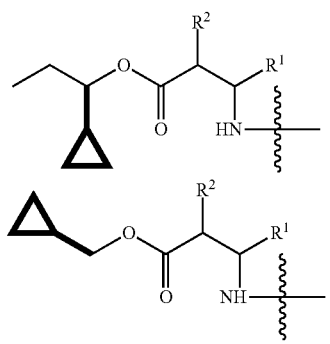

"Spiro-C$_{3-6}$cycloalkyl" refers to a cycloalkyl ring bonded to a non-terminal carbon atom wherein the non-terminal carbon atom is shared with the cycloalkyl group. Spiro-C$_{3-6}$cycloalkyl encompasses each of spino-cyclopropyl, spiro-cyclobutyl, spiro -cyclopentyl and spiro-cyclohexyl. The following is an illustration of a Spiro-C$_{3-6}$cycloalkyl substituent wherein the substituent is spiro-cyclopropyl in bold:

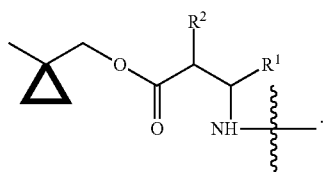

Examples of —C$_{1-5}$alkyl—X—C$_{1-5}$alkyl groups include, but are not limited to, —CH$_2$CH$_2$OCH$_3$, —CH$_2$CH$_2$CH$_2$OCH$_3$, —CH$_2$CH$_2$SCH$_3$, —CH$_2$CH$_2$CH$_2$SCH$_3$, —CH$_2$CH$_2$NHCH$_3$ or —CH$_2$CH$_2$CH$_2$NHCH$_3$.

"Aryl" refers to (i) phenyl, (ii) 9- or 10-membered bicyclic, fused carbocylic ring systems in which at least one ring is aromatic, and (iii) 11- to 14-membered tricyclic, fused carbocyclic ring systems in which at least one ring is aromatic. Suitable aryls include, for example, substituted and unsubstituted phenyl and substituted and unsubstituted naphthyl. An aryl of particular interest is unsubstituted or substituted phenyl.

"Heteroaryl" refers to (i) a 5- or 6-membered heteroaromatic ring containing from 1 to 4 heteroatoms independently selected from N, O and S, wherein each N is optionally in the form of an oxide, and (ii) a 9- or 10-membered bicyclic fused ring system, wherein the fused ring system of (ii) contains from 1 to 6 heteroatoms independently selected from N, O and S, wherein each ring in the fused ring system contains zero, one or more than one heteroatom, at least one ring is aromatic, each N is optionally in the form of an oxide, and each S in a ring which is not aromatic is optionally S(O) or S(O)$_2$. Suitable 5- and 6-membered heteroaromatic rings include, for example, pyridyl, 3-fluoropyridyl, 4-fluoropyridyl, 3-methoxypyridyl, 4-methoxypyridyl, pyrrolyl, pyrazinyl, pyrimidinyl, pyridazinyl, triazinyl, thienyl, furanyl, imidazolyl, pyrazolyl, triazolyl (i.e., 1,2,3-triazolyl or 1,2,4-triazolyl), tetrazolyl, oxazolyl, isooxazolyl, oxadiazolyl (i.e., the 1,2,3-, 1,2,4-, 1,2,5- or 1,3,4-isomer), oxatriazotyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, isoindolyl, benzopiperidinyl, benzofuranyl, imidazo[1,2-a]pyridinyl, benzotria.zolyl, indazolyl, indolinyl, and isoindolinyl. A class of heteroaryls includes unsubstituted or substituted pyridyl or pyrimidyl, and particularly unsubstituted or substituted pyridyl.

The term "heterocyclic ring" refers to (i) a saturated 4- to 7-membered cyclized ring and (ii) an unsaturated, non-aromatic 4 to 7-membered cyclized ring comprised of carbon atoms and 1- 4 heteroatoms independently selected from O, N and S. Heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated, non -aromatic heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond). A class of heterocyclic rings are 4 to 6-membered saturated nionocyclic rings comprised of carbon atoms and 1 or 2 heteroatoms, wherein the heteroatoms are selected from N, O and S. Examples of 4 to 6 membered heterocyclic rings include but are not limited to, azetidinyl, pyrrolidinyl, piperidinyl, piperazinyl, morpholinyl, thiomorpholinyl, tetrahydrofuranyl, tetrahydropyranyl and tetrahydrothiopyranyl, and a sub-class thereof is piperidinyl, pyrrolidinyl, tetrahydrofuranyl or tetrahydropyranyl. The following is an illustration of R$^5$ and R$^6$ when they are joined together to form a heterocyclic ring:

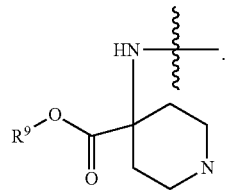

With respect to substituents on a molecule, "geminally" "geminal" refers to two substituents, which may be the same or different, on one carbon.

It is understood that the specific rings and ring systems suitable for use in the present invention are not limited to those listed in the preceding paragraphs. These rings and ring systems are merely representative.

As would be recognized by one of ordinary skill in the art, certain compounds of the present invention maybe able to exist as tautomers, tautomeric forms of these compounds, whether isolated individually or in mixtures, are within the scope of the present invention. For example, in instances where an —OH substituent is permitted on a heteroaromatic ring and keto-enol tautomerism is possible, it is understood that the substituent might in fact be present, in whole or in part, in the oxo (=O) form.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I and its embodiments. For example, certain moieties as defined in Formula I may be unsubstituted or substituted, and the latter is intended to encompass substitution patterns (i.e., number and kind of substituents) that are chemically possible for the moiety and that result in a stable compound.

Each compound of Formula I is comprised of a phosphodiamide amino acid ester having a defined (R) chiral center in the alkyl-ether linking group connecting the nucleobase to the phosphorus as shown in Formula I, and may have one or more additional chiral centers depending on substituent selection. For example, each of Examples 1-52 herein also has an asymmetric phosphorus center. Accordingly, a compound of Formula I may have multiple chiral centers (also referred to as asymmetric or stereogenic centers) This invention encompasses compounds having either the (R) or (S) stereo-configuration at a phosphorus asymmetric center and at any additional asymmetric centers that may be present in a compound of Formula I, as well as stereo-isomeric mixtures thereof.

This invention includes individual diastereomers, particularly epimers, i.e., compounds having the same chemical formula but which differ in the spatial arrangement around a single atom. This invention also includes mixtures of diastereomers, particularly mixtures of epimers, in all ratios. Embodiments of this invention also include a mixture of epimers enriched with 51% or more of one of the epimers, including for example 60% or more, 70% or more, 80% or more, or 90% or more of one epimer. A single epimer is preferred. An individual or single epimer refers to an epimer obtained by chiral synthesis and/or using generally known separation and purification techniques, and which may be 100% of one epimer or may contain small amounts (e.g., 10% or less) of the opposite epimer. Thus, individual diastereomers are a subject of the invention in pure form, both as levorotatory and as dextrorotatory antipodes, in the form of racemates and in the form of mixtures of the two diastereomers in all ratios. In the case of a cis/trans isomerism the invention includes both the cis form and the trans form as well as mixtures of these forms in all ratios.

The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, necessary, with a reagent containing a stereogenic center of known configuration. Alternatively, absolute stereochemistry may be determined by Vibrational Circular Dichroism (VCD) spectroscopy analysis. The present invention includes all such isomers, as well as salts, solvates (which includes hydrates) and solvated salts of such racemates, enantiomers, diastereomers and tautomers and mixtures thereof.

The atoms in a compound of Formula I. may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I; for example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of Formula I can be prepared without undue experimentation by conventional techniques well known to those skilled in the art or by processes analogous to those described in the Schemes and. Examples herein using appropriate isotopically-enriched reagents and/or intermediates.

The compounds can be administered in the form of pharmaceutically acceptable salts. The term "pharmaceutically acceptable salt" refers to a salt which is not biologically or otherwise undesirable (e.g., is neither toxic nor otherwise deleterious to the recipient thereof), Since the compounds of Formula I contain by definition at least one basic group, the invention includes the corresponding pharmaceutically acceptable salts. When the compounds of Formula I contain one or more acidic groups, the invention also includes the corresponding pharmaceutically acceptable salts. Thus, the compounds of Formula I that contain acidic groups (e.g., —COOH) can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids, Compounds of Formula I, which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfatninic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

The instant invention encompasses any composition comprised of a compound of Formula I or a compound that is a salt thereof, including for example but not limited to, a composition comprised of said compound associated together with one or more additional molecular and/or ionic component(s) which may be referred to as a "co-crystal." The term "co-crystal" as used herein refers to a solid phase (which may or may not be crystalline) wherein two or more different molecular and/or ionic components (generally in a stoichiometric ratio) are held together by non-ionic interactions including but not limited to hydrogen-bonding, dipole-dipole interactions, dipole-quadrupole interactions or dispersion forces (van der Waals). There is no proton transfer between the dissimilar components and the solid phase is neither a simple salt nor a solvate. A discussion of co-crystals can be found, e.g., in S. Aitipamula et al., *Crystal Growth and Design,* 2012, 12 (5), pp. 2147-2152.

More specifically with reference to this invention, a co-crystal is comprised of a compound of Formula I or a pharmaceutically acceptable salt thereof, and one or more non-pharmaceutically active component(s) which is not biologically or otherwise undesirable (e.g., is neither toxic nor otherwise deleterious to the recipient thereof). Co -crystals can be obtained from a compound of Formula I, or a pharmaceutically acceptable salt thereof, by customary methods known in the chemical arts. For example, co-crystals comprised of a compound of this invention could be prepared by adding an acid or a neutral molecule at the desired stoichiometry to the compound, adding an appropriate solvent to achieve dissolution and, for example, precipitating, lyophilizing or concentrating the solution to obtain the solid composition. The co-crystal can be, but is not limited to, an embodiment wherein the composition is comprised of a neutral compound (i.e. not a salt form) of Formula I and one or more non-pharmaceutically active component(s); and in a further embodiment, the co-crystal composition is crystalline. Crystalline compositions may be prepared, for example, by adding an acid or a neutral molecule at the desired stoichiometry to the compound of Formula I, adding an appropriate solvent and heating to achieve complete dissolution, and then allowing the solution to cool and the crystals to grow. The present invention also includes all co-crystals of the compounds of this invention which, owing to low physiological compatibility, are not directly suitable for use in pharmaceuticals but which can be used, for example, as intermediates for chemical reactions or for the preparation of pharmaceutically acceptable co-crystals or salts.

Compounds of the present invention may exist in amorphous form and/or one or more crystalline forms, and as such all amorphous and crystalline forms and mixtures thereof of the compounds of Formula I and salts thereof are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the compounds of this invention are likewise encompassed within the scope of the compounds defined by Formula I the pharmaceutically acceptable salts thereof, along with un-solvated and anhydrous forms of such compounds.

Accordingly, the compounds of Formula I, embodiments thereof and specific compounds described and claimed herein encompass all possible pharmaceutically acceptable salts, stereoisomers, tautomers, physical forms (e.g., amorphous and crystalline forms), co-crystal forms, solvate and hydrate forms and any combination of the foregoing forms where such forms are possible.

The compounds of Formula I described herein are prodrugs. A discussion of prodrugs is provided in (a) Stella, V. J.; Borchardt, R. T.; Hageman, M. J.; Oliyai, R.; Maag, H. et al. *Prodrugs: Challenges and Rewards Part* 1 *and Part* 2; Springer, p. 726: New York, N.Y., USA, 2007, (b) Rautio, J.; Kumpulainen, H.; Heimbach, T.; Oliyai, R.; Oh, D. et al. Prodrugs: design and clinical applications. *Nat. Rev. Drug Discov.* 2008, 7, 255, (c) T. Higuchi and V. Stella, *Pro-drugs as Novel Delivery Systems* (1987) 14 of the A.C.S. Symposium Series, and in (d) *Bioreversible Carriers in Drug Design*, (1987) Edward B. Roche, ed., American Pharmaceutical Association and Pergamon Press. More specifically, compounds of Formula I (and pharmaceutically acceptable salts thereof) are prodrug modifications of tenofovir, which is a mono-phosphonate. The compounds of Formula I may be converted intracellularly (in vivo or in vitro) to the corresponding monophosphate or diphosphate of tenofovir. The conversion may occur by one or more mechanisms, e.g., an enzyme-catalyzed chemical reaction, a metabolic chemical reaction, and/or a spontaneous chemical reaction (e.g., solvolysis), such as, for example, through hydrolysis in blood. While not wishing to be bound by any particular theory, tenofovir diphosphate is generally understood to be responsible for inhibiting the HIV RT enzyme and for the resulting antiviral activity after administration of the compound of Formula I to a subject.

Another embodiment of the present invention is a compound of Formula wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as, high performance liquid chromatography, and/or mass spectrometry or NMR techniques. If more than one method of analysis is employed and the methods provide experimentally significant differences in the level of sS purity determined, then the method providing the highest purity level governs. A compound or salt of 100% purity is one which is free of detectable impurities as determined by a standard method of analysis. With respect to a compound of Formula I which has one or more asymmetric centers and can occur as mixtures of stereoisomers, a substantially pure compound can be either a substantially pure mixture of the stereoisomers or a substantially pure individual stereoisomer.

The compounds of Formula I herein, and pharmaceutically acceptable salts thereof, are useful for HIV reverse transcriptase inhibition and for inhibiting HIV replication in vitro and in vivo, More particularly, the compounds of Formula I for inhibiting the polymerase function of HIV-1 reverse transcriptase. The testing of compounds of the Examples of this invention in the Viking assay set forth in Example 53 below, illustrate the ability of compounds of the invention to inhibit the RNA-dependent DNA polymerase activity of HIV-1 reverse transcriptase. The compounds of Formula I may also be useful agents against HIV-2. The compounds of of Examples 1-52 of the present invention may also exhibit activity against drug resistant forms of HIV (e.g., NNRTI-associated mutant strains K103N and/or Y181C; NRTI-associated mutant strains M184V and M184I mutants.

This invention also encompasses methods for the treatment or prophylaxis of infection by HIV, for the inhibition of HIV reverse transcriptase, for the treatment, prophylaxis, or delay in the onset of AIDS in a subject in need thereof, which comprise administering to the subject an effective amount of a compound of the invention or a pharmaceutically acceptable salt thereof.

The invention further encompasses methods for the treatment or prophylaxis of infection by HIV, for the inhibition of HIV reverse transcriptase, for the treatment, prophylaxis, or delay in the onset of AIDS in a subject in need thereof, which comprise administering to the subject an effective amount of a compound of the invention or a pharmaceutically acceptable salt thereof in combination with an effective amount of one or more additional anti-HIV agents selected from the group consisting of HIV antiviral agents, immunomodulators, and anti-infective agents. Within this embodiment, the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors The invention encompasses a pharmaceutical composition comprising an effective amount of a compound of the invention, or a pharmaceutically acceptable salt thereof, and a pharmaceutically acceptable carrier. The invention also encompasses a pharmaceutical composition comprising an effective amount of a compound of the invention, or a pharmaceutically acceptable salt thereof, and a pharmaceutically acceptable carrier further comprising an effective amount of one or more additional anti-HIV agents selected from the group consisting of HIV antiviral agents, immunomodulators, and anti-infective agents. Within this embodiment, the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

The compounds of this invention could also be useful for inhibition of HBV reverse transcriptase. Accordingly, this invention also encompasses methods for the treatment of chronic hepatitis B which comprise administering to the subject an effective amount of a compound of the invention or a pharmaceutically acceptable salt thereof.

The invention also encompasses a compound of the invention, or a pharmaceutically acceptable salt thereof, for use in the preparation of a medicament for the treatment or prophylaxis of infection by HIV, for the inhibition of HIV reverse transcriptase, or for the treatment, prophylaxis, or delay in the onset of AIDS in a subject in need thereof.

Other embodiments of the present invention include the following:

(a) A pharmaceutical composition comprising an effective amount of a compound of Formula I or a pharmaceutically acceptable salt thereof, and a pharmaceutically acceptable carrier.

(b) A pharmaceutical composition which comprises the product prepared by combining (e.g., mixing) an effective amount of a compound of Formula I or a pharmaceutically acceptable salt thereof, and a pharmaceutically acceptable carrier.

(c) The pharmaceutical composition of (a) or (b), further comprising an effective amount of one or more an anti-HIV agents selected from the group consisting of HIV antiviral agents, immunomodulators, and anti-infective agents.

(d) The pharmaceutical composition of (c), wherein the anti-HIV agent is selected from one or more of an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, HIV entry inhibitors and HIV maturation inhibitors.

(e) A combination which is (i) a compound of Formula I or a pharmaceutically acceptable salt thereof and (ii) an anti-HIV agent selected from the group consisting of HIV antiviral agents, immunomodulators, and anti-infective agents; wherein the compound and the anti-HIV agent are each employed in an amount that renders the combination effective for inhibition of HIV reverse transcriptase, for treatment or prophylaxis of infection by HIV, or for treatment, prophylaxis of, or delay in the onset or progression of AIDS.

The combination of (e), wherein the anti-HIV agent is an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, HIV entry inhibitors and HIV maturation inhibitors.

(g) A method for the inhibition of HIV reverse transcriptase in a subject in need thereof which comprises administering to the subject an effective amount of a compound of Formula I or pharmaceutically acceptable salt thereof.

(h) A method for the prophylaxis or treatment of infection by HIV (e.g., HIV-1) in a subject in need thereof which comprises administering to the subject an effective amount of a compound of Formula I or pharmaceutically acceptable salt thereof.

(i) The method of (h), wherein the compound of Formula I or a pharmaceutically acceptable salt thereof is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, HIV entry inhibitors and HIV maturation inhibitors.

(j) A method for the prophylaxis, treatment or delay in the onset or progression of AIDS in a subject in need thereof which comprises administering to the subject an effective amount of a compound of Formula I or pharmaceutically acceptable salt thereof (k) The method of (j), wherein the compound is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, HIV entry inhibitors and HIV maturation inhibitors.

(l) A method for the inhibition of HIV reverse transcriptase in a subject in need thereof which comprises administering to the subject the pharmaceutical composition of (a), (b), (c) or (d) or the combination of (e) or (f).

(m) A method for the prophylaxis or treatment of infection by HIV (e.g., HIV-1) in a subject in need thereof, which comprises administering to the subject the pharmaceutical composition of (a), (b), (c) or (d) or the combination of (e) or (f).

(n) A method for the prophylaxis, treatment, or delay in the onset or progression of AIDS in a subject in need thereof which comprises administering to the subject the pharmaceutical composition of (a), (b), (c) or (d) or the combination of (e) or (f).

The present invention also includes a compound of Formula I or pharmaceutically acceptable salt thereof (i) for use in, (ii) for use as a medicament for, or (iii) for use in the preparation of a medicament for: (a) therapy (e.g., of the human body), (b) medicine, (c) inhibition of HIV reverse transcriptase, (d) treatment or prophylaxis of infection by HIV, or (e) treatment, prophylaxis of, or delay in the onset or progression of AIDS. In these uses, the compounds of the present invention can optionally be employed in combination with one or more anti-HIV agents selected from HIV antiviral agents, anti-infective agents, and immunomodulators.

Additional embodiments of the invention include the pharmaceutical compositions, combinations and methods set forth in (a)-(n) above and the uses (i)(a)-(e) through (iii)(a)-(e) set forth in the preceding paragraph, wherein the compound of the present invention employed therein is a compound of one of the embodiments, aspects, classes, sub-classes, or features described above. In all of these embodiments etc., the compound may optionally be used in the form of a pharmaceutically acceptable salt.

Additional embodiments of the present invention include each of the compounds, pharmaceutical compositions, combinations, methods and uses set forth in the preceding paragraphs, wherein the compound or its salt employed therein is substantially pure. With respect to a pharmaceutical composition comprising a compound of Formula I or its salt and a pharmaceutically acceptable carrier and optionally one or more excipients, it is understood that the term "substantially pure" is in reference to a compound of Formula I or its salt per se.

Still additional embodiments of the present invention include the pharmaceutical compositions, combinations and methods set forth in (a)-(n) above and the uses (i)(a)-(e) through (iii)(a)-(e) set forth above, wherein the HIV of interest is HIV-1. Thus, for example, in the pharmaceutical composition (d), the compound of Formula I is employed in an amount effective against HIV-1 and the anti-HIV agent is an HIV-1 antiviral selected from the group consisting of HIV-1 protease inhibitors, HIV-1 reverse transcriptase inhibitors, HIV-1 integrase inhibitors, HIV-1 fusion inhibitors, HIV-1 entry inhibitors and HIV-1 maturation inhibitors. The compounds of Formula I may also be useful agents against HIV-2.

The term "administration" and variants thereof (e.g., "administering" a compound) in reference to a compound of Fonnula I means providing the compound to the individual in need of treatment or prophylaxis and includes both self-administration and administration to the patient by another person. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients. Ingredients suitable for inclusion in a pharmaceutical composition are pharmaceutically acceptable ingredients, which means the ingredients must be compatible with each other and not deleterious to the recipient thereof.

The term "subject" or "patient" as used herein refers to an animal, preferably a mammal, most preferably a human, who has been the object of treatment, observation or experiment.

The term "effective amount" as used herein means an amount of a compound sufficient to inhibit HIV reverse transcriptase, inhibit HIV replication, exert a prophylactic effect, and/or a exert a therapeutic effect after administration. One embodiment of "effective amount" is a "therapeutically effective amount" which is an amount of a compound that is effective for inhibiting HIV reverse transcriptase, inhibiting HIV replication (either of the foregoing which may also be referred to herein as an "inhibition effective amount"), treating HIV infection, treating AIDS, delaying the onset of AIDS, and/or slowing progression of ARC or AIDS in a patient infected with HIV. Another embodiment of "effective amount" is a "prophylactically effective amount" which is an amount of the compound that is effective for prophylaxis of I-HV infection in a subject not infected with HIV, or prophylaxis of ARC or AIDS in an HIV-infected patient. It is understood that an effective amount can simultaneously be both a therapeutically effective amount, e.g., for treatment of HIV infection, and a prophylactically effective amount, e.g., for prevention or reduction of risk for developing AIDS in a subject infected with HIV. The term "preventing," as used herein with respect to an HIV viral infection or AIDS, refers to reducing the likelihood or severity of HIV infection or AIDS. When the compound of Formula I is administered as a salt, reference to an amount of the compound in milligrams or grams is based on the free form (i.e., the non-salt form) of the compound. In the combination therapies of the present invention, an effective amount can refer to each individual agent or to the combination as a whole, wherein the amounts of all agents administered in the combination are together effective, but wherein a component agent of the combination may or may not be present individually in an effective amount with reference to what is considered effective for that component agent if it were administered alone.

In the method of the present invention (i.e., inhibiting HIV reverse transcriptase, treating or prophylaxis of MV infection, inhibiting HIV replication, treating or prophylaxis of AIDS, delaying the onset of AIDS, or delaying or slowing progression of AIDS), the compounds of this invention, optionally in the form of a salt, can be administered by means that produce contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally (e.g., via tablet or capsule), parenterally (including subcutaneous injections, intravenous, intramuscular or intrasternal injection, or infusion techniques), by inhalation spray, or rectally, in the form of a unit dosage of a pharmaceutical composition containing an effective amount of the compound and conventional non-toxic pharmaceutically acceptable carriers, adjuvants and. vehicles. The compound could also be administered via an implantable drug delivery device adapted to provide an effective amount of the compound or a pharmaceutical composition of the compound over an extended period of time for example, but not limited to, over the course of a month, 3months, 6 months or a year.

Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Liquid preparations suitable for oral administration (e.g., suspensions, syrups, elixirs and the like) can be prepared according to techniques known in the art and can employ any of the usual media such as water, glycols, oils, alcohols and the like.

Parenteral compositions can be prepared according to techniques known in the art and typically employ sterile water as a carrier and optionally other ingredients, such as a solubility aid, Injectable solutions can be prepared according to methods known in the art wherein the carrier comprises a saline solution, a glucose solution or a solution containing a mixture of saline and glucose. Implantable compositions can be prepared according to methods known in the art wherein the carrier comprises the active chemical ingredient with polymers as suitable excipients, or utilizing an implantable device for drug delivery. Further description of methods suitable for use in preparing pharmaceutical compositions for use in the present invention and of ingredients suitable for use in said compositions is provided in Remington's Pharmaceutical Sciences, 18th edition, edited by A. R. Gennaro, Mack Publishing Co., 1990 and in Remington—The Science and Practice of Pharmacy, 22nd Edition, published by Pharmaceutical Press and Philadelphia College of Pharmacy at University of the Sciences, 2012, ISBN 978 0 85711-062-6 and prior editions.

Formulations of compounds described by Formula I that result in drug supersaturation and/or rapid dissolution may be utilized to facilitate oral drug absorption. Formulation approaches to cause drug supersaturation and/or rapid dissolution include, but are not limited to, nanoparticulate systems, amorphous systems, solid solutions, solid dispersions, and lipid systems. Such formulation approaches and techniques for preparing them are known in the art. For example, solid dispersions can be prepared using excipients and processes as described in reviews (e.g., A. T. M. Serajuddin, J Pharm Sci, 88:10, pp. 1058-1066 (1999)). Nanoparticulate systems based on both attrition and direct synthesis have also been described in reviews such as Wu et al (F. Kesisoglou, S. Panmai, Y. Wu, Advanced Drug Delivery Reviews, 59:7 pp. 631-644 (2007)).

The compounds of Formula I can be administered in a dosage range of 0.001 to 1000 mg/kg of mammal (e.g., human) body weight per day, or at longer time intervals on non-consecutive days as appropriate, in a single dose or in divided doses. One example of a dosage range is 0,01 to 500 mg/kg body weight per day, or at other time intervals as appropriate, administered orally or via other routes of administration in a single dose or in divided doses. Another example of a dosage range is 0.1 to 100 mg/kg body weight per day, or at other time intervals as appropriate, administered orally or via other routes of administration in single or divided doses. Another example of a dosage range is 50 mg to 1 gram per day, in a single dose or divided doses.

Daily or weekly administration or less frequent dosing regimens with longer time intervals on non-consecutive days (as discussed below), can be via any suitable route of administration, e.g. but not limited to, oral or parenteral. Daily or weekly administration is preferably via oral administration. For either a daily or weekly dosing regimen, on each day (calendar day or about a 24 hour period of time) of drug administration (the "administration day"), the desired dosage amount may be administered once per administration day or in divided dosage amounts administered at two or more staggered times during the administration day, e.g., a first administration followed about 12 hours later with a second administration during the course of an administration day (the "dosage time(s)"). The desired dosage amount at each of the one or more dosage times on an administration day can be administered via one oral dosage unit such as a tablet, or more than one oral dosage unit as appropriate. Preferably the administration is via a single oral dosage unit, e.g. a tablet, once per administration day.

For weekly or less frequent dosing regimens with longer time intervals on non-consecutive days, a parenteral route of administration may be employed. Examples of dosing regimens with longer time intervals on non-consecutive days include but are not limited to administration weekly (every seventh day with leeway as to exact date of dosing), bi-weekly (every two weeks with leeway as to exact date of dosing), monthly (e.g., every 30 days, or the same calendar day each month with leeway as to exact date of dosing), bimonthly (e.g., every 60 days, or the same calendar day every two months with leeway as to exact date of dosing), every 3 months (e.g., every 90 days, or the same calendar day every three months with leeway as to exact date of dosing), every six months (e.g., every 180 days, or the same calendar day every six months with leeway as to exact date of dosing), or yearly (e.g., every 12 months with leeway as to exact date of the annual dosing). "Leeway" is intended to mean that the dosing regimens described herein also encompasses those wherein the patient generally follows the time intervals between administration days including when the interval is not always strictly followed by the patient, e.g., a weekly dosing regimen where the patient may take the drug product the day before or the day after the seventh day following the prior administration day for one or more weeks. The leeway time may increase as the dosing regimen interval increases. For oral (e.g., tablets or capsules) or other routes of administration, the dosage units may contain 1.0 mg to 1000 mg of the active ingredient, for example but not limited to, 1., 5, 10, 15, 20, 25, 50, 75, 100, 150, 200, 250, 300, 350, 400, 450, 500, 600, 700, 800, 900 or 1000 milligrams of the active ingredient for the symptomatic adjustment of the dosage to the patient to be treated. Furthermore, the compound may be formulated in oral formulations for immediate or modified release such as extended or controlled release.

The favorable pharmacokinetic profile of tested compounds of this invention may also render the the compounds suitable for less frequent dosing. Thus, the compounds of the invention could be administered orally, weekly or parenterally at longer time intervals as described above. For parenteral administration, the compositions can be administered, e.g., intravenously (IV) or intramuscularly (IM) via injection, or using other infusion techniques. One or more of such injections or infusions may be administered at each dosing time interval as needed to deliver the appropriate amount of active agent. The compound. could also be administered parenterally using an implantable device. For parenteral administration including implantable devices employing longer duration dosing intervals such as once monthly, once every 3 months, once every 6 months, once yearly or longer intervals, the dosage amount would be adjusted upward as needed to provide effective treatment during the time intervals between administration of each dose.

The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In some cases, depending on the potency of the compound or the individual response, it may be necessary to deviate upwards or downwards from the given dose. The amount and frequency of administration will be regulated according to the judgment of the attending clinician considering such factors.

As noted above, the present invention is also directed to use of a compound of Formula I with one or more anti-HIV agents. An "anti-HIV agent" is any agent which is directly or indirectly effective in the inhibition of HIV, the treatment or prophylaxis of HIV infection, and/or the treatment, prophylaxis or dday in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows:

TABLE A

Antiviral Agents for Treating HIV infection or AIDS

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | InI |
| doravirine, MK-1439 | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |

TABLE A-continued

Antiviral Agents for Treating HIV infection or AIDS

| Name | Type |
|---|---|
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| Rilpivirine | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tipranavir, Aptivus ® | PI |
| vicriviroc | EI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, delavirdine mesylate, indinavir sulfate, atazanavir sulfate, nelfinavir mesylate, saquinavir mesylate.

It is understood that the scope of combinations of the compounds of this invention with anti-I-IIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the Physicians' Desk Reference, Thomson PDR, Thomson PDR, 57th edition (2003), the 58th edition (2004), or the 59th edition (2005) and the current Physicians' Desk Reference (68th ed.). (2014), Montvale, N.J.: PDR Network. The dosage ranges for a compound of the invention in these combinations can be the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV reverse transcriptase, e.g., by competitive inhibition.

The following non-exclusive list of solvents, reagents, protecting groups, moieties, and other designations may be referred to by their abbreviations:

| | |
|---|---|
| Ac | Acetyl |
| aq | Aqueous |
| AUC | Area under the curve |
| Bu | Butyl |
| Bz | Benzoyl |
| DBU | 1,8-diazabicyclo-[5.4.0]undec-7-ene |
| DCM | dichloromethane |
| DIEA or Hünig's base | N,N-diisopropylethylamine |
| DMF | dimethylformamide |
| DMSO | dimethyl sulfoxide |
| Et | Ethyl |
| EtOH | Ethanol |
| EtOAc | ethyl acetate |
| g | Grams |
| h | Hour |
| HIV | human immunodeficiency virus |
| HPBCD | hydroxypropyl β-cyclodextrin |
| HPLC | high-performance liquid chromatography |

-continued

| | |
|---|---|
| Hz | hertz |
| IPA | isopropanol |
| IV | intravenous |
| iPr | isopropyl |
| L | liter |
| LC | liquid chromatography |
| LC/MS | liquid chromatography mass spectrometry |
| Me | methyl |
| MeOH | methanol |
| mg | milligrams |
| MHz | megahertz |
| min | minute |
| μL | microliters |
| mL | milliliters |
| mmol | millimoles |
| MS | mass spectrometry |
| NHS | normal human serum |
| NMR | nuclear magnetic resonance spectroscopy |
| PBMC | peripheral blood mononuclear cell |
| PE | Petroleum ether |
| Ph | phenyl |
| P.O. | oral |
| Pr | propyl |
| RT or rt | room temperature (ambient, about 25° C.) |
| sat or sat'd | saturated |
| SFC | supercritical fluid chromatography |
| tBu | tert-butyl |
| TEA | triethylamine (Et$_3$N) |
| TFA | trifluoroacetic acid |
| TFV | Tenofovir |
| TFV-MP | Tenofovir monophosphoate |
| TFV-DP | Tenofovir diphosphate |
| THF | tetrahydrofuran |
| TMS | tetramethylsilane |
| UPLC | ultra high pressure liquid chromatography |
| UV | ultraviolet |
| UV/VIS | ultraviolet/visible |

Several methods for preparing the compounds of this invention are described in the following Schemes and Examples. Starting materials and intermediates are purchased or are made using known procedures, or as otherwise illustrated. Some frequently applied routes to the compounds of Formula I are described in the Schemes that follow. In some cases the order of carrying out the reaction steps in the schemes may be varied to facilitate the reaction or to avoid unwanted reaction products.

Several methods for preparing the compounds of this invention are also described in the Examples. Starting materials and intermediates were purchased commercially from common catalog sources or were made using known procedures, or as otherwise illustrated.

SCHEME 1

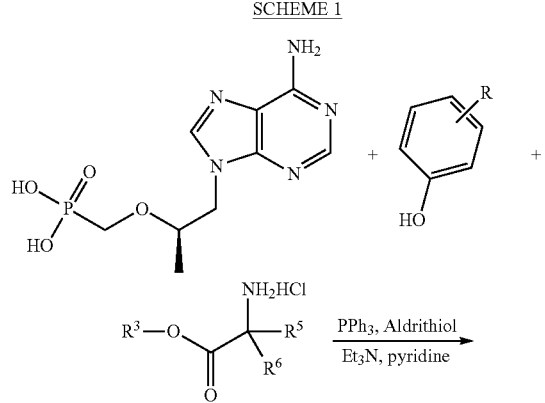

-continued

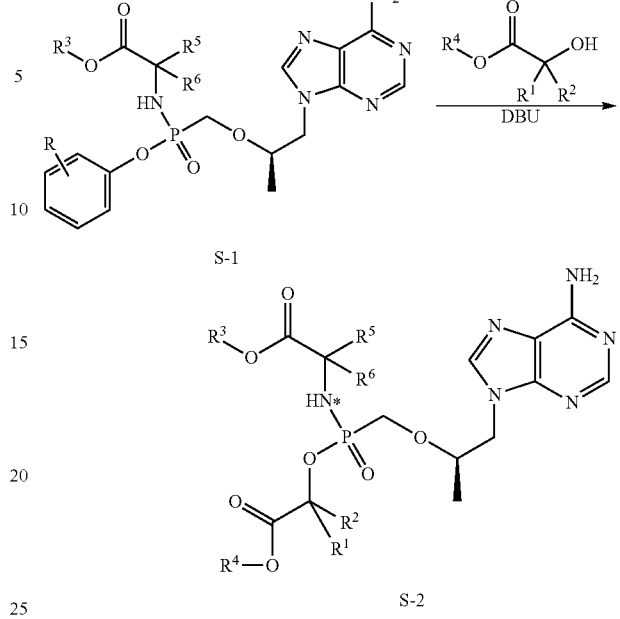

Intermediates compounds of Formula S-1 are prepared from (R)-(((1-(6-amino-9H-purin-9-yl)propan-2-yl)oxy)methyl)phosphonic acid, referred to herein as TFV, with variably-substituted phenols in a one-step one-pot condensation reaction with 2,2'-dipyridyidisulfide (aldrithiol), triphenylphosphine, and base, with p-chlorophenol and m-cyanophenol being preferred. Amino esters that are not commercially available can be readily prepared by condensation between the corresponding amino acid and alcohols with thionyl chloride. The subsequent reaction of S-1 with a corresponding glycolic ester or lactic ester in the presence of DBU base yields the products of Formula S-2 of the present invention.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-MS).

Typically the analytical LC-MS system used consisted of a Waters SQD2 platform with electrospray ionization in positive and negative detection mode with an Acquity UPLC I-class solvent manager, column manager, sample manager and PDA detector. The column for standard method was CORTECS UPLC C18 1.6 μm, 2.1×30 mm, and the column for polar method was ACQUITY UPLC HSST3 1.8 μm, 2.1×30 mm, the column temperature was 40° C., the flow rate was 0.7 mL/min, and injection volume was 1 μL. UV detection was in the range 210-400 nm. The mobile phase consisted of solvent A (water plus 0.05% formic acid) and solvent B (acetonitrile plus 0.05% formic acid) with different gradients for 4 different methods: 1/Starting with 99% solvent A for 0.2 min changing to 98% solvent B over 1 min, maintained for 0.4 min, then reverting to 99% solvent A over 0.1 min; 2/Starting with 99% solvent A for 0.5 min changing to 98% solvent B over 3.7 min, maintained for 0.4 min, then reverting to 99% solvent A over 0.1 min; 3/Starting with 100% solvent A for 0.4 min changing to 98% solvent B over 0.9 min, maintained for 0.3 min, then reverting to 100% solvent A over 0.1 min; 4/Starting with 100% solvent A for 0.8 min changing to 98% solvent B over 3.4 min, maintained for 0.4 min, then reverting to 100% solvent A over 0.1 min.

Preparative HPLC purifications were usually performed using a mass spectrometry directed system. Usually they were performed on a Waters Chromatography Workstation (MassLynx V4.1) configured with LC-MS System Consisting of: Waters ZQ™ 2000 (quad MS system with Electrospray Ionization), Waters 2545 Gradient Pump, Waters 2767 Injecto/Collector, Waters 2998 PDA Detector, the MS Conditions of: 100-1400 amu, Positive Electrospray, Collection Triggered by MS, and a Waters SUNFIRE® C-18 5 micron, 19 mm (id)×150 mm column. The mobile phases consisted of mixtures of acetonitrile (5-95%) in water containing 0.02% HCOOH. Flow rates were maintained at 20 mL/min, the injection volume was 500 to 3000 μL, and the UV detection range was 210-400 nm. Mobile phase gradients were optimized for the individual compounds. Preparative HPLC were also performed on a Gilson system 233XL WITH 735 (Unipoint). The column was a Waters XBridge Prep C18 5 μm OBD, dimension 30×250 mm. The mobile phase consisted of mixture of acetonitrile/ammonium carbonate 0.02N (20-50% in 59 min). How rates were maintained at 30 mL/min, the injection volume was 1000 μL, and the UV detection range was 260 nm. Reactions performed using microwave irradiation were normally carried out using an Emrys Optimizer manufactured by Personal Chemistry, or an Initiator manufactured by Biotage. Concentration of solutions was carried out on a rotary evaporator under reduced pressure. Flash chromatography was usually performed using a Biotage® Flash Chromatography apparatus (bolero) on silica gel (15-45μ, 40-63μ, or spheric silica) in pre-packed cartridges of the size noted. $^1$H NMR. spectra were acquired at 400 MHz or 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). Chiral analytical chromatography was performed on one of CHIRALPAK® AS, CHIRALPAK® AD, CHIRALCEL® OD, CHIRALCEL® IA, or CHIRALCEL® OJ columns (250×4.6 mm) (Daicel Chemical Industries, Ltd.) with noted percentage of either ethanol in hexane (%Et/Hex) or isopropanol in heptane (%IPA/Hep) as isocratic solvent systems. Chiral preparative chromatography was conducted on one of of CHIRALPAK AS, of CHIRALPAK AD, CHIRALCEL® OD, CHIRALCEL® IA, CHIRALCEL® OJ columns (20×250 mm) (Daicel Chemical Industries, Ltd.) with desired isocratic solvent systems identified on chiral analytical chromatography or by supercritical fluid (SFC) conditions.

It is understood that a chiral center in a compound may exist in the "S" or "R" stereoconfiguration, or as a mixture of both. Within a molecule, each bond drawn as a straight line from a chiral center includes both the (R) and (S) stereoisomers as well as mixtures thereof.

The compounds of Formula I herein including those in Examples 1-52 contain a phosphorus chiral center. The isomer mixture in each of Examples 1-19, were separated, providing an Isomer #A, e.g., Isomer 1A (faster eluting isomer) and an Isomer #B, e.g., Isomer 1B (slower eluting isomer), based on their observed elution order resulting from the separation as performed in the Example. Where retention times are shown, they are provided only to show the relative order of elution of each isomer in an Example; a retention time does not represent an immutable characteristic of the isomer with which it is associated. Elution order of separated isomers may differ if performed under conditions different than those employed herein. Absolute stereochemistry (R or S) of the phosphorus chiral center in each of the "A" and "B" stereoisomers in Examples 1 to 19 was not determined. An asterisk (*) may be used in the associated chemical str e drawings of the Example compounds to indicate the phosphorus chiral center.

INTERMEDIATE A

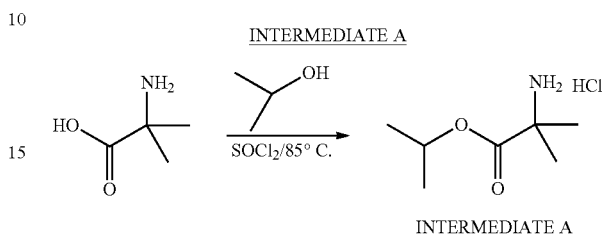

INTERMEDIATE A

Isopropyl 2-amino-2-methylpropanoate hydrochloride: Thionyl chloride (24.2 g, 204 mmol) was added dropwise to a solution of 2-amino-2-methylpropanoic acid (7 g, 67.9 mmol) in propan-2-ol (250 mL) at rt. The mixture was heated at 85° C. (reflux) for 5 days. The resulting clear solution was concentrated under reduced pressure to give a residue, which was triturated with diethyl ether and pentane to afford the title compound: $^1$H NMR (400 MHz, DMSO-d$_6$) δ 8.55 (brs, 3H), 4.98 (heptuplet, J=6.25 Hz, 1H), 1.45 (s, 6H), 1.44 (s, 1H), 1.24 (d, J=6.25 Hz, 6H).

INTERMEDIATE B

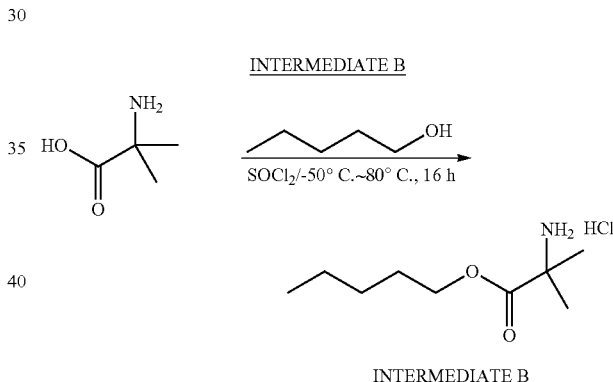

INTERMEDIATE B

Pentyl 2-amino-2-methylpropanoate hydrochloride: Thionyl chloride (34.6 g, 291 mmol) was added dropwise to a solution of 2-amino-2-methylpropanoic acid (10 g, 97 mmol) in pentan-1-ol (200 mL) at −50° C. The mixture was allowed to warm to ambient temperature, and then heated at 80° C. for 16 hours. The resulting mixture was concentrated under reduced pressure to give a residue, which was triturated with ice-cold diethyl ether to afford the title compound: LC/MS: [(M-HCl+1)]$^+$=174.0.

INTERMEDIATE C

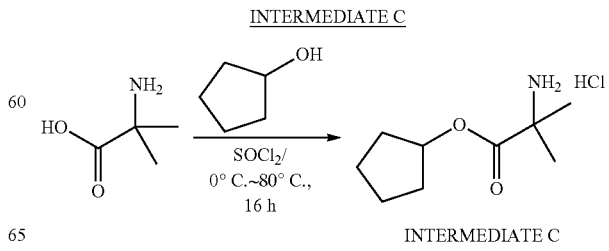

INTERMEDIATE C

Cyclopentyl 2-amino-2methylpropanoate hydrochloride: Thionyl Chloride (3.87 mL, 53.3 mmol) was added dropwise to a stirred solution of 2-amino-2-methylpropanoic acid (5 g, 48.5 mmol) in cyclopentanol (26.4 ml, 291 mmol) at 0° C. The mixture was stirred at 80° C. for 16 hours. The reaction mixture was cooled, diluted with water (60 mL) and washed with DCM (2×80 mL). The aqueous layer was concentrated under reduced pressure to afford the title compound: $^1$H NMR (400 MHz, dMSO-$d_6$) δ 8.61 (brs, 3H), 5.19-5.15 (m, 1H), 1.87-1.81 (m, 2H) 1.72-1.55 (m, 6H), 1.45 (s, 6H).

INTERMEDIATE D

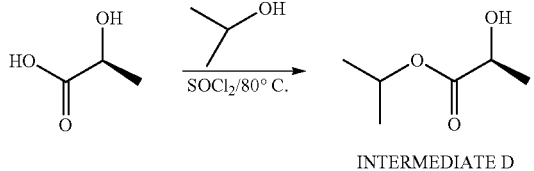

INTERMEDIATE D

Isopropyl (S)-2-hydroxypropanoate: Thionyl chloride (5.4 g, 45.4 mmol) was added dropwise to a solution of (S)-2-hydroxypropanoic acid (2 g, 22.2 mmol) in propan-2-ol (15 mL) at rt. The mixture was heated at 80° C. under microwaves irradiations for 2 hours. The resulting solution was concentrated under reduced pressure to give a residue, which was dissolved in EtOAc and washed with sat. aqueous sodium hydrogenocarbonate solution. The combined organic layers were dried, filtered and concentrated under reduced pressure to afford the title compound: $^1$H NMR (400 MHz, DMSO-$d_6$) δ 5.28 (d, J=5.73 Hz, 1H), 4.90 (heptuplet, J=6.30 Hz, 1H), 4.10-4.04 (m, 1H), 1.23-1.18 (m, 9H).

INTERMEDIATE E

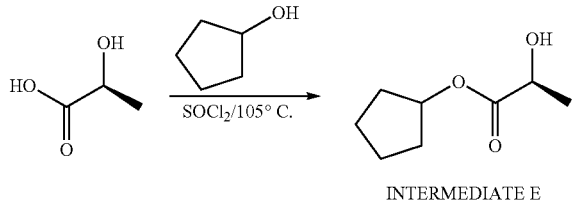

INTERMEDIATE E

Cyclopentyl (S),-hydroxypropanoate: Thionyl chloride (42.3 g, 355 mmol) was added dropwise to a solution of (S)-2-hydroxypropanoic acid (16 g, 178 mmol) in cyclopentanol (120 mL) at rt. The reaction mixture was heated at 105° C. for 2 hours and under microwaves irradiations for 45 minutes. The resulting solution was concentrated under reduced pressure to give a residue, which was dissolved in EtOAc and washed with sat. aqueous sodium hydrogenocarbonate solution and brine. The combined organic layers were dried, filtered and concentrated under reduced pressure. The residue was distilled under high vacuum at 50° C.-100° C. to afford the title compound: $^1$H NMR (400 MHz, CDCl$_3$) δ 5.27-5.24 (m, 1H), 4.22 (q, J=6.86 Hz, 1H), 2.80 (brs, 1H), 1.91-1.47 (m, 8H), 1.40-1.38 (m, 3H).

INTERMEDIATE F

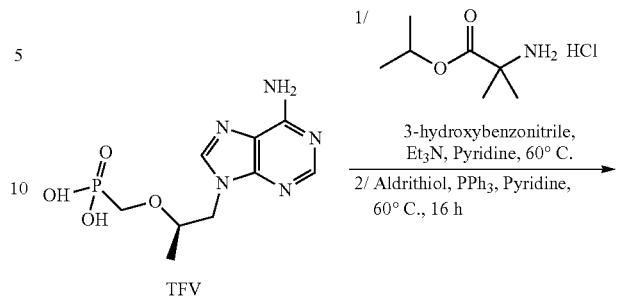

Isopropyl 2-((((((R)-1-(6-amino-9H-purin-9-yl)propan-2-yl)oxy)methyl)(3-cyanophenoxy)phosphoryl)amino)-2-methyluropanoate: To a mixture of (R)-(((1-(6-amino -9H-purin-9-yl)propan-2-yl)oxy)methyl)phosphonic acid (referred to herein as TFV, 3.5 g, 12.19 mmol), 3-hydroxybenzonitrile (7.26 g, 60.9 mmol), INTERMEDIATE A (4.43 g, 24.37 mmol) and triethylamine (14.80 g, 146 mmol) in pyridine (42 mL) heated at 60° C. for 5 min was added a freshly prepared solution of 1,2-di(pyridin-2-yl)disulfane (Aldrithiol, 18.79 g, 85 mmol) and triphenylphosphine (22.37 g, 85 mmol) in pyridine (42 mL), The reaction mixture was stirred at 60° C. overnight, cooled to rt, and concentrated under reduced pressure. The crude residue was partitioned between EtOAc and an aqueous saturated NaHCO$_3$ solution. The organic layer was washed with brine, dried and concentrated under reduced pressure. The crude residue was purified by flash chromatography on silica gel (DCM/EtOH: 0 to 20%) to afford the title compound as a diastereomeric mixture: $^{31}$P NMR (162 MHZ, DMSO-$d_6$) δ 22.83 (s, 0.6P), 22.77 (s, 0.4P); LC/MS: [(M+1)]$^+$=516.5.

INTERMEDIATE G

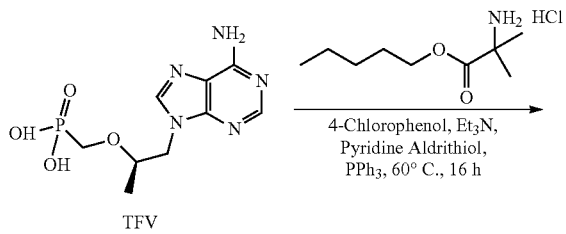

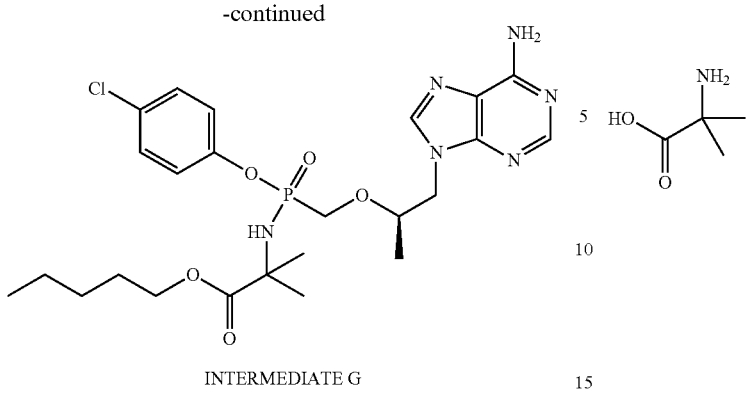

INTERMEDIATE G

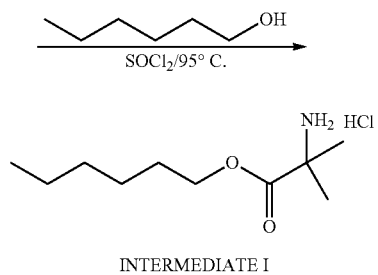

INTERMEDIATE I

Pentyl 2-((((((R)-1-(6-amino-9H-purin-9-yl)propan-2-yl)oxy)methyl)(4-chlorophenoxy)phosphoryl)amino)-2-methylpropanoate: To a mixture of (R)-(((1-(6-amino -9H-purin-9-yl)propan-2-yl)oxy)methyl)phosphonic acid (referred to herein as TFV, 14.6 g, 50.8 mmol), INTERMEDIATE B (10.6 g, 50.8 mmol), 4-chlorophenol (13.1 g, 102 mmol), and triethylamine (51.3 g, 508 mmol) in pyridine (500 mL) were added triphenylphosphine (53.3 g, 203 mmol) and 1,2-di(pyridin-2-yl)disulfane (Aldrithiol, 44.8 g, 203 mmol). The reaction mixture was stirred for 16 hours at 60° C. under nitrogen atmosphere. After cooling down to ambient temperature, the resulting mixture was concentrated under reduced pressure and the residue was purified by silica gel column chromatography DCM/MeOH:

2% to 10%) to afford the title compound: LC/MS: [(M+1)]$^+$=553.2.

Hexyl 2-amino-2-methylpropanoate hydrochloride: INTERMEDIATE I was prepared in a similar fashion to that described for the synthesis of INTERMEDIATE A starting from 2-amino-2-methylpropanoic acid in hexan-1-ol: $^1$H NMR. (400 MHz, DMSO-d$_6$) δ 8.75 (brs, 3H), 4.15 (t, J=6.48 Hz, 2H), 1.65-1.57 (m, 2H), 1.49 (s, 6H), 1.37-1.25 (m, 6H), 0.88-0.85 (m, 3H).

INTERMEDIATE J

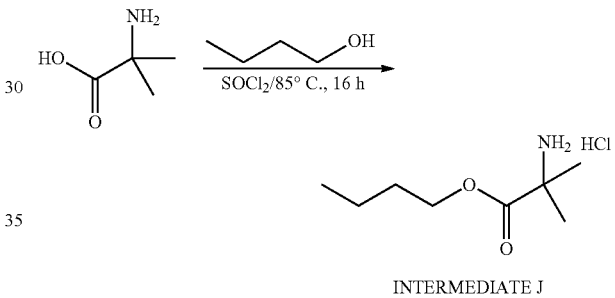

INTERMEDIATE J

INTERMEDIATE H

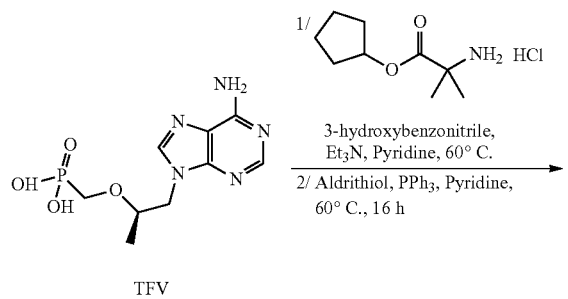

TFV

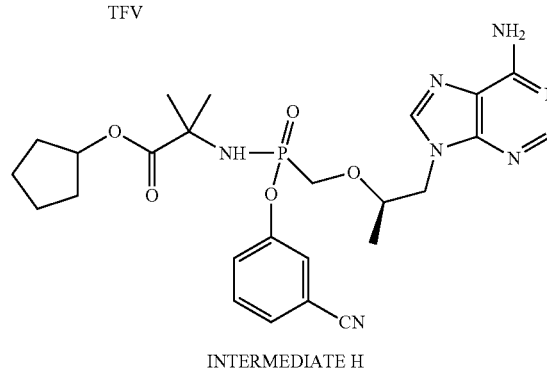

INTERMEDIATE H

Butyl 2-amino-2-methylpropanoate hydrochloride: INTERMEDIATE J was prepared in a similar fashion to that described for the synthesis of INTERMEDIATE A starting from 2-amino-2-methylpropanoic acid in 1-butanol: $^1$H NMR (400 Hz, DMSO-d$_6$) δ 8.63 (brs, 3H), 4.17 (t, J=6.44 Hz, 2H), 1.64-1.57 (m, 2H), 1.48 (s, 6H), 1.44-1.31 (m, 2H), 0.9 (t, J=7.39Hz, 3H).

INTERMEDIATE K

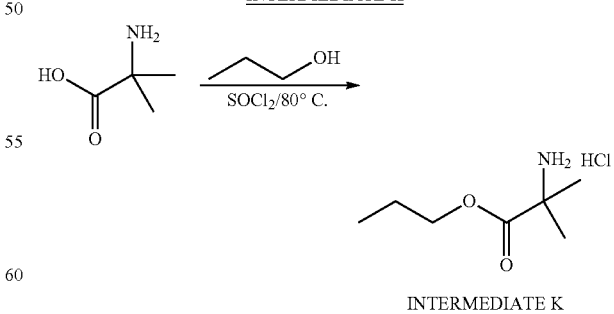

INTERMEDIATE K

Cyclopentyl 2-((((((R)-1-(6-amino-9H-purin-9-yl)propan-2-yl)oxy)methyl)(3-cyanophenoxy phosphoryl)amino)-2-methylpropanoate: INTERMEDIATE H was prepared in a similar fashion to that described for the synthesis of INTERMEDIATE F starting from TFV with INTERMEDIATE C: LC/MS: [(M+1)]$^+$=542.6.

Propyl 2-amino-2-methylpropanoate hydrochloride: INTERMEDIATE K was prepared in a similar fashion to that described for the synthesis of :INTERMEDIATE A starting from 2-amino-2-methylpropanoic acid in propan-1- ol: $^1$H NMR (400 MHz, DMSO-d$_6$) δ 8.66 (brs, 3H), 4.13 (t, J=6.44 Hz, 2H), 1.68-1.59 (m, 2H), 1.49 (s, 6H), 0.91 (t, J=7.49 Hz, 3H).

INTERMEDIATE L

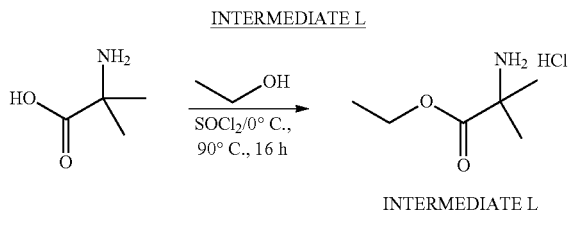

INTERMEDIATE L

Ethyl 2-amino-2-methylpropanoate hydrochloride: INTERMEDIATE L was prepared in a similar fashion to that described for the synthesis of INTERMEDIATE C starting from 2-amino-2-methylpropanoic acid in ethanol and worked-up in a similar fashion to that described for INTERMEDIATE A: $^1$H NMR (400 MHz, DMSO-d$_6$) δ 8.75 (brs, 3H), 4.20 (q, J=7.06 Hz, 2H), 1.49 (s, 6H), 1.23 (t, J=7.06 Hz, 3H).

INTERMEDIATE M

INTERMEDIATE M

Isobutyl 2-amino-2-methylpropanoate hydrochloride: INTERMEDIATE M was prepared in a similar fashion to that described for the synthesis of INTERMEDIATE A starting from 2-amino-2-methylpropanoic acid in isobutanol: $^1$NMR (400 MHz, DMSO-d$_6$) δ 8.69 (brs, 3H), 3.96 (d, J=6.37 Hz, 2H), 1.93 (heptuplet, J=6.62 Hz, 1H), 1.50 (s, 6H), 0.92 (d, J=6.62 Hz, 6H).

INTERMEDIATE N

INTERMEDIATE N

Cyclohexyl 2-amino-2-methylpropanoate hydrochloride: INTERMEDIATE N was prepared in a similar fashion to that described for the synthesis of INTERMEDIATE A starting from 2-amino-2-methylpropanoic acid in cyclohexanol (the residue was triturated twice): $^1$H NMR (400 MHz, DMSO-d$_6$) δ 8.47 (brs, 3H), 4.83-4.78 (m, 1H), 1.80-1.74 (m, 2H), 1.70-1.63 (m, 2H), 1.53-1.29 (m, 12H).

INTERMEDIATE O

INTERMEDIATE O

Cyclobutyl 2-amino-2-methylpropanoate hydrochloride: To a stirred solution of cyclobutanol (5.03 g, 69.8 mmol) at rt thionyl chloride (1.52 g, 53.3 mmol) was added dropwise, followed by 2-amino-2-methylpropanoic acid (1.2 g, 11.64 mmol). The reaction mixture was capped and stirred at 80° C. for 2 days. The reaction mixture was cooled, partitioned between DCM (40 mL) and water (30 mL). The aqueous layer was washed with DCM (40 mL), concentrated azeotroping with ACN, and dried under high pressure. The resulting solid was washed with diethyl ether to afford the title compound: $^1$H NMR (400 MHz, dMSO-d$_6$) δ 8.70 (brs, 3H), 4.99 (quintuplet, J=7.38 Hz, 1H), 2.35-2.27 (m, 2H), 2.12-2.02 (m, 2H), 1.83-1.74 (m, 1H), 1.69-1.57 (m, 1H), 1.48 (s, 6H).

INTERMEDIATE P

INTERMEDIATE P

Benzyl 2-amino-2-methylpropanoate hydrochloride: A mixture of 2-amino-2-methylpropanoic acid (3 g, 29.1 mmol), benzyl alcohol (12 mL, 115 mmol) and p-toluenesulfonic acid monohydrate (5.53 g, 29.1 mmol) in toluene (40 mL) was heated under reflux overnight. Additional benzyl alcohol (12 mL, 115 mmol) was added and the reaction mixture was heated with a Dean Starck overnight. The reaction mixture was concentrated under reduced pressure and washed with diethyl ether. Diethyl ether was removed, and then the residue was dissolved in ethyl acetate and washed with a saturated aqueous NaHCO$_3$ solution. The organic layer was dried over Na$_2$SO$_4$ and concentrated under reduced pressure. The resulting oil was triturated with diethyl ether and HCl in dioxane. The resulting solid was filtered, washed with diethyl ether and dried under reduced pressure to afford the title compound: $^1$H NMR (400 MHz, dMSO-d$_6$) δ 8.54 (brs, 3H), 7.42-7.35 (m, 5H), 5.25 (s, 2H), 1.49 (s, 6H).

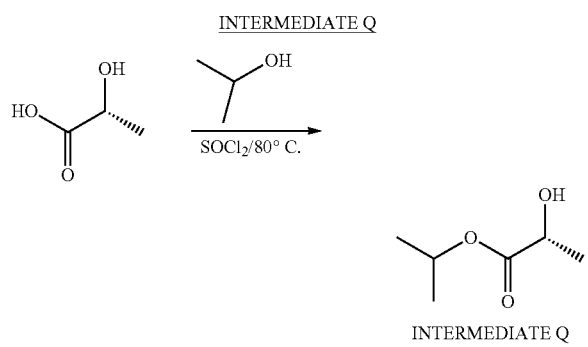

INTERMEDIATE Q

Isopropyl (R)-2-hydroxypropanoate: INTERMEDIATE Q was prepared in a similar fashion to that described for the synthesis of INTERMEDIATE D starting from (R)-2-hydroxypropanoic acid in propan-2-ol: $^1$H NMR (400 MHz, DMSO-d$_6$) δ 5.27 (d, J=5.82 Hz, 1H), 4.91 (heptuplet, J=6.22 Hz, 1H), 4.11-4.01 (m, 1H), 1.24-1.18 (m, 9H).

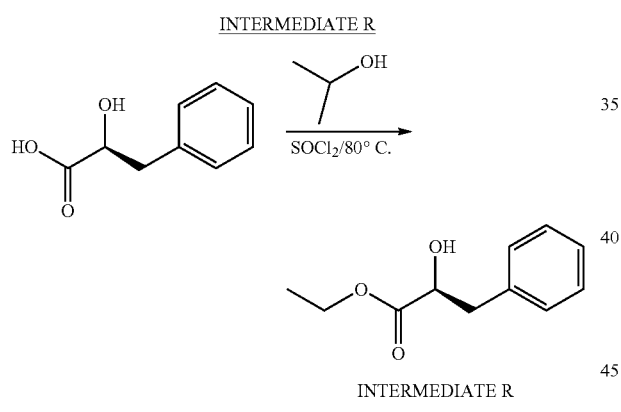

INTERMEDIATE R

Isopropyl (S)-2-hydroxy-3-phertyJpropanoate: INTERMEDIATE R was prepared in a similar fashion to that described for the synthesis of INTERMEDIATE starting from (S) -2-hydroxy-3-phenylpropanoic acid in propan-2-ol: $^1$H NMR (400 MHz, DMSO-d$_6$) δ 7.28-7.17 (m, 5H), 5.48 (d, J=6.15 Hz, 1H), 4.86 (heptuplet, J=6.21 Hz, 1H), 4.21-4.16 (m, 1H), 2.92 (dd, J=13.64 Hz, 5.65 Hz, 1H), 2.83 (dd, J=13.64 Hz, 7.71 Hz, 1H), 1.16 (d, J=6.21 Hz, 3H), 1.08 (d, J=6.21 Hz, 3H).

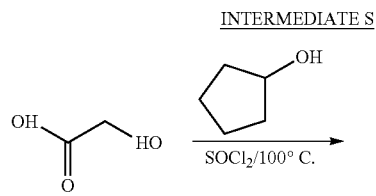

INTERMEDIATE S

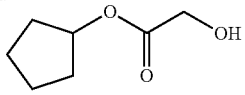

INTERMEDIATE S

Cyclopentyl 2-hydroxyacetate: INTERMEDIATE S was prepared in a similar fashion to that described for the synthesis of INTERMEDIATE D starting from glycolic acid in cyclopentanol. The reaction was carried out at 100° C. The obtained oil was distilled to afford the title compound: $^1$H NMR (400 MHz, CDCl$_3$) δ 5.30-5.26 (m, 1H), 4.11 (s, 2H), 2.80 (s, 1H), 1.95-1.84 (m, 2H), 1.77-1.68 (m, 4H), 1.64-1.56 (m, 2H).

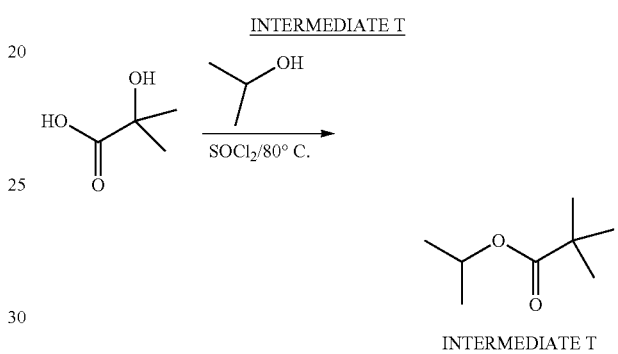

INTERMEDIATE T

Isopropyl 2-hydroxy-2-methylpropanoate: INTERMEDIATE T was prepared in a similar fashion to that described for the synthesis of INTERMEDIATE D starting from 2-hydroxy -2-methylpropanoic acid in propan-2-ol: $^1$H NMR (400 MHz, DMSO-d$_6$) δ 5.14 (s, 1H), 4.88 (heptuplet, J=6.27 Hz, 1H), 1.27 (s, 6H), 1.19 (d, J=6.27 Hz, 6H).

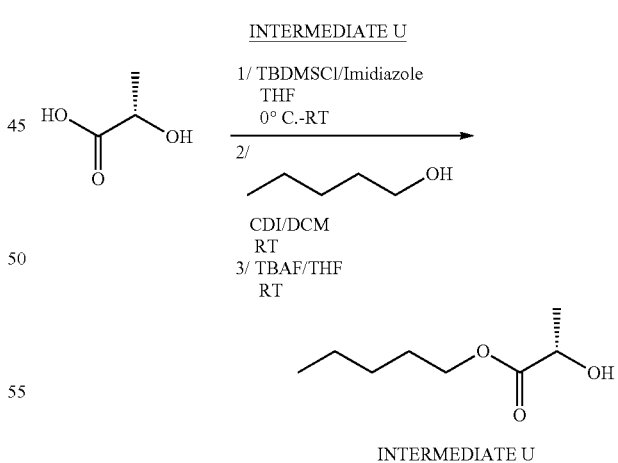

INTERMEDIATE U

Pentyl (S)-2-hydroxypropanoate: Step 1: To a solution of (S)-2-hydroxypropanoic acid (0.90 g, 9.99 mmol) in THF (20 mL) were added tert-butylchlorodimethylsilane (3.31 g, 21.98 mmol) and imidazole (1.63 g, 23.98 mmol) at 0° C. The resulting mixture was stirred for 4 hours at ambient temperature and diluted with water (50 mL). The resulting mixture was acidified with HCl (24 mL, 1 M in water), extracted with EtOAc (3×40 mL) and washed with brine (50 mL). The combined organic layers was dried over anhydrous sodium sulfate and filtered. The filtrate was concentrated under reduced pressure to afford the title intermediate: $^1$H NMR (300 MHz, CDCl$_3$) δ 4.37 (q, J=6.9 Hz, 1H), 1.45 (d, J=6.9 Hz, 3H), 0.93 (s, 9H), 0.15 (s, 6H). Step 2: To a solution of (S)-2-((tert-butyldimethylsilyl)oxy)propanoic acid (0.50 g, 2.45 mmol) in DCM (20 mL) was added N,N'-carbonyldiimidazole (0.59 g, 3.67 mmol) followed by the addition of pentan-1-ol (0.32 g, 3.67 mmol). The resulting mixture was stirred for 16 hours at ambient temperature. The reaction was quenched with water (100 mL) and the resulting mixture was extracted with EtOAc (3×50 mL). The combined organic layers was washed with brine (2×50 mL), dried over anhydrous sodium sulfate and filtered. The filtrate was concentrated under reduced pressure and the residue was purified by silica gel column chromatography (PE/EtOAc: 3% to 10%) to afford the title intermediate: $^1$H NMR (300 MHz, CDCl$_3$) δ 4.32 (q, J=6.9 Hz, 1H), 4.15-4.06 (m, 2H), 1.68-1.64 (m, 2H), 1.39 (d, J=6.6 Hz, 3H), 1.36-1.25 (m, 4H), 0.92-0.89 (m, 3H), 0.89 (s, 9H), 0.12 (s, 3H), 0.09 (s, 3H). Step 3: A solution of (S)-pentyl 2-((tert-butyldimethylsilyl)oxy)propanoate (1.16 g, 4.24 mmol) in THF (20 mL) was treated. with tetrabutylarnmonium fluoride (1.66 g, 6.35 mmol) for 2 hours at ambient temperature. The reaction was quenched with water (100 mL) and the resulting mixture was extracted with EtOAc (3×50 mL). The combined organic layers was washed with brine (2×50 mL), dried over anhydrous sodium sulfate and filtered. The filtrate was concentrated under reduced pressure and the residue was purified by silica gel column chromatography (PE/EtOAc: 3% to 10%) to afford the title compound: $^1$H NMR (300 MHz, CDCl$_3$) δ 4.30 (q, J=6.9 Hz, 1H), 4.19-4.15 (m, 2H), 2.80 (d, J=4.2 Hz, 1H), 1.69-1.65 (m, 2H), 1.39 (d, J=7.2 Hz, 3H), 1.35-1.29 (m, 4H), 0.92-0.89 (m, 3H).

INTERMEDIATE V

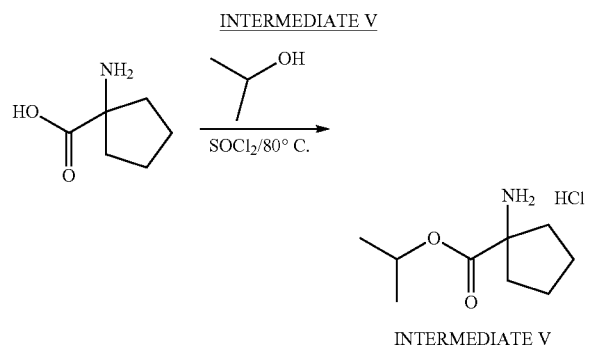

INTERMEDIATE V

Isopropyl 1-aminocyclopentane-1-carboxylate hydrochloride: INTERMEDIATE V was prepared in a similar fashion to that described for the synthesis of INTERMEDIATE D starting from cycloleucine in propan-2-ol. The crude residue was triturated in PE/diisopropyl ether mixture to afford the title compound: $^1$H NMR (400 MHz, DMSO-d$_6$) δ 8.61 (brs, 3H), 4.98 (heptuplet, J=6.26 Hz, 1H), 2.13-2.05 (m, 2H), 1.93-1.70 (m, 6H), 1.24 (d, J=6.26 Hz, 6H).

INTERMEDIATE W

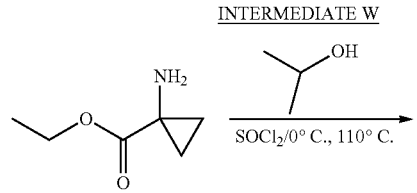

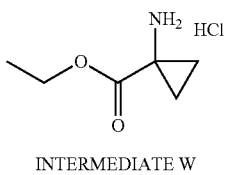

INTERMEDIATE W

Isopropyl 1-aminocyclopropane-1-carboxylate hydrochloride: Thionyl chloride (3.26 g, 27.4 mmol) was added dropwise to a solution of ethyl 1-aminocyclopropane-1-carboxylate (2 g, 11.8 mmol) in propan-2-ol (8 mL) at 0° C. The mixture was heated at 110° C. for 16 hours. The resulting solution was concentrated under reduced pressure to afford the title compound: $^1$H NMR (400 MHz, DMSO-d$_6$) δ 9.01-8.87 (m, 3H), 4.95 (heptuplet, J=6.19 Hz, 1H), 1.47-1.33 (m, 4H), 1.21 (d, J=6.19Hz, 6H).

INTERMEDIATE X

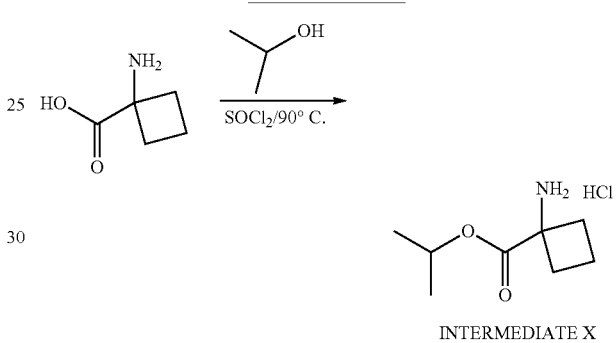

INTERMEDIATE X

Isopropyl 1-aminocyclobutane-1-carboxylate hydrochloride: INTERMEDIATE X was prepared in a similar fashion to that described for the synthesis of INTERMEDIATE A starting from 1-aminocyclobutanecarboxylic acid in propan-2-ol for 16 hours. The crude residue was triturated in diethyl ether to afford the title compound: $^1$H NMR (400 MHz, DMSO-d$_6$) δ 8.88 (brs, 3H), 5.02 (heptuplet, J=6.22 Hz, 1H), 2.48-2.41 (m, 4H), 2.10-1.97 (m, 2H), 1.28 (d, J=6.22 Hz, 6H).

INTERMEDIATE Y

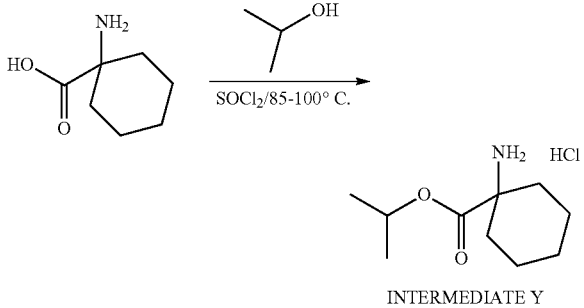

INTERMEDIATE Y

Isopropyl 1-aminocyclohexane-1-carboxylate hydrochloride: Thionyl chloride (14.93 g, 125 mmol) was added dropwise to a solution of 1-aminocyclohexanecarboxylic acid (8 g, 55.9 mmol) in propan-2-ol (250 mL). The reaction mixture was heated at 85° C. for 16 hours. Thionyl chloride (7.19 g, 60.5 mmol) was added and the mixture was heated at 90° C. for additional 16 hours. Thionyl chloride (4.91 g, 41.2. mmol) was added and the mixture was heated at 100° C. for additional 16 hours. The reaction mixture was concentrated under reduce to give a residue which was triturated with diethyl ether to afford the title compound: $^1$H NMR (400 MHz, DMSO-d$_6$) δ 8.58 (brs, 3H), 4.99 (heptuplet, J=6.21 Hz, 1H), 1.97-1.90 (m, 2H), 1.78-1.72 (m, 2H), 1.69-1.59 (m, 2H), 1.58-1.49 (m, 2H), 1.45-1.37 (m, 2H), 1.25 (d, J=6.21 Hz, 6H).

EXAMPLE 1

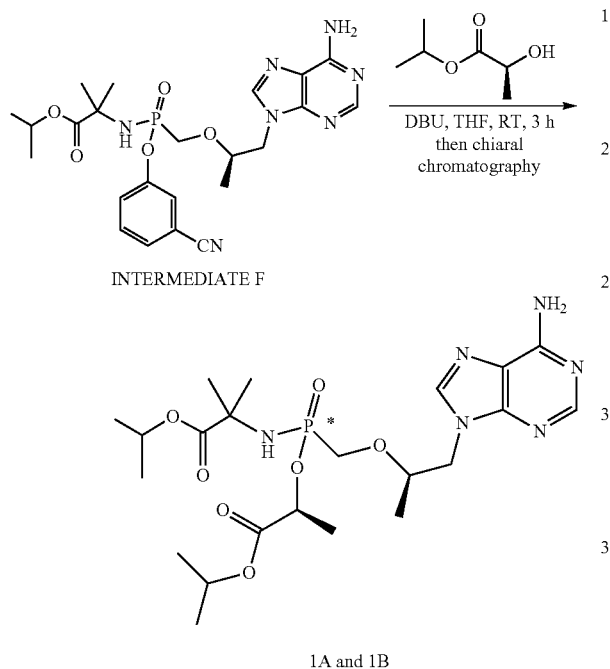

INTERMEDIATE F 1A and 1B

Step 1: Isopropyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate: To a stirred mixture of INTERMFDIATE F (3.5 g, 6.79 mmol) and INTERMEDIATE D (1.79 g, 13.58 mmol) in THF (20 mL) was added DBU (1.53 mL, 10.18 mmol) at rt. The reaction mixture was stirred at RT for 3 hours and then, concentrated under reduced pressure. The crude residue was purified twice by flash chromatography on silica gel (DCM/MeOH: 0 to 10%) to afford the title compound as a mixture of diastereoisomers: $^{31}$P NMR (162 MHz, CDCl$_3$) d 24.78 (s, 0.4P), 24.60 (s, 0.6P); LC/MS: [(M+1)]$^+$=529.2.

Step 2: Isopropyl 2-(((S)-((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate; and isopropyl 2-(((R)-((((R)-1-(6-amino-9H-purin-9-yl)propan-2-yl)oxy)methyl)(((S)-1-isopropoxy-1-oxyopropan-2-yl)oxy)phosphoryl)amino)-2-methylpropanoate (1A and 1B):

The isomers were separated by preparative chiral SFC with the following conditions: Column: ID 2*25 cm; Mobile Phase A: CO$_2$: 70%, Mobile Phase B: IPA (HPLC grade): 30%; Flow rate: 60 mL/min; Detector 220 nm; to afford: Isomer IA (faster eluting): $^1$H NMR (600 MHz, CDCl$_3$) δ 8.33 (s, 1H), 8.10 (s, 1H), 5.98 (brs, 2H), 5.11 (p, J=6.3 Hz, 1H), 5.05-4.94 (m, 2H), 4.39 (dd, J=14.5 Hz, 2.9 Hz, 1H), 4.16 (dd, J=14.4 Hz, 7.5 Hz, 1H), 3.94 (ddd, J=7.4 Hz, 6.1 Hz, 2.9 Hz, 1H), 3.90-3.80 (m, 2H), 3.60 (dd, J=13.1 Hz, 9.7 Hz, 1H), 1.53 (d, J=7.0 Hz, 3H), 1.45 (s, 3H), 1.43 (s, 3H), 1.31-1.19 (m, 15H); $^{31}$P NMR (243 MHz; CDCl$_3$) δ 24.687; LC/MS [(M+1)]$^+$=529.4; and Isomer 1B (slower eluting).

Isomer 1B was then re-purified by preparative SFC with the following conditions: Column: AD-H 2*25 cm; Mobile Phase A: CO$_2$: 80%, Mobile Phase B: IPA (HPLC grade): 20%; Flow rate: 60 ml/min; Detector 220 nm: $^1$NMR (600 MHz, CDCl$_3$) d 8.34 (s, 1H), 8.11 (s, 1H), 5.80 (s, 2H), 5.09-4.87 (m, 3H), 4.41 (dd, J=14.6 Hz, 3.0 Hz, 1H), 4.19 (dd, J=14.5 Hz, 6.9 Hz, 1H), 4.04-3.97 (m, 2H), 3.87 (dd, J=13.0 Hz, 6.9 Hz, 1H), 3.79 (dd, J=13.1 Hz, 11.6 Hz, 1H), 1.54 (bs, 6H) 1.44 (d, J=7.0 Hz, 3H), 1.28-1.19 (m, 15H); $^{31}$P NMR (243 MHz, CDCl$_3$) d 24.828 (s, 1P); LC/MS: [(M+1)]$^+$=529.3.

EXAMPLE 2

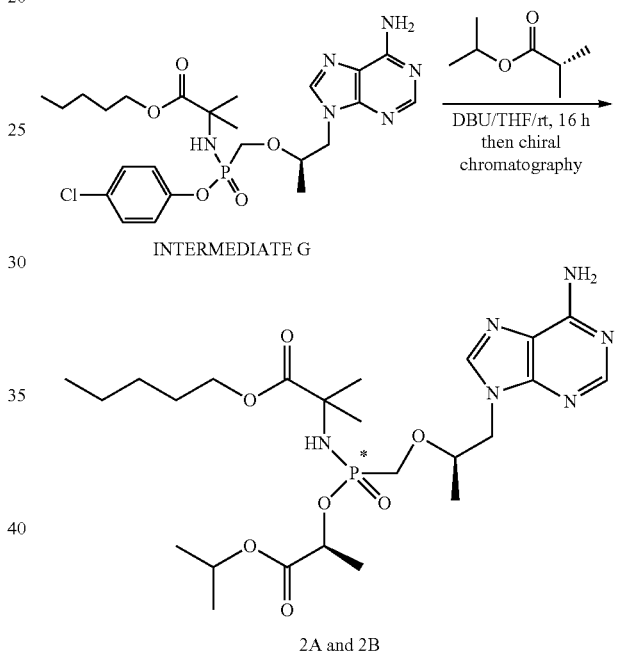

INTERMEDIATE G 2A and 2B

Step 1: Pentyl 2-((((((R)-1-(6-amino-9H-purin-9-yl)propan-2-yl)oxy)methyl)(((S)-1-isopropoxy-1-oxopropan-2-yl)oxy)(phosphoryl)amino)-2-methylpropanoate: To a solution of INTERMEDIATE G (7.0 g, 12.6 mmol) and INTERMEDIATE D (2.5 g, 18.9 mmol) in tetrahydrofuran (50 mL) was added DBU (1.9 g, 12.7 mmol). The reaction mixture was stirred at rt for 16 hours. Then the resulting mixture was concentrated under reduced pressure and the crude residue was purified by silica gel column chromatography (DCM/MeOH: 2% to 10%) to afford the title compound as a mixture of diastereoisomers.

Step 2: Pentyl 2-(((S)-((((R)-1-(6-amino-9H-purin-9-yl)propan-2-yl)oxy)methyl)(((S)-1-isopropoxy-1 -oxopropan-2-yl)oxy)phosphoryl)amino)-2-methylpropanoate and Pentyl 2-(((R)-((((R -1-(6-amino-9H-purin-9-yl)propan-2-yl)oxy)methyl)(((S)-1-isopropoxv-1-oxopropan-2-yl)oxy)phosphoryl)amino)-2-methylpropanoate (2A and 2B): The two isomers were separated by chiral preparative SFC with the following conditions: Column: Chiralpak IA 2*25 cm, 20 μm; Mobile Phase A: CO$_2$: 70%, Mobile Phase B: IPA (HPLC grade): 30%; Flow rate: 150 mL/min; Detector 254 nm; to afford Isomer 2A (faster eluting): $^1$H NMR (400 MHz; CD$_3$OD) δ 8.22 (s, 2H), 5.11-5.09 (m, 1H), 5.08-4.99 (m, 1H), 4.41 (dd, J=14.8, 2.8 Hz, 1H), 4.28-4.22 (m, 1H), 4.11 (t, J=6.8 Hz, 2H), 4.03-3.99 (m, 1H), 3.95-3.89 (m, 1H), 3.72-3.66 (m, 1H), 1.66-1.62 (m, 2H), 1.48-1.43 (m, 9H), 1.39-1.31 (m, 4H), 1.28 (d, J=7.6 Hz, 6H), 1.24 (d, J=6.4 Hz, 3H), 0.94 (t, J=6.8 Hz, 3H); $^{31}$P NMR (162 MHz; CD$_3$OD) δ 26.39; LC/MS: [(M+1)]$^+$=557.3; and Isomer 2B (slower eluting): $^1$H NMR (400 MHz; CD$_3$OD). δ 8.26 (s, 1H), 8.23 (s, 1H), 5.03-5.01 (m, 1H), 4.99-4.97 (m, 1H), 4.42 (dd, J=14.0, 2.8 Hz, 1H), 4.29-4.24 (m, 1H), 4.14 (t, J=6.8 Hz, 2H), 4.08-4.02 (m, 1H), 3.95-3.90 (m, 1H), 3.82-3.76 (m, 1H), 1.71-1.66 (m, 2H), 1.50 (s, 6H), 1.44 (d, J=6.8 Hz, 3H), 1.39-1.31 (m, 4H), 1.29-1.20 (m, 9H), 0.95 (t, J=6.8 Hz, 3H); $^{31}$P NMR (162 MHz; CD$_3$OD) δ 26.48; LC/MS: [(M+1)]$^+$=557.3.

EXAMPLE 3

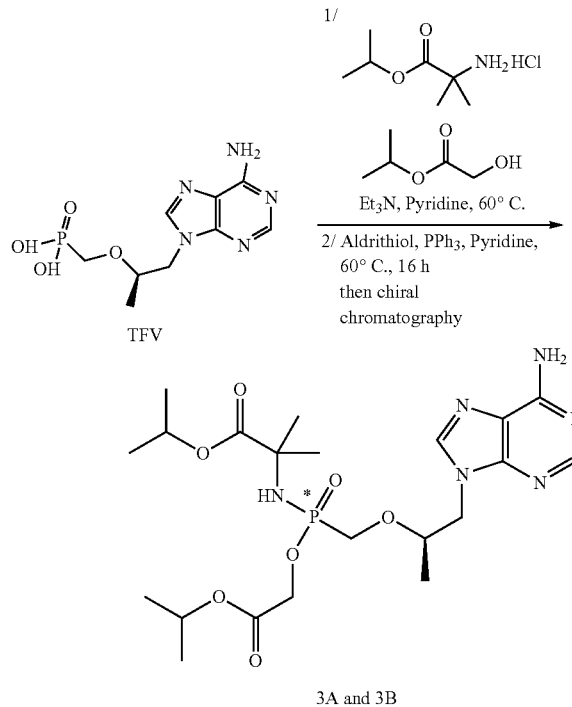

3A and 3B

Step 1: Isopropyl 2-((((((R)-1-(6-amino-9H-purin-9-yl)propan-2-yl oxy)methyl)(2-isopropoxy-2-oxoethoxy)phosphonyl)amino)-2-methylpropanoate: To a stirred mixture of TFV (3 g, 10.44 mmol), INTERMEDIATE A (4.22g, 20.89 mmol), isopropylglycolate (6.43g, 52.23 mmol) and triethylamine (12.68 g, 125.34 mmol) in pyridine (35 mL) heated at 60° C. for 5 min was added a freshly prepared solution of 1,2-di(pyridin-2-yl)disulfane (Aldrithiol, 16.67g, 74.16 mmol) and triphenylphosphine (19.65 g, 74.16 mmol) in pyridine (35 mL). The reaction mixture was stirred at 60° C. overnight, cooled to rt, and concentrated under reduced pressure. The crude residue was partitioned between EtOAc and an aqueous saturated NaHCO$_3$ solution. The organic layer was washed with brine, dried and concentrated under reduced pressure. The crude residue was purified by flash chromatography on silica gel (DCM/MeOH) to afford the title compound as a diastereomeric mixture.

Step 2: Isopropyl 2-(((S)-((((R)-1-(6-amino-9H-purin-9-yl)propan-2-yl)oxy)methyl)(2-isopropoxy-2-oxoethoxy) phosphoryl)amino)-2-methylpropanoate and Isopropyl 2-(((R)-((((R)-1-(6-amino-9H-purin-9-yl)propan-2-yl)oxy)methyl)(2-isopropoxy -2-oxoethoxy)phosphoryl)amino)-2-methylpropanoate (3A and 3B): The two isomers were separated by chiral Preparative HPLC with the following conditions: Column: Chiralpak IC 0.46*25 cm. 5 µm; Mobile Phase A: CO$_2$: 60%, Mobile Phase B: IPA: 40%; to afford Isomer 3A (faster eluting): $^1$H NMR (400 MHz; CDCl$_3$) δ 8.35 (s, 1H), 8.12 (s, 1H), 5.72 (s, 2H), 5.08 (heptuplet, J=6.21 Hz, 1H), 5.04 (hept, J=6.21 Hz, 1H), 4.56 (dd, J=16.32 Hz and 11.88 Hz, 1H), 4.46 (dd, J=16.32 Hz and 12.06 Hz, 1H), 4.40 (dd, J=14.37 Hz and 3.02 Hz, 1H), 4.19 (dd, J=14.37 Hz and 7.09 Hz, 1H); 4.03-3.96 (m, 2H), 3.88 (dd, J=13.30 Hz and 7.45 Hz, 1H), 3.72 (dd, J=13.30 Hz and 10.11 Hz, 1H), 1.52 (d, J=3.87 Hz, 6H), 1.27-1.25 (m, 12H), 1.22 (d, J=6.21 Hz, 3H); $^{31}$P NMR (198 MHz; CDCl$_3$) δ 26.06; LC/MS: [(M+1)]$^+$=515.4; and Isomer 3B (slower eluting): $^1$H NMR (400 MHz; CDCl$_3$). δ 8.35 (s, 1H), 8.11 (s, 1H), 5.71 (s, 2H), 5.12 (heptuplet, J=6.25 Hz, 1H), 4.99 (hept, J=6.25 Hz, 1H), 4.67 (dd, J=16.32 Hz and 11.83 Hz, 1H), 4.45 (dd, J=16.32 Hz and 12.43 Hz, 1H), 4.39 (dd, J=14.38 Hz and 2.38 Hz, 1H), 4.16 (dd, J=14.38 Hz and 7.49 Hz, 1H); 3.99-3.86 (m, 3H), 3.63 (dd, J=13.29 Hz and 9.44 Hz, 1H), 1.45 (d, J=4.56 Hz, 6H), 1.29-1.22 (m, 15H), $^{31}$P NMR (198 MHz; CDCl$_3$) δ 25.90; LC/MS: [(M+1)]$^+$= 515.7;

EXAMPLE 4

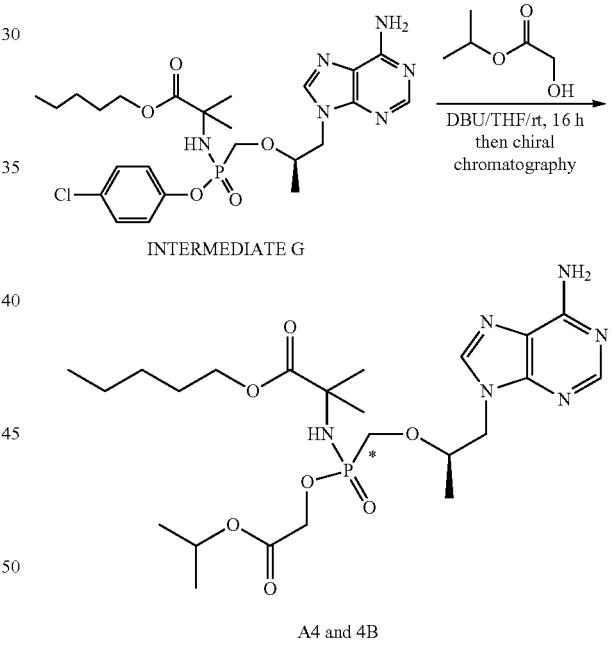

A4 and 4B

Step 1: Pentyl 2-((((((R)-1-(6-amino-9H-purin-9-yl)propan-2-yl)oxy)methyl)(2-isopropoxy-2-oxoethoxy)phosphoryl)amino)-2-methylpropanoate: Compounds 4A and 4B were prepared in a similar fashion to that described for the synthesis of Compounds 2A and 2B starting from INTERMEDIATE G with isopropylglycolate.

Step 2: Pentyl 2-(((S)-((((R)-1-(6-amino-9H-purin-9-yl)propan-2-yl)oxy)methyl)(2-isopropoxy-2-oxoethoxy)phosphoryl)amino)-2-methylpropanoate and Pentyl 2-(((R)-((((R) -1-(6-amino-9H-purin-9-yl)propan-2-yl)oxy)methyl) (2-isopropoxy-2-oxoethoxy)phosphoryl)amino)-2-methylpropanoate (4A and 4B): The two isomers were separated by chiral preparative SFC with the following condition: Column: Chiralpak IA 2*25 cm, 5 μm; Mobile Phase A: $CO_2$: 75%, Mobile Phase B: IPA: 25%; Flow rate: 40 mL/min; Detector: 254 nm; to afford Isomer 4A (faster eluting): $^1$H NMR (400 MHz; $CD_3OD$) δ 8.25 (s, 1H), 8.23 (s, 1H), 5.12-5.06 (m, 1H), 4.62 (dd, J=16.4, 10.4 Hz, 1H), 4.49 (dd, J=16.0, 10.4 Hz, 1H), 4.42 (dd, J=14.4, 2.8 Hz, 1H), 4.24 (dd, J=14.8, 7.6 Hz, 1H), 4.11 (t, J=6.8 Hz, 2H), 4.03-3.94 (m, 2H), 3.72 (dd, J=13.2, 9.6 Hz, 1H), 1.67-1.64 (m, 2H), 1.46 (s, 3H), 1.44 (s, 3H), 1.38-1.30 (m, 4H), 1.29-1.25 (m, 6H), 1.24 (d, J=6.0 Hz, 3H), 0.94 (t, J=6.8 Hz, 3H); $^{31}$P NMR (162 MHz; $CD_3OD$) δ 27.57; LC/MS: $[(M+1)]^+$=543.2; and Isomer 4B (slower eluting): $^1$H NMR (400 MHz; $CD_3OD$) δ 8.24 (s, 1H), 8.22 (s, 1H), 5.10-5.03 (m, 1H), 4.51 (d, J=10.8 Hz, 2H), 4.41 (dd, J=14.4, 2.8 Hz, 1H), 4.26 (dd, J=14.4, 7.2 Hz, 1H), 4.13 (t, J=6.8 Hz, 2H), 4.06-4.01 (m, 1H), 3.93 (dd, J=16.0, 8.0 Hz, 1H), 3.78 (dd, J=13.4, 9.6 Hz, 1H), 1.69-1.64 (m, 2H), 1.49 (s, 3H), 1.48 (s, 3H), 1.39-1.32 (m, 4H), 1.29-1.25 (m, 6H), 1.22 (d, J=6.0 Hz, 3H), 0.94 (t, J=6.8 Hz, 3H); $^{31}$P NMR (162 MHz; $CD_3OD$) δ 7.67; LC/MS: $[(M+1)]^+$=543.2.

The compounds in the following Examples were prepared in an analogous fashion to that described for Examples 1-4, wherein Step 1 describes preparation of the compound as a mixture of diastereoisomers. The diastereoisomer mixtures were separated in Examples 1-19 and were not separated for compounds in Examples 20-52. Conditions for the separations are provided in Examples 1-19. Isomers were separated by either preparative HPLC, preparative chiral HPLC or preparative chiral SFC. The noted "Intermediates" in the following Examples refer to the intermediate compound name or intermediate example letters (e.g., Intermediates C and E; or Intermediates: J and Isopropyl glycolate) that describe each of the intermediates that were used in Step 1 for each Example.

Example 5

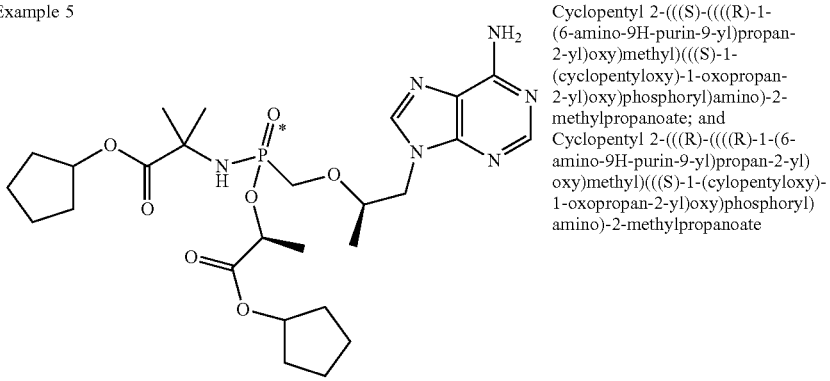

Cyclopentyl 2-(((S)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate; and
Cyclopentyl 2-(((R)-((((R)-1-(6-amino-9H-purin-9-yl)propan-2-yl)oxy)methyl)(((S)-1-(cylopentyloxy)-1-oxopropan-2-yl)oxy)phosphoryl)amino)-2-methylpropanoate Intermediates: C and E
Isomer separation/purification conditions: Preparative chiral SFC: CHIRALPAK-AD-H, 20
* 250 atm; Mobile Phase A: 25% EtOH.; Mobile Phase B: $CO_2$; Flow rate: 70 mL/min;
Gradient: isocratic; Detector: UV 220 nm

| Isomer | $^{31}$P NMR (ppm) | LC/MS (M + 1)$^+$ | Elution order |
|---|---|---|---|
| 5A | 24.67 ($CDCl_3$) | 581.7 | Faster eluting |
| 5B | 24.85 ($CDCl_3$) | 581.7 | Slower eluting |

EXAMPLE 6

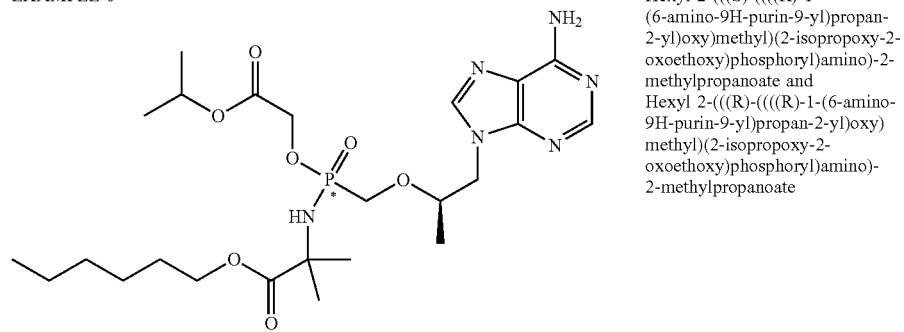

Hexyl 2-(((S)-((((R)-1-(6-amino-9H-purin-9-yl)propan-2-yl)oxy)methyl)(2-isopropoxy-2-oxoethoxy)phosphoryl)amino)-2-methylpropanoate and
Hexyl 2-(((R)-((((R)-1-(6-amino-9H-purin-9-yl)propan-2-yl)oxy)methyl)(2-isopropoxy-2-oxoethoxy)phosphoryl)amino)-2-methylpropanoate Intermediates: I and Isopropyl glycolate
Isomer separation/purification conditions: Preparative chiral HPLC: Chiralpak IA 20 × 250 mm, 5 μm; Mobile Phase A: Hexanes; Mobile Phase B: 30% EtOH; Flow rate: 20 mL/min; Gradient: isocratic; Detector: UV 254/220 nm

| Isomer | $^{31}$P NMR (ppm) | LC/MS (M + 1)$^+$ | Elution order |
|---|---|---|---|
| 6A | 27.57 (MeOD) | 557.5 | Faster eluting |
| 6B | 27.66 (MeOD) | 557.5 | Slower eluting |

| EXAMPLE 7 | 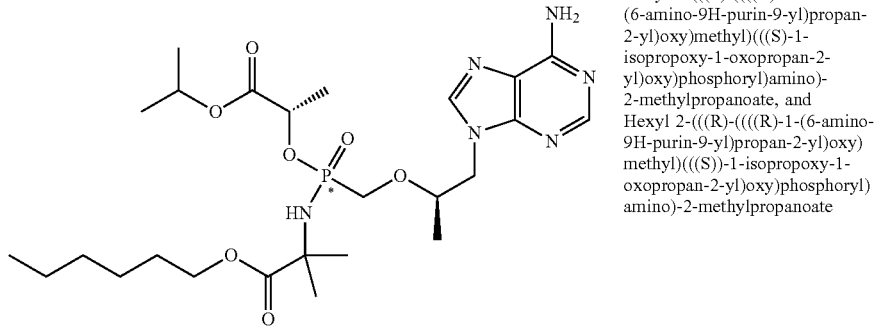 | Hexyl 2-(((S)-((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate, and Hexyl 2-(((R)-((((R)-1-(6-amino-9H-purin-9-yl)propan-2-yl)oxy)methyl)(((S))-1-isopropoxy-1-oxopropan-2-yl)oxy)phosphoryl)amino)-2-methylpropanoate |

Intermediates: I and D
Isomer separation/purification conditions: Preparative chiral HPLC: Chiralpak IA 20 × 250 mm, 5 μm; Mobile Phase A: Hexanes; Mobile Phase B: 30% EtOH; Flow rate: 20 mL/min; Gradient: isocratic; Detector: UV 254/220 nm

| Isomer | $^{31}$P NMR (ppm) | LC/MS (M + 1)$^+$ | Elution order |
| --- | --- | --- | --- |
| 7A | 26.40 (MeOD) | 571.4 | Faster eluting |
| 7B | 26.52 (MeOD) | 571.4 | Slower eluting |

| EXAMPLE 8 | 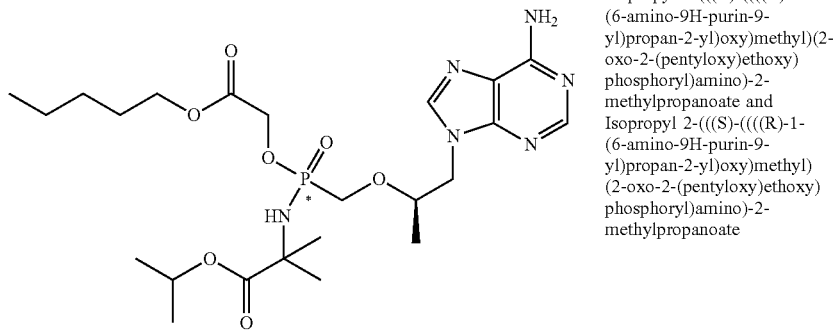 | Isopropyl 2-(((R)-((((R)-1-(6-amino-9H-purin-9-yl)propan-2-yl)oxy)methyl)(2-oxo-2-(pentyloxy)ethoxy)phosphoryl)amino)-2-methylpropanoate and Isopropyl 2-(((S)-((((R)-1-(6-amino-9H-purin-9-yl)propan-2-yl)oxy)methyl)(2-oxo-2-(pentyloxy)ethoxy)phosphoryl)amino)-2-methylpropanoate |

Intermediates: A and Pentyl glycolate
Isomer separation/purification conditions: Preparative chiral HPLC: Chiralpak IA 20 × 250 mm, 5 μm; Mobile Phase A: Hexanes; Mobile Phase B: 30% EtOH; Flow rate: 16 mL/min; Gradient: isocratic; Detector: UV 254/220 nm

| Isomer | $^{31}$P NMR (ppm) | LC/MS (M + 1)$^+$ | Elution order |
| --- | --- | --- | --- |
| 8A | 27.51 (MeOD) | 543.3 | Faster eluting |
| 8B | 27.60 (MeOD) | 543.3 | Slower eluting |

| EXAMPLE 9 | 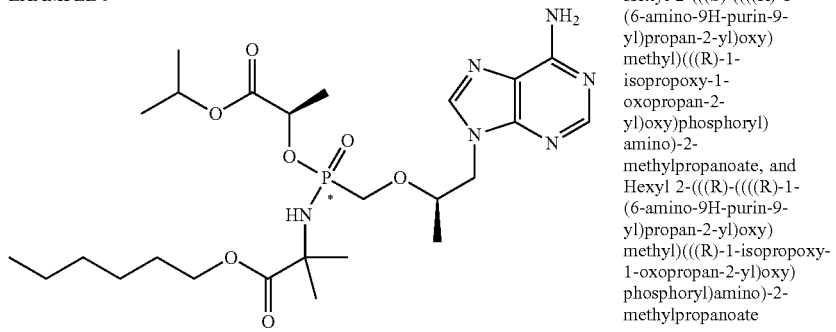 | Hexyl 2-(((S)-((((R)-1-(6-amino-9H-purin-9-yl)propan-2-yl)oxy)methyl)(((R)-1-isopropoxy-1-oxopropan-2-yl)oxy)phosphoryl)amino)-2-methylpropanoate, and Hexyl 2-(((R)-((((R)-1-(6-amino-9H-purin-9-yl)propan-2-yl)oxy)methyl)(((R)-1-isopropoxy-1-oxopropan-2-yl)oxy)phosphoryl)amino)-2-methylpropanoate |

-continued

| Intermediates: I and Q |
| --- |
| Isomer separation/purification conditions: Preparative HPLC - Waters XBridge Prep C18 5 μm OBD, 30 × 250 mm; Mobile phase A: 0.5N ammonium carbonate/acetonitrile; Mobile phase B: 0.5N ammonium carbonate/water; Gradient: 20-50% A over 59; Flow rate: 30 mL/min; Detector 260 nm |

| Isomer | $^{31}$P NMR (ppm) | LC/MS (M + 1)$^+$ | Retention time (min) |
| --- | --- | --- | --- |
| 9A | 24.60 (CDCl$_3$) | 571.4 | 52.30 |
| 9B | 24.72 (CDCl$_3$) | 571.4 | 55.05 |

EXAMPLE 10

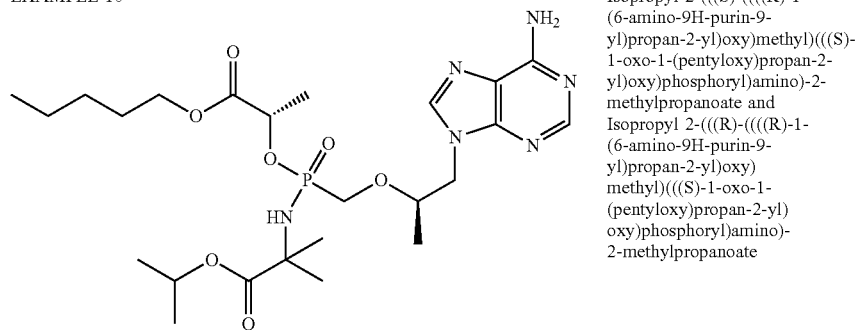

Isopropyl 2-(((S)-((((R)-1-(6-amino-9H-purin-9-yl)propan-2-yl)oxy)methyl)(((S)-1-oxo-1-(pentyloxy)propan-2-yl)oxy)phosphoryl)amino)-2-methylpropanoate and Isopropyl 2-(((R)-((((R)-1-(6-amino-9H-purin-9-yl)propan-2-yl)oxy)methyl)(((S)-1-oxo-1-(pentyloxy)propan-2-yl)oxy)phosphoryl)amino)-2-methylpropanoate

| Intermediates: A and U |
| --- |
| Isomer separation/purification conditions: Preparative chiral HPLC: CHIRALPAK-AD-H-SL001 20 × 250 mm; Mobile Phase A: Hexanes; Mobile Phase B: 30% EtOH; Flow rate: 19 mL/min; Gradient: isocratic; Detector: UV 254/220 nm |

| Isomer | $^{31}$P NMR (ppm) | LC/MS (M + 1)$^+$ | Elution order |
| --- | --- | --- | --- |
| 10A | 26.39 (MeOD) | 557.2 | Faster eluting |
| 10B | 26.50 (MeOD) | 557.2 | Slower eluting |

EXAMPLE 11

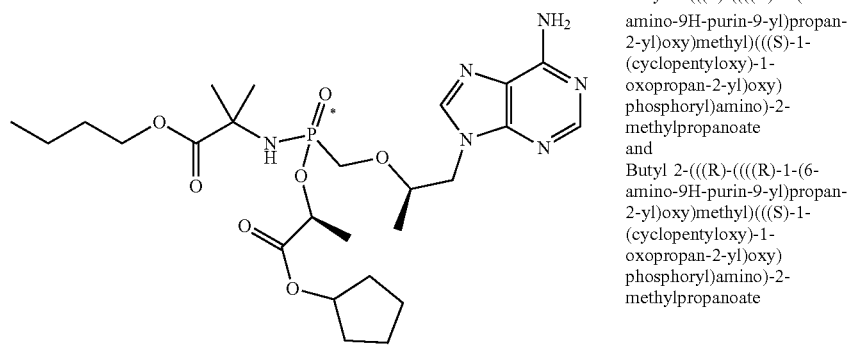

Butyl 2-(((S)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate and Butyl 2-(((R)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate

| Intermediates: J and E |
| --- |
| Isomer separation/purification conditions: Preparative chiral SFC: CHIRALPAK-AD-H, 20 * 250 mm; Mobile Phase A: 15% MeOH/0.1% NH$_4$OH.; Mobile Phase B CO$_2$; Flow rate: 80 mL/min; Gradient: isocratic; Detector: UV 220 nm |

| Isomer | $^{31}$P NMR (ppm) | LC/MS (M + 1)$^+$ | Elution order |
| --- | --- | --- | --- |
| 11A | 24.68 (d$_6$-DMSO) | 569.8 | Faster eluting |
| 11B | 24.82 (d$_6$-DMSO) | 569.8 | Slower eluting |

EXAMPLE 12

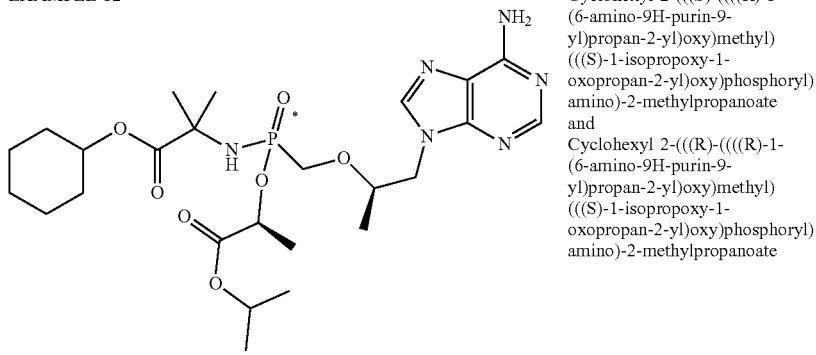

Cyclohexyl 2-(((S)-((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate
and
Cyclohexyl 2-(((R)-((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate Intermediates: N and D
Isomer separation/purification conditions: Preparative HPLC - Waters XBridge Prep C18 5 μm OBD, 30 × 250 mm; Mobile phase A: 0.5N ammonium carbonate/acetonitrile; Mobile phase B: 0.5N ammonium carbonate/water; Flow rate: 30 mL/min; Gradient 20-50% A over 59 min; Detector 260 nm

| Isomer | $^{31}$P NMR (ppm) | LC/MS (M + 1)$^+$ | Retention time (min) |
|---|---|---|---|
| 12A | 24.78 (CDCl$_3$) | 569.7 | 39.0 |
| 12B | 24.62 (CDCl$_3$) | 569.7 | 40.0 |

EXAMPLE 13

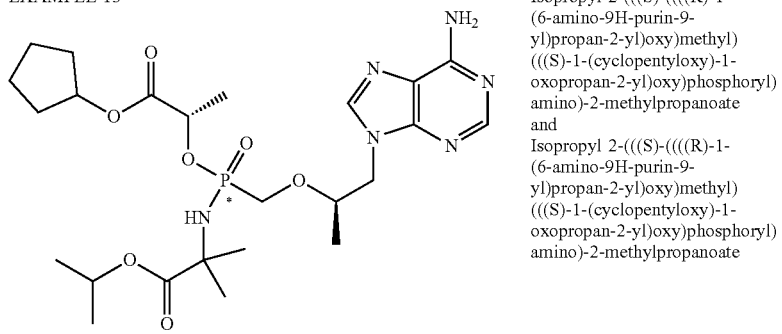

Isopropyl 2-(((S)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate
and
Isopropyl 2-(((S)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate Intermediates: A and E
Isomer separation/purification conditions: Preparative chiral SFC: CHIRALPAK IA-SFC-02 50 mm × 250 mm; Mobile Phase A: 40% MeOH (0.2% DEA); Mobile Phase B: CO$_2$; Flow rate: 160 mL/min; Gradient: isocratic; Detector: 254 nm

| Isomer | $^{31}$P NMR (ppm) | LC/MS (M + 1)$^+$ | Elution order |
|---|---|---|---|
| 13A | 26.35 (CDCl$_3$) | 555.4 | Faster eluting |
| 13B | 26.43 (CDCl$_3$) | 555.4 | Slower eluting |

EXAMPLE 14

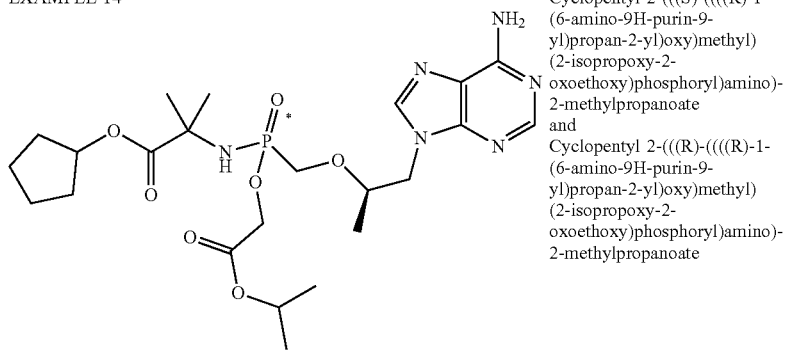

Cyclopentyl 2-(((S)-((((R)-1-(6-amino-9H-purin-9-yl)propan-2-yl)oxy)methyl)(2-isopropoxy-2-oxoethoxy)phosphoryl)amino)-2-methylpropanoate
and
Cyclopentyl 2-(((R)-((((R)-1-(6-amino-9H-purin-9-yl)propan-2-yl)oxy)methyl)(2-isopropoxy-2-oxoethoxy)phosphoryl)amino)-2-methylpropanoate Intermediates: C and Isopropyl glycolate
Isomer separation/purification conditions: Preparative HPLC - Water XBridge Prep C18 5 μm OBD, 30 × 250 mm; Mobile phase A: 0.5N ammonium carbonate/acetonitrile; Mobile phase B: 0.5N ammonium carbonate/water; Flow rate: 30 mL/min; Gradient: 20-50% A over 59 min; Detector 260 nm

| Isomer | $^{31}$P NMR (ppm) | LC/MS (M + 1)$^+$ | Retention time (min) |
|---|---|---|---|
| 14A | 25.95 (CDCl$_3$) | 541.7 | 28.8 |
| 14B | 26.08 (CDCl$_3$) | 541.7 | 29.9 |

EXAMPLE 15

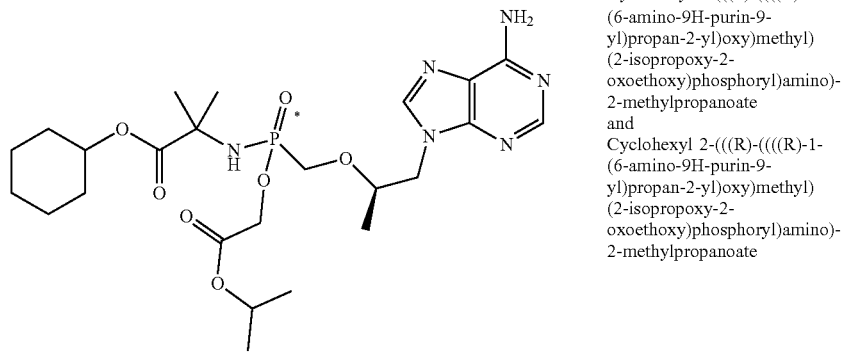

Cyclohexyl 2-(((S)-((((R)-1-(6-amino-9H-purin-9-yl)propan-2-yl)oxy)methyl)(2-isopropoxy-2-oxoethoxy)phosphoryl)amino)-2-methylpropanoate
and
Cyclohexyl 2-(((R)-((((R)-1-(6-amino-9H-purin-9-yl)propan-2-yl)oxy)methyl)(2-isopropoxy-2-oxoethoxy)phosphoryl)amino)-2-methylpropanoate Intermediates: N and Isopropyl glycolate
Isomer separation/purification conditions: Preparative HPLC - Waters XBridge Prep C18 5 μm OBD, 30 × 250 mm; Mobile phase A: 0.5N ammonium carbonate/acetonitrile; Mobile phase B: 0.5N ammonium carbonate/water; Flow rate: 30 mL/min; Gradient: 20-50% A over 59 min; Detector 260 nm

| Isomer | $^{31}$P NMR (ppm) | LC/MS (M + 1)$^+$ | Retention time (min) |
|---|---|---|---|
| 15A | 25.94 (CDCl$_3$) | 555.6 | 35.0 |
| 15B | 26.06 (CDCl$_3$) | 555.7 | 36.5 |

EXAMPLE 16

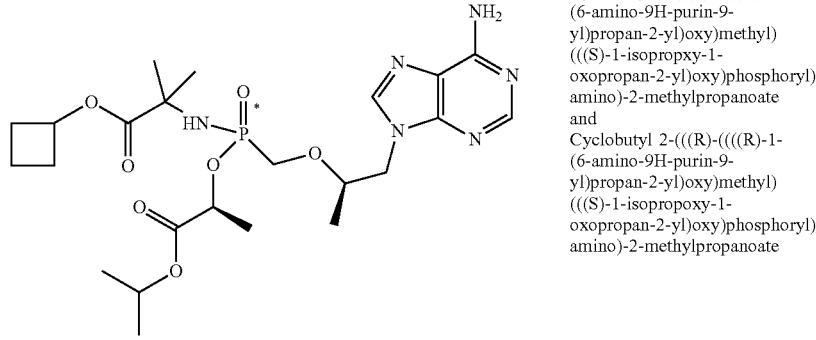

Cyclobutyl 2-(((S)-((((R)-1-(6-amino-9H-purin-9-yl)propan-2-yl)oxy)methyl)(((S)-1-isopropxy-1-oxopropan-2-yl)oxy)phosphoryl)amino)-2-methylpropanoate
and
Cyclobutyl 2-(((R)-((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate Intermediates: O and D
Isomer separation/purification conditions: Preparative HPLC - Waters XBridge Prep C18 5 μm OBD, 30 × 250 mm; Mobile phase A: 0.5N ammonium carbonate/acetonitrile; Mobile phase B: 0.5N ammonium carbonate/water; Flow rate: 30 mL/min; Gradient: 20-50% A over 59 min; Detector 260 nm

| Isomer | $^{31}$P NMR (ppm) | LC/MS (M + 1)$^+$ | Retention time (min) |
|---|---|---|---|
| 16A | 24.86 (CDCl$_3$) | 541.2 | 26.5 |
| 16B | 24.64 (CDCl$_3$) | 541.2 | 27.5 |

EXAMPLE 17

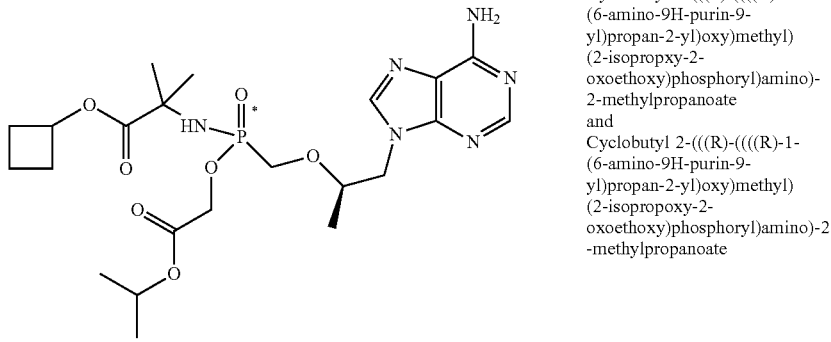

Cyclobutyl 2-(((S)-((((R)-1-(6-amino-9H-purin-9-yl)propan-2-yl)oxy)methyl)(2-isopropxy-2-oxoethoxy)phosphoryl)amino)-2-methylpropanoate
and
Cyclobutyl 2-(((R)-((((R)-1-(6-amino-9H-purin-9-yl)propan-2-yl)oxy)methyl)(2-isopropoxy-2-oxoethoxy)phosphoryl)amino)-2-methylpropanoate Intermediates: O and Isopropyl glycolate
Isomer separation/purification conditions: Preparative HPLC - Waters XBridge Prep C18 5 μm OBD, 30 × 250 mm; Mobile phase A: 0.5N ammonium carbonate/Acetonitrile; Mobile phase B: 0.5N ammonium carbonate/water; Flow rate: 30 mL/min; Gradient: 20-50% A over 59 min; Detector 260 nm

| Isomer | $^{31}P$ NMR (ppm) | LC/MS $(M + 1)^+$ | Retention time (min) |
|---|---|---|---|
| 17A | 25.96 (CDCl$_3$) | 527.2 | 22.5 |
| 17B | 26.09 (CDCl$_3$) | 527.2 | 23.5 |

EXAMPLE 18

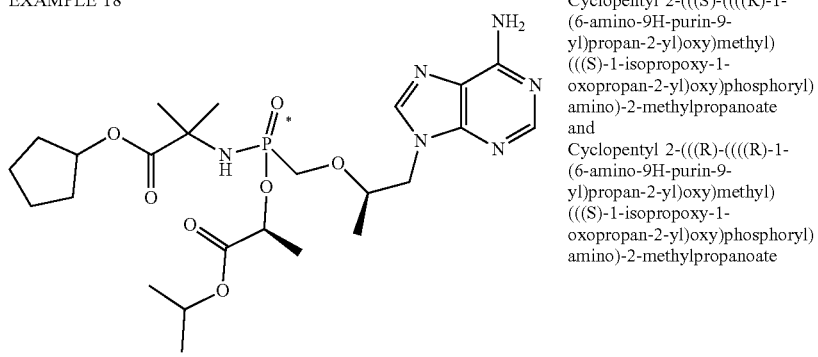

Cyclopentyl 2-(((S)-((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate
and
Cyclopentyl 2-(((R)-((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate Intermediates: C and D
Isomer separation/purification conditions: Preparative chiral SFC: CHIRALPAK-AD-H, 30 * 250 mm; Mobile Phase A: 15% MeOH.; Mobile Phase B: CO$_2$; Flow rate: 70 mL/min; Gradient: isocratic; Detector: UV 220 nm

| Isomer | $^{31}P$ NMR (ppm) | LC/MS $(M + 1)^+$ | Elution order |
|---|---|---|---|
| 18A | 24.72 (d$_6$-DMSO) | 555.6 | Faster eluting |
| 18B | 24.83 (d$_6$-DMSO) | 555.6 | Slower eluting |

EXAMPLE 19

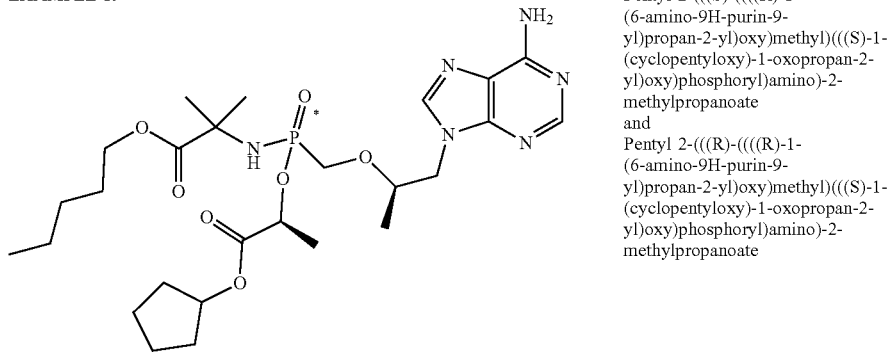

Pentyl 2-(((S)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate
and
Pentyl 2-(((R)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate -continued Intermediates: B and E
Isomer separation/purification conditions: Preparative chiral SFC: CHIRALPAK AD-H
SFC 50 * 250 mm, 5 μm; Mobile Phase A: 40% EtOH; Mobile Phase B: $CO_2$; Flow rate: 160
mL/min; Gradient: isocratic; Detector: 254 nm

| Isomer | $^{31}$P NMR (ppm) | LC/MS (M + 1)$^+$ | Elution order |
|---|---|---|---|
| 19A | 26.36 (meOD) | 583.3 | Faster eluting |
| 19B | 26.47 (MeOD) | 583.3 | Slower eluting |

| Ex. | Structure | Name | LC/MS (M + 1)$^+$ |
|---|---|---|---|
| 20 | Intermediates: A and Q | Isopropyl 2-((((((R)-1-(6-amino-9H-purin-9-yl)propan-2-yl)oxy)methyl)(((R)-1-isopropoxy-1-oxopropan-2-yl)oxy)phosphoryl)amino)-2-methylpropanoate | 529.5 |
| 21 | Intermediates: K and Isopropyl glycolate | Propyl 2-((((((R)-1-(6-amino-9H-purin-9-yl)propan-2-yl)oxy)methyl)(2-isopropoxy-2-oxoethoxy)phosphoryl)amino)-2-methylpropanoate | 515.5 |
| 22 | Intermediates: K and D | Propyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate | 529.4 |

| Ex. | Structure | Name | LC/MS (M + 1)+ |
|---|---|---|---|
| 23 | Intermediates: K and Q | Propyl 2-((((((R)-1-(6-amino-9H-purin-9-yl)propan-2-yl)oxy)methyl)(((R)-1-isopropoxy-1-oxopropan-2-yl)oxy)phosphoryl)amino)-2-methylpropanoate | 529.2 |
| 24 | Intermediates: J and Isopropyl glycolate | Butyl 2-((((((R)-1-(6-amino-9H-purin-9-yl)propan-2-yl)oxy)methyl)(2-isopropoxy-2-oxoethoxy)phosphoryl)amino)-2-methylpropanoate | 529.2 |
| 25 | Intermediates: J and D | Butyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate | 543.2 |
| 26 | Intermediates: J and Q | Butyl 2-((((((R)-1-(6-amino-9H-purin-9-yl)propan-2-yl)oxy)methyl)(((R)-1-isopropoxy-1-oxopropan-2-yl)oxy)phosphoryl)amino)-2-methylpropanoate | 543.2 |

| Ex. | Structure | Name | LC/MS (M + 1)+ |
|---|---|---|---|
| 27 | Intermediates: L and Isopropyl glycolate | Ethyl 2-(((((R)-1-(6-amino-9H-purin-9-yl)propan-2-yl)oxy)methyl)(2-isopropoxy-2-oxoethoxy)phosphoryl)amino)-2-methylpropanoate | 501.2 |
| 28 | Intermediates: L and D | Ethyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate | 515.2 |
| 20 | Intermediates: L and Q | Ethyl 2-((((((R)-1-(6-amino-9H-purin-9-yl)propan-2-yl)oxy)methyl)(((R)-1-isopropoxy-1-oxopropan-2-yl)oxy)phosphoryl)amino)-2-methylpropanoate | 515.2 |
| 30 | Intermediates: M and Isopropyl glycolate | Isobutyl 2-((((((R)-1-(6-amino-9H-purin-9-yl)propan-2-yl)oxy)methyl)(2-isopropoxy-2-oxoethoxy)phosphoryl)amino)-2-methylpropanoate | 529.6 |

-continued

| Ex. | Structure | Name | LC/MS (M + 1)+ |
|---|---|---|---|
| 31 | 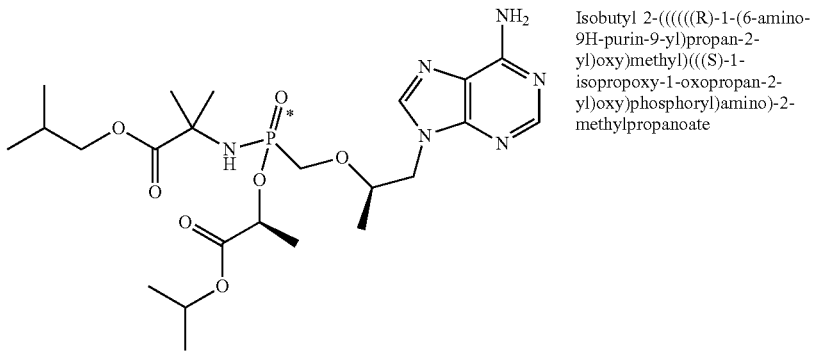Intermediates: M and D | Isobutyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate | 543.7 |
| 32 | 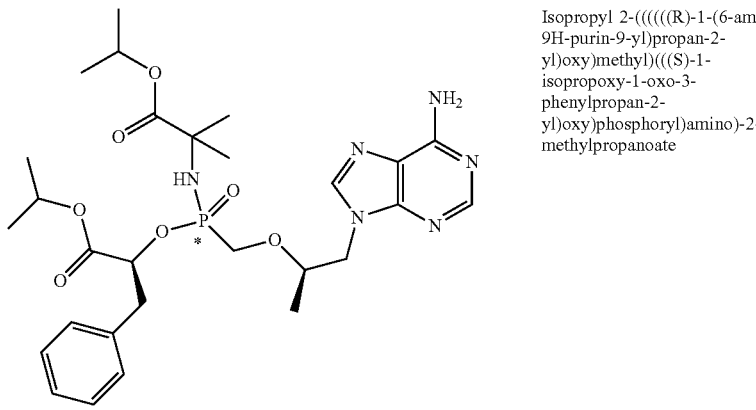Intermediates: A and R | Isopropyl 2-((((((R)-1-(6-amino-9H-purin-9-yl)propan-2-yl)oxy)methyl)(((S)-1-isopropoxy-1-oxo-3-phenylpropan-2-yl)oxy)phosphoryl)amino)-2-methylpropanoate | 605.4 |
| 33 | 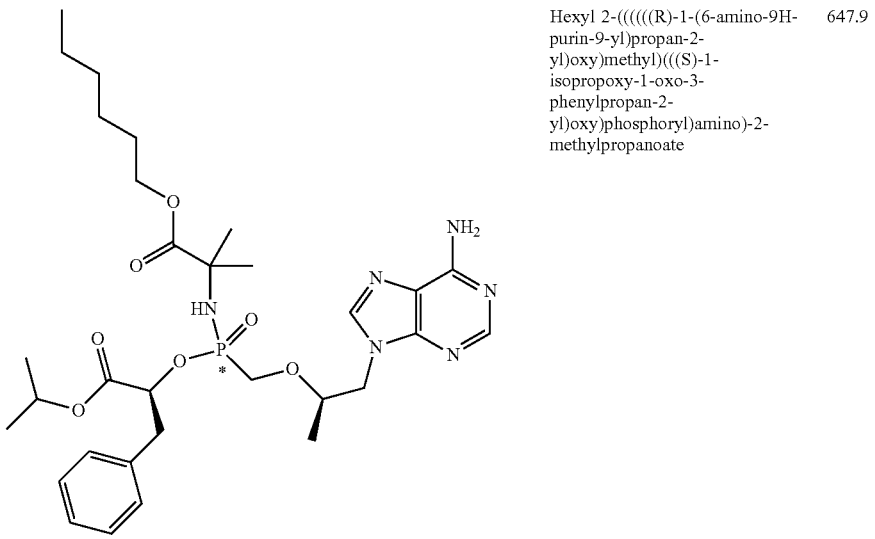Intermediates: I and R | Hexyl 2-((((((R)-1-(6-amino-9H-purin-9-yl)propan-2-yl)oxy)methyl)(((S)-1-isopropoxy-1-oxo-3-phenylpropan-2-yl)oxy)phosphoryl)amino)-2-methylpropanoate | 647.9 |

| Ex. | Structure | Name | LC/MS (M + 1)+ |
|---|---|---|---|
| 34 | 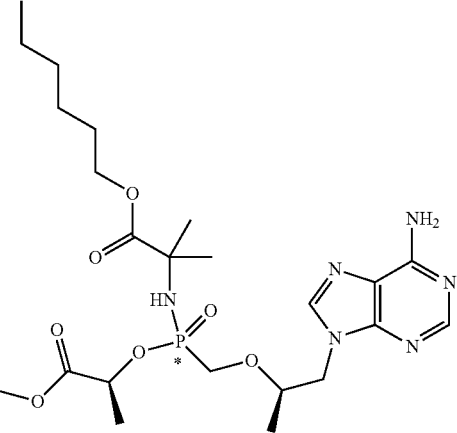<br>Intermediates: I and E | Hexyl 2-((((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate | 597.9 |
| 35 | 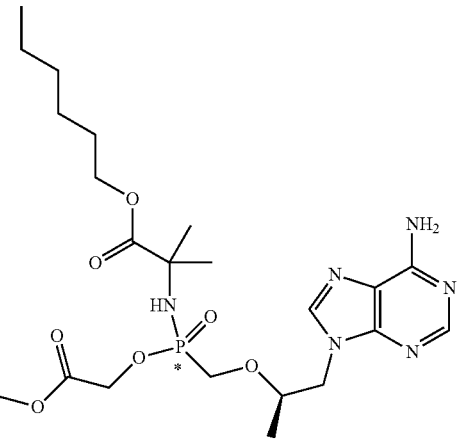<br>Intermediates: I and S | Hexyl 2-((((((R)-1-(6-amino-9H-purin-9-yl)propan-2-yl)oxy)methyl)(2-(cyclohexyloxy)-2-oxoethoxy)phosphoryl)amino)-2-methylpropanoate | 583.8 |
| 36 | 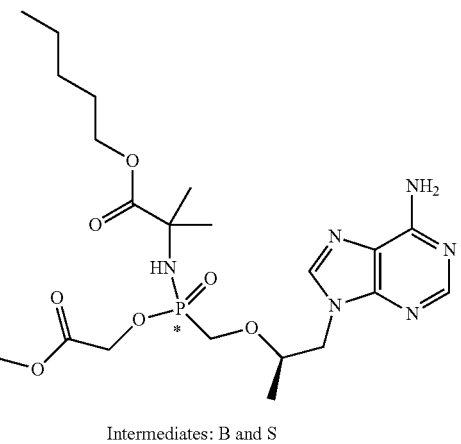<br>Intermediates: B and S | Pentyl 2-((((((R)-1-(6-amino-9H-purin-9-yl)propan-2-yl)oxy)methyl)(2-(cyclopentyloxy)-2-oxoethoxy)phosphoryl)amino)-2-methylpropanoate | 569.7 |

| Ex. | Structure | Name | LC/MS (M + 1)+ |
|---|---|---|---|
| 37 | Intermediates: M and E | Isobutyl 2-((((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate | 569.8 |
| 38 | Intermediates: K and S | Propyl 2-((((((R)-1-(6-amino-9H-purin-9-yl)propan-2-yl)oxy)methyl)(2-(cyclopentyloxy)-2-oxoethoxy)phosphoryl)amino)-2-methylpropanoate | 541.2 |
| 39 | Intermediates: C and D | Cyclopentyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate | 555.5 |
| 40 | Intermediates: A and Ethyl-(S)-lactate | Isopropyl 2-((((((R)-1-(6-amino-9H-purin-9-yl)propan-2-yl)oxy)methyl)(((S)-1-ethoxy-1-oxopropan-2-yl)oxy)phosphoryl)amino)-2-methylpropanoate | 515.5 |

| Ex. | Structure | Name | LC/MS (M + 1)+ |
|---|---|---|---|
| 41 | Intermediates: P and D | Benzyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate | 577.7 |
| 42 | Intermediates: P and Isopropyl glycolate | Benzyl 2-((((((R)-1-(6-amino-9H-purin-9-yl)propan-2-yl)oxy)methyl)(2-isopropoxy-2-oxoethoxy)phosphoryl)amino)-2-methylpropanoate | 563.6 |
| 43 | Intermediates: I and Ethyl-(S)-lactate | Hexyl 2-((((((R)-1-(6-amino-9H-purin-9-yl)propan-2-yl)oxy)methyl)(((S)-1-ethoxy-1-oxopropan-2-yl)oxy)phosphoryl)amino)-2-methylpropanoate | 557.5 |

| Ex. | Structure | Name | LC/MS (M + 1)+ |
|---|---|---|---|
| 44 | 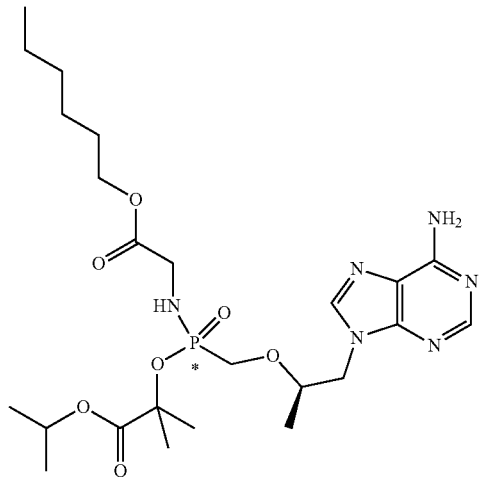<br>Intermediates: I and T | Hexyl 2-((((((R)-1-(6-amino-9H-purin-9-yl)propan-2-yl)oxy)methyl)((1-isopropoxy-2-methyl-1-oxopropan-2-yl)oxy)phosphoryl)amino)-2-methylpropanoate | 585.4 |
| 45 | 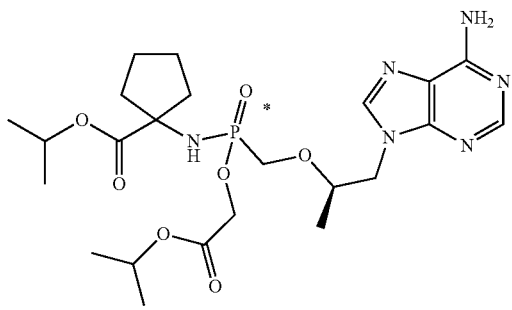<br>Intermediates: V and Isopropyl glycolate | Isopropyl 1-((((((R)-1-(6-amino-9H-purin-9-yl)propan-2-yl)oxy)methyl)(2-isopropoxy-2-oxoethoxy)phosphoryl)amino)cyclopentane-1-carboxylate | 541.7 |
| 46 | 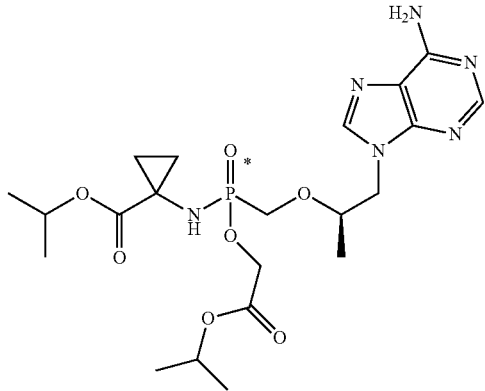<br>Intermediates: W and Isopropyl glycolate | Isopropyl 1-((((((R)-1-(6-amino-9H-purin-9-yl)propan-2-yl)oxy)methyl)(2-isopropoxy-2-oxoethoxy)phosphoryl)amino)cyclopropane-1-carboxylate | 513.4 |

| Ex. | Structure | Name | LC/MS (M + 1)+ |
|---|---|---|---|
| 47 | Intermediates: W and D | Isopropyl 1-((((((R)-1-(6-amino-9H-purin-9-yl)propan-2-yl)oxy)methyl)(((S)-1-isopropoxy-1-oxopropan-2-yl)oxy)phosphoryl)amino) cyclopropane-1-carboxylate | 527.5 |
| 48 | Intermediates: V and D | Isopropyl 1-((((((R)-1-(6-amino-9H-purin-9-yl)propan-2-yl)oxy)methyl)(((S)-1-isopropoxy-1-oxopropan-2-yl)oxy)phosphoryl)amino)cyclo-pentane-1-carboxylate | 555.4 |
| 49 | Intermediates: X and Isopropyl glycolate | Isopropyl 1-((((((R)-1-(6-amino-9H-purin-9-yl)propan-2-yl)oxy)methyl)(2-isopropoxy-2-oxoethoxy)phosphoryl)amino) cyclobutane-1-carboxylate | 527.2 |
| 50 | Intermediates: X and D | Isopropyl 1-((((((R)-1-(6-amino-9H-purin-9-yl)propan-2-yl)oxy)methyl)(((S)-1-isopropoxy-1-oxopropan-2-yl)oxy)phosphoryl)amino)cyclo-butane-1-carboxylate | 541.2 |

-continued

| Ex. | Structure | Name | LC/MS (M + 1)+ |
|---|---|---|---|
| 51 | Intermediates: Y and Isopropyl glycolate | Isopropyl 1-((((((R)-1-(6-amino-9H-purin-9-yl)propan-2-yl)oxy)methyl)(2-isopropoxy-2-oxoethoxy)phosphoryl)amino)cyclohexane-1-carboxylate | 555.4 |
| 52 | Intermediates: Y and D | Isopropyl 1-((((((R)-1-(6-amino-9H-purin-9-yl)propan-2-yl)oxy)methyl)(((S)-1-isopropoxy-1-oxopropan-2-yl)oxy)phosphoryl)amino)cyclohexane-1-carboxylate | 569.4 |

EXAMPLE 53

Assessing Antiviral Potency in a Multiple Round HIV-1 Infection Assay (Viking Assay)

The antiviral activity of the tenofovir prodrugs of the Examples herein was assessed in an assay that measures the rate of replication of HIV in cell culture, termed the Viking assay (Viral KINetics in Green cells) and performed as follows. HIV-1 replication was monitored using MT4-gag-GFP clone D3 (hereafter designated MT4-GFP), which are MT-4 cells modified to harbor a GFP reporter gene, the expression of which is dependent on the HIV-1 expressed proteins tat and rev. Productive infection of an MT4-GFP cell with HIV-1 results in GFP expression approximately 24 h post-infection. MT4-GFP cells were maintained at 37° C./5% CO2/90% relative humidity in RPMI 1640 supplemented with 10% fetal bovine serum, 100 µ/ml penicillin/streptomycin, and 400 µg/ml G418 to maintain the reporter gene. For infections, MT4-GFP cells were placed in the same medium lacking G418 and infected overnight with HIV-1 (H9/IIIB strain) virus at an approximate multiplicity of infection of 0.01 in the same incubation conditions. Cells were then washed and re-suspended in either RPMI 1640 supplemented with 10% or 50% normal human serum (NFIS) at $1.6 \times 10^5$ cells/mL (10% NHS or 50% NHS, respectively). Compound plates were prepared by dispensing compounds dissolved in DMSO into wells of 384 well poly-D-lysine-coated plates (0.2 µl/well) using an ECHO acoustic dispenser. Each compound was tested in a 10-point serial 3-fold dilution (typical final concentrations: 8.4 µM-0.42 nM). Controls included no inhibitor (DMSO only) and a combination of three antiviral agents (efavirenz, indinavir, an in-house integrase strand transfer inhibitor at final concentrations of 4 µM each). Cells were added (50 µL/well) to compound plates and the infected cells were maintained at 37° C./5% CO2/90% relative humidity.

infected cells were quantified at two time points, ~48 h and ~72 h post-infection, by counting the number of green cells in each well using an Acumen eX3 scanner. The increase in the number of green cells over ~24 h period gives the reproductive ratio, $R_0$, which is typically 5-15 and has been shown experimentally to be in logarithmic phase (data not shown). Inhibition of $R_0$ is calculated for each well, and $IC_{50}$s determined by non-linear 4-parameter curve fitting. Assay $IC_{50}$ results are shown in Table 2.

EXAMPLE 54

Prodrug Stability Assay in Bio-Relevant Media

The following assay was employed to evaluate the stability of the prodrugs in simulated gastrointestinal tract conditions. Preparation of fasted state simulated intestinal fluid (FaSSIF) using Phares SIF Powder was carried out according to protocols from Phare Drug Delivery AG (Baselland, Switzerland). For sample preparation, 10 µL stock solutions (10 mM) of prodrug substance in DMSO was added to 990 µL of 0.5 mg/mL Pancreatin solution (Fisher CAS#8049-47-6) in FaSSIF. Two samples were prepared for each compound at initial. If the sample was clear solution at the beginning, ran one sample directly as initial by HPLC; if the sample was not clear at starting, diluted the sample by 100% ACN. Put the other sample under 37° C. and observed the sample at 5 h time-point. At 5 h time point, if the sample was clear solution then performed HPLC analysis directly; if it was not clear solution, diluted the sample by 100% ACN and assayed by HPLC. All the samples were vortexed for 3 min and observed before injection. For the diluted samples, the area will be multiplied by a factor when data analysis. The analysis was carried out with an Agilent 1100 series HPLC with autosampler. The column was usually a Poroshell 120 EC -C18, 4.6×50 mm, 2.7 μm. The flow rate was 1.8 mL/min, and the injection volume was 5 or 10 μL. UV detection was in the range 210-400 nm. The mobile phase consisted of solvent A (water plus 10 mM tetrabutylammonium bromide) and solvent B (acetonitrile) with a gradient of 90% solvent A at 0 min changing to 95% solvent B over 6 min, maintained for 1.5 min, then reverting to 90% solvent A over 1.6 min. The area of the parent in prodrug at 5h time point was divided by the area of the parent in prodrug at 0 h time point, to generate the % claimed parent ratio, which are summarized in Table 2 for GI Tract stability.

EXAMPLE 55

Pharmacokinetic Studies in Dogs—In Vivo Dog PK

Prodrugs were administered to beagle dogs through intravenous (IV) and oral (P.O.) administrations in a non-crossover manner. The IV dose was prepared in 20% hydroxypropyl β-cyclodextrin (HPBCD) and was administered via cephalic or saphenous vein, The P.O. dose was prepared in 10% polysorbate 80 (Tween 80) and was administered via gavage.

Blood samples were serially collected following dose administration for up to 48 hr and plasma was separated by centrifugation. The concentrations of prodrugs in dog plasma were determined by LC-MS/MS assay following a protein precipitation step and addition of an appropriate internal standard (labetalol, imipramine or diclofenac). Quantification was done by determining peak area-ratios of the prodrugs and tenofovir to the internal standard. Additional blood sample(s) was collected following dose administration for up to 24 hr. Peripheral blood mononuclear cells (PBMCs) were isolated by centrifugation, using tubes and reagents specified for such application. The concentrations of tenofovir and/or its phosphate conjugate(s) in PBMCs were determined by an LC-VIS/MS assay following a protein precipitation step and addition of an appropriate internal standard (labetalol, imipramine or diclofenac), Quantification was done by determining peak area-ratios of tenofovir and/or its phosphate conjugate(s) to the internal standard.

Pharmacokinetic parameters were obtained using non-compartmental methods (Watson®). The area under the plasma concentration-time curve ($AUC_{0-t}$) was calculated from the first time point (0 min) up to the last time point with measurable drug concentration using the linear trapezoidal or linear/log-linear trapezoidal rule. The IV plasma clearance was calculated by dividing the dose by $AUC_{0-inf}$. The terminal half-life of elimination was determined by unweighted linear regression analysis of the log-transformed data. The time points for determination of half-life were selected by visual inspection of the data. The volume of distribution at steady state ($Vd_{ss}$) was obtained from the product of plasma clearance and mean residence time (determined by dividing the area under the first moment curve by the area under the curve). The maximum plasma concentration ($C_{max}$) and the time at which maximum concentration occurred ($T_{max}$) were obtained by inspection of the plasma concentration-time data. Absolute oral bioavailability (%F) was determined from dose -adjusted IV and P.O. AUC ratios of the prodrug. Table 2 shows in vivo dog PK data in the form of TFV-DP concentrations (μM) in dog PBMCs at 24 h following a 10 mg/kg P.O. dose of the indicated prodrug

TABLE 2

| Example | Viking, $IC_{50}$ (10% NHS) (nM) | Viking, $IC_{50}$ (50% NHS) (nM) | GI Tract stability (%) | In Vivo Dog PK (μM) |
|---|---|---|---|---|
| 1A | 14.69 | 61.08 | 85.74 | |
| 1B | 7.43 | 12.08 | 99.82 | |
| 2A | 4.05 | 22.15 | 61.61 | |
| 2B | 18.22 | 70.86 | 91.95 | 22.11 |
| 3A | 36.62 | 121.1 | 96.63 | |
| 3B | 29.10 | 47.88 | 95.71 | |
| 4A | 13.88 | 86.55 | 99.07 | 21.59 |
| 4B | 19.42 | 157.50 | 98.87 | |
| 5A | 5.71 | 45.00 | | |
| 5B | 5.73 | 23.42 | | |
| 6A | 3.14 | 15.20 | 95.97 | |
| 6B | 2.14 | 7.99 | 73.16 | |
| 7A | 5.03 | 21.02 | 15.36 | |
| 7B | 0.37 | 1.01 | 76.64 | 11.75 |
| 8A | 6.76 | 27.02 | 94.11 | |
| 8B | 22.68 | 161.2 | 71.6 | |
| 9A | 4.20 | 26.06 | | |
| 9B | 1.00 | 2.78 | 6.16 | |
| 10A | 26.29 | 142.00 | | |
| 10B | 85.63 | 356.90 | | |
| 11A | 24.84 | 66.17 | | |
| 11B | 3.98 | 22.80 | | |
| 12A | 5.71 | 25.18 | 98.95 | |
| 12B | 6.07 | 13.49 | | |
| 13A | 6.17 | 51.07 | 70.30 | |
| 13B | 9.44 | 60.20 | 99.72 | |
| 14A | 10.01 | 23.53 | | |
| 14B | 5.40 | 36.19 | | |
| 15A | 9.98 | 28.51 | | |
| 15B | 10.31 | 44.17 | | |
| 16A | 2.61 | 7.50 | | |
| 16B | 4.75 | 17.05 | | |
| 17A | 6.39 | 12.72 | | |
| 17B | 6.70 | 18.35 | 99.32 | |
| 18A | 6.59 | 16.46 | 76.31 | |
| 18B | 2.69 | 8.77 | 91.31 | 23.23 |
| 19A | 14.01 | 49.69 | | |
| 19B | 3.01 | 9.93 | 100.00 | |
| 20 | 20.97 | 96.96 | 7.19 | |
| 21 | 6.15 | 11.99 | 99.36 | |
| 22 | 4.65 | 17.67 | 79.24 | |
| 23 | 2.67 | 8.19 | 4.28 | |
| 24 | 4.78 | 27.80 | 98.30 | |
| 25 | 2.44 | 10.5 | 79.61 | |
| 26 | 3.10 | 8.74 | 9.01 | |
| 27 | 10.08 | 13.31 | | |
| 28 | 6.38 | 19.71 | | |
| 29 | 9.22 | 17.21 | | |
| 30 | 4.38 | 11.98 | | |
| 31 | 2.39 | 7.57 | 85.48 | |
| 32 | 3.34 | 23.18 | | |
| 33 | 1.69 | 5.06 | 26.96 | |
| 34 | 3.57 | 12.92 | | |
| 35 | 3.83 | 14.00 | | |
| 36 | 2.39 | 6.04 | 88.87 | |
| 37 | 10.28 | 63.08 | | |
| 38 | 2.68 | 6.26 | 96.64 | |
| 39 | 3.43 | 12.63 | | |
| 40 | 19.17 | 58.71 | | |
| 41 | 2.87 | 12.49 | 58.50 | |
| 42 | 5.00 | 21.77 | 73.54 | |
| 43 | 6.15 | 20.37 | | |
| 44 | 1.42 | 1.81 | | |
| 45 | 15.61 | 62.58 | 99.44 | |
| 46 | 385.80 | 702.80 | 98.18 | |
| 47 | 91.61 | 209.20 | 93.55 | |
| 48 | 13.29 | 37.31 | | |

TABLE 2-continued

| Example | Viking, IC$_{50}$ (10% NHS) (nM) | Viking, IC$_{50}$ (50% NHS) (nM) | GI Tract stability (%) | In Vivo Dog PK (µM) |
|---|---|---|---|---|
| 49 | 19.55 | 36.99 | 100.50 | |
| 50 | 8.66 | 34.30 | | |
| 51 | 9.80 | 24.86 | 99.70 | |
| 52 | 10.83 | 45.60 | | |

What is claimed is:

1. A compound of structural Formula I:

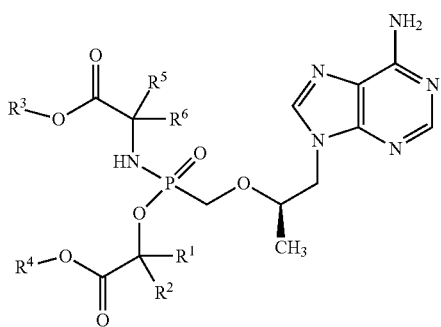

or a pharmaceutically acceptable salt thereof, wherein:
$R^1$ and $R^2$ are each independently selected from (a) H, (b) —$C_{1-4}$alkyl, (c) —$C_{1-4}$alkyl substituted with —OH, —SH, —SCH$_3$, —NH$_2$ or —NH—C(=NH)—NH$_2$, (d) —CH$_2$-phenyl, (e) —CH$_2$-phenol, (f) —(CH$_2$)$_{1-2}$—COOH, (g) —(CH$_2$)$_{1-2}$—CONH$_2$, (h) —CH$_2$-1H-indole, (i) —CH$_2$-imidazole, (j) aryl or (k) heteroaryl;
$R^3$ is selected from:
(a) —$C_{1-10}$alkyl unsubstituted or substituted with one to three substituents independently selected from fluoro, chloro, bromo, —OR$^{7a}$, —SH, —NR$^{9a}$R$^{10a}$, —$C_{3-6}$cycloalkyl or spiro—$C_{3-6}$cycloalkyl,
(b) —CH$_2$-phenyl unsubstituted or substituted with one to three substituents independently selected from fluoro, chloro, bromo, —OR$^{8a}$, —SH, —NR$^{9a}$R$^{10a}$ or —$C_{1-3}$alkyl,
(c) —$C_{3-8}$cycloalkyl unsubstituted or substituted with one to three substituents independently selected from fluoro, chloro, bromo, —OR$^{8a}$, —SH, —NR$^{9a}$R$^{10a}$ or —$C_{1-3}$alkyl,
(d) aryl unsubstituted or substituted with one to three substituents independently selected from fluoro, chloro, bromo, —OR$^{8a}$, —SH, —NR$^{9a}$R$^{10a}$ or —$C_{1-3}$alkyl,
(e) —$C_{1-5}$alkyl—X—$C_{1-5}$alkyl wherein X is O, S or NH,
(f) heteroaryl unsubstituted or substituted with one to three substituents independently selected from fluoro chloro, bromo, —OR$^{8a}$, —SH, —NR$^{9a}$R$^{10a}$ or —$C_{1-3}$alkyl, or
(g) a heterocyclic ring unsubstituted or substituted with one to three substituents independently selected from fluoro, chloro, bromo, —OR$^{8a}$, —SH, —NR$^{9a}$R$^{10a}$ or —$C_{1-3}$alkyl;
$R^4$ is selected from:
(a) —$C_{1-10}$alkyl unsubstituted or substituted with one to three substituents independently selected from fluoro, chloro, bromo, —OR$^{7b}$, —SH, —NR$^{9b}$R$^{10b}$, —$C_{3-6}$cycloalkyl or spiro—$C_{3-6}$cycloalkyl,
(b) —CH$_2$-phenyl unsubstituted or substituted with one to three substituents independently selected from fluoro, chloro, bromo, —OR$^{8b}$, —SH, —NR$^{9b}$R$^{10b}$ or —$C_{1-3}$alkyl,
(c) —$C_{3-8}$cycloalkyl unsubstituted or substituted with one to three substituents independently selected from fluoro, chloro, bromo, —OR$^{8b}$, —SH, —NR$^{9b}$R$^{10b}$ or —$C_{1-3}$alkyl,
(d) aryl unsubstituted or substituted with one to three substituents independently selected from fluoro, chloro, bromo, —OR$^{8b}$, —SH, —NR$^{9b}$R$^{10b}$ or —$C_{1-3}$alkyl,
(e) —$C_{1-5}$alkyl—X—$C_{1-5}$alkyl wherein X is O, S or NH,
(f) heteroaryl unsubstituted or substituted with one to three substituents independently selected from fluoro chloro, bromo, —OR$^{8b}$, —SH, —NR$^{9b}$R$^{10b}$ or —$C_{1-3}$alkyl, or
(g) a heterocyclic ring unsubstituted or substituted with one to three substituents independently selected from fluoro, chloro, bromo, —OR$^{8b}$, —SH, —NR$^{9b}$R$^{10b}$ or —$C_{1-3}$alkyl;
$R^5$ and $R^6$ are each independently selected from (a) —$C_{1-4}$alkyl, (b) —$C_{1-4}$alkyl substituted with —OH, —SH, —SCH$_3$, —NH$_2$, —NcyC(=NH)—NH$_2$, (c) —CH$_2$-phenyl, (d) —CH$_2$-phenol, (e) —(CH$_2$)$_{1-2}$—COOH, (f) —(CH$_2$)$_{1-2}$—CONH$_2$, (g) —CH$_2$-1H-indole, (h) —CH$_2$-imidazole, (i) aryl or (j) heteroaryl;
or $R^5$ and $R^6$ are joined together with the carbon to which they are both attached to form —$C_{3-6}$cycloalkyl or a 4 to 6-membered heterocyclic ring;
$R^{7a}$ and $R^{7b}$ are each independently selected from —H or —$C_{3-6}$cycloalkyl;
$R^{8a}$ and $R^{8b}$ are each independently selected from —H, —$C_{1-3}$alkyl or —$C_{3-6}$cycloalkyl;
$R^{9a}$ and $R^{10a}$ are each independently selected from —H, —$C_{1-3}$alkyl or —$C_{3-6}$cycloalkyl; and
$R^{9b}$ and $R^{10b}$ are each independently selected from —H, —$C_{1-3}$alkyl or —$C_{3-6}$cycloalkyl.

2. The compound of claim 1 or a pharmaceutically acceptable salt thereof wherein one of $R^1$ is —H or —$C_{1-4}$alkyl, and $R^2$ is —H, —$C_{1-4}$alkyl or —CH$_2$-phenyl.

3. The compound of claim 2 or a pharmaceutically acceptable salt thereof wherein $R^5$ and $R^6$ are independently selected from —$C_{1-4}$alkyl, or $R^5$ and $R^6$ are joined together with the carbon to which they are both attached to form —$C_{3-6}$cycloalkyl.

4. The compound of claim 3 or a pharmaceutically acceptable salt thereof wherein $R^3$ is:
(a) —$C_{1-8}$alkyl, —CH$_2$CH$_2$OH, —CH$_2$CH$_2$CH$_2$OH, —CH$_2$CH$_2$SH, —CH$_2$CH$_2$CH$_2$SH, —CH$_2$CH$_2$NH$_2$, —CH$_2$CH$_2$CH$_2$NH$_2$,
(b) —CH$_2$-phenyl, unsubstituted or substituted with one to three substituents independently selected from fluoro, chloro, bromo, —OR$^{8a}$, —SH, —NR$^{9a}$R$^{10a}$ or —$C_{1-3}$alkyl,
(c) —$C_{3-6}$cycloalkyl, unsubstituted or substituted with one to three substituents independently selected from fluoro, chloro, bromo, —OR$^{8a}$, —SH, —NR$^{9a}$R$^{10a}$ or —$C_{1-3}$alkyl,
(d) phenyl or naphthyl, each unsubstituted or substituted with one to three substituents independently selected from fluoro, chloro, bromo, —OR$^{8a}$, —SH, —NR$^{9a}$R$^{10a}$ or —$C_{1-3}$alkyl,
(e) —CH$_2$CH$_2$OCH$_3$, —CH$_2$CH$_2$CH$_2$OCH$_3$, —CH$_2$CH$_2$SCH$_3$, —CH$_2$CH$_2$CH$_2$SCH$_3$, —CH$_2$CH$_2$NHCH$_3$, —CH$_2$CH$_2$CH$_2$NHCH$_3$, (f) pyridyl, unsubstituted or substituted with one to three substituents independently selected from fluoro chloro, bromo, —OR$^{8a}$, —SH, —NR$^{9a}$R$^{10a}$ or —C$_{1-3}$alkyl, or
  (g) piperidinyl, pyrrolidinyl, tetrahydrofuranyl, or tetrahydropyranyl, each unsubstituted or substituted with one to three substituents independently selected from fluoro, chloro, bromo, —OR$^{8a}$, —SH, —NR$^{9a}$R$^{10a}$ or —C$_{1-3}$alkyl.

5. The compound of claim 4 or a pharmaceutically acceptable salt thereof wherein R$^4$ is:
  (a) —C$_{1-8}$alkyl, —CH$_2$CH$_2$OH, —CH$_2$CH$_2$CH$_2$OH, —CH$_2$CH$_2$SH, —CH$_2$CH$_2$CH$_2$SH, —CH$_2$CH$_2$NH$_2$, —CH$_2$CH$_2$CH$_2$NH$_2$,
  (b) —CH$_2$-phenyl, unsubstituted or substituted with one to three substituents independently selected from fluoro, chloro, bromo, —OR$^{8b}$, —SH, —NR$^{9b}$R$^{10b}$ or —C$_{1-3}$alkyl,
  (c) —C$_{3-6}$cycloalkyl, unsubstituted or substituted with one to three substituents independently selected from fluoro, chloro, bromo, —OR$^{8b}$, —SH, —NR$^{9b}$R$^{10b}$ or —C$_{1-3}$alkyl,
  (d) phenyl or naphthyl, each unsubstituted or substituted with one to three substituents independently selected from fluoro, chloro, bromo, —OR$^{8b}$, —SH, —NR$^{9b}$R$^{10b}$ or —C$_{1-3}$alkyl,
  (e) —CH$_2$CH$_2$OCH$_3$, —CH$_2$CH$_2$CH$_2$OCH$_3$, —CH$_2$CH$_2$SCH$_3$, —CH$_2$CH$_2$CH$_2$SCH$_3$, —CH$_2$CH$_2$NHCH$_3$, —CH$_2$CH$_2$CH$_2$NHCH$_3$,
  (f) pyridyl, unsubstituted or substituted with one to three substituents independently selected from fluoro chloro, bromo, —OR$^{8b}$, —SH, —NR$^{9b}$R$^{10b}$ or —C$_{1-3}$alkyl, or
  (g) piperidinyl, pyrrolidinyl, tetrahydrofuranyl, or tetrahydropyranyl, each unsubstituted or substituted with one to three substituents independently selected from fluoro, chloro, bromo, —OR$^{8b}$, —SH, —NR$^{9b}$R$^{10b}$ or —C$_{1-3}$alkyl.

6. The compound of claim 1 or a pharmaceutically acceptable salt thereof wherein R$^3$ and R$^4$ are each independently unsubstituted or substituted and each is independently selected from —C$_{1-8}$alkyl, cyclopropyl, cyclobutyl, cyclopentyl, cyclohexyl, or —CH2-phenyl.

7. The compound of claim 2 or a pharmaceutically acceptable salt thereof wherein R$^3$ and R$^4$ are each independently unsubstituted or substituted and each is independently selected from —C$_{1-8}$alkyl, cyclopropyl, cyclobutyl, cyclopentyl, cyclohexyl, or —CH$_2$-phenyl.

8. The compound of claim 3 or a pharmaceutically acceptable salt thereof wherein R$^3$ and R$^4$ are each independently unsubstituted or substituted and each is independently selected from —C$_{1-8}$alkyl, cyclopropyl, cyclobutyl, cyclopentyl, cyclohexyl, or —CH2-phenyl.

9. The compound of claim 1 or a pharmaceutically acceptable salt thereof wherein R$^3$ and R$^4$ are each unsubstituted and independently selected from —C$_{2-6}$alkyl, cyclopropyl, cyclobutyl, cyclopentyl, cyclohexyl, or —CH$_2$-phenyl.

10. The compound of claim 2 or a pharmaceutically acceptable salt thereof wherein R$^3$ and R$^4$ are each unsubstituted and independently selected from —C$_{2-6}$alkyl, cyclopropyl, cyclobutyl, cyclopentyl, cyclohexyl, or —CH$_2$-phenyl.

11. The compound of claim 3 or a pharmaceutically acceptable salt thereof wherein R$^3$ and R$^4$ are each unsubstituted and independently selected from —C$_{2-6}$alkyl, cyclopropyl, cyclobutyl, cyclopentyl, cyclohexyl, or —CH$_2$-phenyl.

12. The compound of claim 1 or a pharmaceutically acceptable salt thereof, wherein:
R$^1$ is —H or —CH$_3$;
R$^2$ is —H, —CH$_3$ or —CH$_2$-phenyl;
R$^3$ is selected from —C$_{1-8}$alkyl, —C$_{3-6}$cycloalkyl or —CH$_2$-phenyl;
R$^4$ is selected from —C$_{1-8}$alkyl or —C$_{3-6}$cycloalkyl; and
R$^5$ and R6 are both —CH$_3$;
or R$^5$ and R$^6$ are joined together with the carbon to which they are both attached to form —C$_{3-6}$cycloalkyl.

13. The compound of claim 1 that is:
Isopropyl 2-4(S)-((((R)-1-(6-amino-9H-purin-9-yl)propan-2-y0oxy)methyl)(((S)-1-isopropoxy-1-oxopropan-2-yl)oxy)phosphoryl)amino)-2-methylpropanoate;
Isopropyl 2-(((R)-((((R)-1-(6-amino-9H-purin-9-yl)propan-2-yl)oxy)methyl)(((S)-1-isopropoxy -1-oxopropan-2-yl)oxy)phosphoryl)amino)-2-methylpropanoate;
Pentyl 2-(((S)-((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate;
Pentyl 2-(((R)-((((R)-1-(6-amino-9H-purin-9-yl)propan-2-yl)oxy)methyl)(((S)-1-isopropoxy-1-oxopropan-2-ypoxy)phosphoryl)amino)-2-methylpropanoate;
Isopropyl 2-(((S)-((((R)-1-(6-amino-9H-purin-9-yl)propan-2-yl)oxy)methyl)(2-isopropoxy-2-oxoethoxy) phosphoryl)amino)-2-methylpropanoate;
Isopropyl 2-(((R)-((((R)-1-(6-amino-9H-purin-9-yl)propan-2-yl)oxy)methyl)(2-isopropoxy-2-oxoethoxy) phosphoryl)amino)-2-methylpropanoate;
Pentyl 2-(((S)-((((R)-1-(6-amino-9H-purin-9-yl)propan-2-yl)oxy)methyl)(2-isopropoxy-2-oxoethoxy)phosphoryl)amino)-2-methylpropanoate;
Pentyl 2-(((R)-((((R)-1-(6-amino-9H-purin-9-yl)propan-2-yl)oxy)methyl)(2-isopropoxy-2-oxoethoxy)phosphoryl)amino)-2-methylpropanoate;
Cyclopentyl 2-(((S)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate;
Cyclopentyl 2-(((R)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate;
Hexyl 2-(((S)-((((R)-1-(6-amino-9H-purin-9-yl)propan-2-yl)oxy)methyl)(2-isopropoxy-2-oxoethoxy)phosphoryl)amino)-2-methylpropanoate;
Hexyl 2-(((R)-((((R)-1-(6-amino-9H-purin-9-yl)propan-2-yl)oxy)methyl)(2-isopropoxy-2-oxoethoxy)phosphoryl)amino)-2-methylpropanoate;
Hexyl 2-(((S)-((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate;
Hexyl 2-(((R)-((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate;
Isopropyl 2-(((R)-((((R)-1-(6-amino-9H-purin-9-yl)propan-2-yl)oxy)methyl)(2-oxo-2-(pentyloxy)ethoxy) phosphoryl)amino)-2-methylpropanoate;
Isopropyl 2-(((S)-((((R)-1-(6-amino-9H-purin-9-yl)propan-2-yl)oxy)methyl)(2-oxo-2-(pentyloxy)ethoxy) phosphoryl)amino)-2-methylpropanoate;
Hexyl 2-(((S)-((((R)-1-(6-amino-9H-purin-9-yl)propan-2-yl)oxy)methyl)(4R)-1-isopropoxy-1-oxopropan-2-yl)oxy)phosphoryl)amino)-2-methylpropanoate;
Hexyl 2-(((R)-((((R)-1-(6-amino-9H-purin-9-yl)propan-2-yl)oxy)methyl)(((R)-1-isopropoxy-1-oxopropan-2-yl)oxy)phosphoryl)amino)-2-methylpropanoate;

Isopropyl 2-(((S)-((((R)-1-(6-amino-9H-purin-9-yl)propan-2-yl)oxy)methyl)(((S)-1-oxo-1-(pentyloxy)propan-2-yl)oxy)phosphoryl)amino)-2-methylpropanoate;
Isopropyl 2-(((R)-((((R)-1-(6-amino-9H-purin-9-yl)propan-2-yl)oxy)methyl)(((S)-1-oxo-1-(pentyloxy)propan-2-yl)oxy)phosphoryl)amino)-2-methylpropanoate;
Butyl 2-(((S)-((((R)-1-(6-amino-9H-purin-9-yl)propan-2-yl)oxy)methyl)(((S)-1-(cyclopentyloxy) -1-oxopropan-2-yl)oxy)phosphoryl)amino)-2-methylpropanoate;
Butyl 2-(((R)-((((R)-1-(6-amino-9H-purin-9-yl)propan-2-yl)oxy)methyl)(((S)-1-(cyclopentyloxy) -1-oxopropan-2-yl)oxy)phosphoryl)amino)-2-methylpropanoate;
Cyclohexyl 2-(((S)-((((R)-1-(6-amino-9H-purin-9-yl)propan-2-yl)oxy)methyl)(((S)-1-isopropoxy -1-oxopropan-2-yl)oxy)phosphoryl)amino)-2-methylpropanoate;
Cyclohexyl 2-(((R)-((((R)-1-(6-amino-9H-purin-9-yl)propan-2-yl)oxy)methyl)(((S)-1-isopropoxy -1-oxopropan-2-yl)oxy)phosphoryl)amino)-2-methylpropanoate;
Isopropyl 2-(((S)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate;
Isopropyl 2-(((S)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate;
Cyclopentyl 2-(((S)-((((R)-1-(6-amino-9H-purin-9-yl)propan-2-yl)oxy)methyl)(2-isopropoxy-2-oxoethoxy)phosphoryl)amino)-2-methylpropanoate;
Cyclopentyl 2-(((R)-((((R)-1-(6-amino-9H-purin-9-yl)propan-2-yl)oxy)methyl)(2-isopropoxy-2-oxoethoxy)phosphoryl)amino)-2-methylpropanoate;
Cyclohexyl 2-(((S)-((((R)-1-(6-amino-9H-purin-9-yl)propan-2-yl)oxy)methyl)(2-isopropoxy-2-oxoethoxy)phosphoryl)amino)-2-methylpropanoate;
Cyclohexyl 2-(((R)-((((R)1-(6-amino-9H-purin-9-yl)propan-2-yl)oxy)methyl)(2-isopropoxy-2-oxoethoxy)phosphoryl)amino)-2-methylpropanoate;
Cyclobutyl 2-(((S)-((((R)-1-(6-amino-9H-purin-9-yl)propan-2-yl)oxy)methyl)(((S)-1-isopropoxy -1-oxopropan-2-yl)oxy)phosphoryl)amino)-2-methylpropanoate;
Cyclobutyl 2-(((R)-((((R)-1-(6-amino-9H-purin-9-yl)propan-2-yl)oxy)methyl)(((S)-1-isopropoxy -1-oxopropan-2-yl)oxy)phosphoryl)amino)-2-methylpropanoate;
Cyclobutyl 2-(((S)-((((R)-1-(6-amino-9H-purin-9-yl)propan-2-yl)oxy)methyl)(2-isopropoxy-2-oxoethoxy)phosphoryl)amino)-2-methylpropanoate;
Cyclobutyl 2-(((R)-((((R)-1-(6-amino-9H-purin-9-yl)propan-2-yl)oxy)methyl)(2-isopropoxy-2-oxoethoxy)phosphoryl)amino)-2-methylpropanoate;
Cyclopentyl 2-(((S)-((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate;
Cyclopentyl 2-(((R)-((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate;
Pentyl 2-(((S)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate;
Pentyl 2-(((R)-((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate;
Isopropyl 2-((((((R)-1-(6-amino-9H-purin-9-yl)propan-2-yl)oxy)methyl) (((R)-1 -is opr op oxy - 1-oxopropan-2-yl)oxy)phosphoryl)amino)-2-methylpropanoate;
Propyl 2-((((((R)-1-(6-amino-9H-purin-9-yl)propan-2-yl)oxy)methyl)(2-isopropoxy-2-oxoethoxy)phosphoryl)amino)-2-methylpropanoate;
Propyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate;
Propyl 2-((((((R)-1-(6-amino-9H-purin-9-yl)propan-2-yl)oxy)methyl)(((R)-1-i sopropoxy-1-oxopropan-2-yl)oxy)phosphoryl)amino)-2-methylpropanoate;
Butyl 2-((((((R)-1-(6-amino-9H-purin-9-yl)propan-2-yl)oxy)methyl)(2-isopropoxy-2-oxoethoxy)phosphoryl)amino)-2-methylpropanoate;
Butyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate;
Butyl 2-((((((R)-1-(6-amino-9H-purin-9-yl)propan-2-yl)oxy)methyl)(((R)-1 -isopropoxy-1-oxopropan-2-yl)oxy)phosphoryl)amino)-2-methylpropanoate;
Ethyl 2-((((((R)-1-(6-amino-9H-purin-9-yl)propan-2-yl)oxy)methyl)(2-isopropoxy-2-oxoethoxy)phosphoryl)amino)-2-methylpropanoate;
Ethyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate;
Ethyl 2-((((((R)-1-(6-amino-9H-purin-9-yl)propan-2-yl)oxy)methyl)(((R)-1-i sopropoxy-1-oxopropan-2-yl)oxy)phosphoryl)amino)-2-methylpropanoate;
Isobutyl 2-((((((R)-1-(6-amino-9H-purin-9-yl)propan-2-ypoxy)methyl)(2-isopropoxy-2-oxoethoxy)phosphoryl)amino)-2-methylpropanoate;
Isobutyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate;
Isopropyl 2-((((((R)-1-(6-amino-9H-purin-9-yl)propan-2-yl)oxy)methyl)(((S)-1-isopropoxy-1-oxo-3-phenylpropan-2-yl)oxy)phosphoryl)amino)-2-methylpropanoate;
Hexyl 2-((((((R)-1-(6-amino-9H-purin-9-yl)propan-2-yl)oxy)methyl)(((S)-1-isopropoxy-1-oxo-3-phenylpropan-2-yl)oxy)phosphoryl)amino)-2-methylpropanoate;
Hexyl 2-((((((R)-1-(6-amino-9H-purin-9-yl)propan-2-yl)oxy)methyl)(((S)-1-(cyclopentyloxy)-1-oxopropan-2-yl)oxy)phosphoryl)amino)-2-methylpropanoate;
Hexyl 2-((((((R)-1-(6-amino-9H-purin-9-yl)propan-2-yl)oxy)methyl)(2-(cyclopentyloxy)-2-oxoethoxy)phosphoryl)amino)-2-methylpropanoate;
Pentyl 2-((((((R)-1-(6-amino-9H-purin-9-yl)propan-2-yl)oxy)methyl)(2-(cyclopentyloxy)-2-oxoethoxy)phosphoryl)amino)-2-methylpropanoate;
Isobutyl 2-((((((R)-1-(6-amino-9H-purin-9-yl)propan-2-yl)oxy)methyl)(((S)-1-(cyclopentyloxy) -1-oxopropan-2-yl)oxy)phosphoryl)amino)-2-methylpropanoate;
Propyl 2-((((((R)-1-(6-amino-9H-purin-9-yl)propan-2-yl)oxy)methyl)(2-(cyclopentyloxy)-2-oxoethoxy)phosphoryl)amino)-2-methylpropanoate;
Cyclopentyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate;
Isopropyl 2-((((((R)-1-(6-amino-9H-purin-9-yl)propan-2-yl)oxy)methyl)(((S)-1-ethoxy-1-oxopropan-2-yl)oxy)phosphoryl)amino)-2-methylpropanoate;
Benzyl 2-((((((R)-1-(6-amino-9H-purin-9-yl)propan-2-yl)oxy)methyl)(((S)-1-isopropoxy-1-oxopropan-2-yl)oxy)phosphoryl)amino)-2-methylpropanoate;
Benzyl 2-((((((R)-1-(6-amino-9H-purin-9-yl)propan-2-yl)oxy)methyl)(2-isopropoxy-2-oxoethoxy)phosphoryl)amino)-2-methylpropanoate;

Hexyl 2-((((((R)-1-(6-amino-9H-purin-9-yl)propan-2-yl)oxy)methyl)(((S)-1-ethoxy-1-oxopropan-2-yl)oxy)phosphoryl)amino)-2-methylpropanoate;

Hexyl 2-((((((R)-1-(6-amino-9H-purin-9-yl)propan-2-yl)oxy)methyl)((1-isopropoxy-2-methyl-1-oxopropan-2-yl)oxy)phosphoryl)amino)-2-methylpropanoate;

Isopropyl 1-((((((R)-1-(6-amino-9H-purin-9-yl)propan-2-yl)oxy)methyl)(2-isopropoxy-2-oxoethoxy)phosphoryl)amino)cyclopentane-1-carboxylate;

Isopropyl 1-((((((R)-1-(6-amino-9H-purin-9-yl)propan-2-yl)oxy)methyl)(2-isopropoxy-2-oxoethoxy)phosphoryl)amino)cyclopropane-1-carboxylate;

Isopropyl 1-((((((R)-1-(6-amino-9H-purin-9-yl)propan-2-yl)oxy)methyl)(((S)-1-isopropoxy-1-oxopropan-2-yl)oxy)phosphoryl)amino)cyclopropane-1-carboxylate;

Isopropyl 1-((((((R)-1-(6-amino-9H-purin-9-yl)propan-2-yl)oxy)methyl)(((S)-1-isopropoxy-1-oxopropan-2-yl)oxy)phosphoryl)amino)cyclopentane-1-carboxylate;

Isopropyl 1-((((((R)-1-(6-amino-9H-purin-9-yl)propan-2-yl)oxy)methyl)(2-isopropoxy-2-oxoethoxy)phosphoryl)amino)cyclobutane-1-carboxylate;

Isopropyl 1-((((((R)-1-(6-amino-9H-purin-9-yl)propan-2-yl)oxy)methyl)(((S)-1-isopropoxy-1-oxopropan-2-yl)oxy)phosphoryl)amino)cyclobutane-l-carboxylate;

Isopropyl 1-((((((R)-1-(6-amino-9H-purin-9-yl)propan-2-yl)oxy)methyl)(2-isopropoxy-2-oxoethoxy)phosphoryl)amino)cyclohexane-1-carboxylate; or Isopropyl 1-((((((R) -1-(6-amino-9H-purin-9-yl)propan-2-yl)oxy)methyl)(((S)-1-isopropoxy-1-oxopropan-2-yl)oxy)phosphoryl)amino)cyclohexane-1-carboxylate;

or a pharmaceutically acceptable salt thereof.

14. A pharmaceutical composition comprising an effective amount of the compound of claim 1, or a pharmaceutically acceptable salt thereof, and a pharmaceutically acceptable carrier.

15. The pharmaceutical composition of claim 14 further comprising an effective amount of one or more additional HIV antiviral agent selected from HIV protease inhibitors, HIV integrase inhibitors, non-nucleoside HIV reverse transcriptase inhibitors, nucleoside HIV reverse transcriptase inhibitors, HIV fusion inhibitors and HIV entry inhibitors.

16. A method for the prophylaxis or treatment of infection by HIV or for the prophylaxis, treatment, or delay in the onset of AIDS in a subject in need thereof which comprises administering to the subject an effective amount of the compound of claim 1 or a pharmaceutically acceptable salt thereof.

17. The method of claim 16 further comprising administering to the subject an effective amount of one or more additional HIV antiviral agent selected from HIV protease inhibitors, HIV integrase inhibitors, non-nucleoside HIV reverse transcriptase inhibitors, nucleoside HIV reverse transcriptase inhibitors, HIV fusion inhibitors and HIV entry inhibitors.

18. The pharmaceutical composition of claim 14 further comprising an effective amount of one or more additional HIV antiviral agent selected from:

abacavir,
abacavir + lamivudine,
abacavir + lamivudine + zidovudine,
amprenavir,
atazanavir,
AZT,
capravirine,
darunavir,
ddC,
ddI,
ddI (enteric coated),
delavirdine,
dolutegravir,
doravirine,
efavirenz,
efavirenz + emtricitabine + tenofovir DF,
4'-ethynyl-2-fluoro-2'-deoxyadenosine,
elvitegravir,
emtricitabine,
emtricitabine + tenofovir DF,
emivirine,
enfuvirtide,
enteric coated didanosine,
etravirine,
fosamprenavir calcium,
indinavir,
lamivudine,
lamivudine + zidovudine,
lopinavir,
lopinavir + ritonavir,
maraviroc,
nelfinavir,
nevirapine,
PPL-100,
raltegravir,
rilpivirine,
ritonavir,
saquinavir,
stavudine,
tipranavir, or
vicriviroc.

* * * * *